US008563020B2

(12) United States Patent
Uhlmann et al.

(10) Patent No.: US 8,563,020 B2
(45) Date of Patent: Oct. 22, 2013

(54) COMPOSITIONS AND METHODS FOR ANTIMICROBIAL METAL NANOPARTICLES

(75) Inventors: Donald R. Uhlmann, Tucson, AZ (US);
Anoop Agrawal, Tucson, AZ (US);
Murat Akarsu, Antalya (TK); John P. Cronin, Tucson, AZ (US)

(73) Assignee: Agienic, Inc., Wilmington, DE (US)

( * ) Notice: Subject to any disclaimer, the term of this patent is extended or adjusted under 35 U.S.C. 154(b) by 0 days.

(21) Appl. No.: 13/523,811

(22) Filed: Jun. 14, 2012

(65) Prior Publication Data

US 2012/0301530 A1    Nov. 29, 2012

Related U.S. Application Data

(62) Division of application No. 13/480,367, filed on May 24, 2012.

(60) Provisional application No. 61/519,523, filed on May 24, 2011, provisional application No. 61/582,322, filed on Dec. 31, 2011.

(51) Int. Cl.
| | | |
|---|---|---|
| *A01P 1/00* | (2006.01) | |
| *B82Y 5/00* | (2011.01) | |
| *A01N 25/04* | (2006.01) | |
| *A01N 25/00* | (2006.01) | |
| *A01N 25/08* | (2006.01) | |
| *A01N 59/20* | (2006.01) | |

(52) U.S. Cl.
USPC ........... 424/405; 424/638; 424/630; 424/618; 977/902; 977/810; 977/773

(58) Field of Classification Search
USPC ....................................................... 424/405
See application file for complete search history.

(56) References Cited

U.S. PATENT DOCUMENTS

| | | | | |
|---|---|---|---|---|
| 2,739,922 | A | 3/1956 | Shelanski | 167/70 |
| 4,533,435 | A | 8/1985 | Intili | 162/161 |
| 5,344,636 | A * | 9/1994 | Miyata | 424/688 |
| 5,792,793 | A | 8/1998 | Oda et al. | 514/495 |
| 5,919,554 | A | 7/1999 | Watterson, III et al. | 428/201 |
| 5,968,207 | A | 10/1999 | Li | 8/490 |
| 6,093,407 | A | 7/2000 | Cummings et al. | 424/400 |
| 6,108,847 | A | 8/2000 | Cueman et al. | 15/104.94 |
| 6,171,496 | B1 | 1/2001 | Patil | 210/484 |
| 6,187,456 | B1 | 2/2001 | Lever | 428/688 |
| 6,197,072 | B1 | 3/2001 | Li | 8/490 |
| 6,238,575 | B1 | 5/2001 | Patil | 210/764 |
| 6,248,342 | B1 | 6/2001 | Trogolo et al. | 424/404 |
| 6,267,590 | B1 | 7/2001 | Barry et al. | 433/8 |
| 6,283,308 | B1 | 9/2001 | Patil et al. | 210/484 |
| 6,296,863 | B1 | 10/2001 | Trogolo et al. | 424/404 |
| 6,299,651 | B1 | 10/2001 | Li | 8/115.64 |
| 6,332,293 | B1 | 12/2001 | Kerr et al. | 52/177 |
| 6,342,212 | B1 | 1/2002 | Schuette et al. | 424/78.1 |
| 6,365,130 | B1 | 4/2002 | Barry et al. | 424/48 |
| 6,432,416 | B1 | 8/2002 | Cummings et al. | 424/400 |
| 6,436,422 | B1 | 8/2002 | Trogolo et al. | 424/405 |
| 6,448,305 | B1 | 9/2002 | Watterson, III et al. | 523/122 |
| 6,448,306 | B1 | 9/2002 | Lever et al. | 523/122 |
| 6,454,813 | B1 | 9/2002 | Chan | 8/115.51 |
| 6,455,610 | B1 | 9/2002 | Lever et al. | 523/122 |
| 6,461,386 | B1 | 10/2002 | Chan et al. | 8/115.51 |
| 6,479,144 | B2 | 11/2002 | Petrea et al. | 428/379 |
| 6,482,756 | B2 | 11/2002 | Li | 442/123 |
| 6,531,519 | B2 | 3/2003 | Patil | 521/33 |
| 6,540,915 | B2 | 4/2003 | Patil | 210/500.27 |
| 6,540,916 | B2 | 4/2003 | Patil | 210/502.1 |
| 6,544,621 | B1 | 4/2003 | Schuette et al. | 428/97 |
| 6,555,599 | B2 | 4/2003 | Lever et al. | 523/122 |
| 6,582,715 | B1 | 6/2003 | Barry et al. | 424/422 |
| 6,585,767 | B1 | 7/2003 | Holley et al. | 623/2.41 |
| 6,605,751 | B1 | 8/2003 | Gibbins et al. | 602/41 |
| 6,641,829 | B1 | 11/2003 | Green et al. | 424/405 |
| 6,641,842 | B2 | 11/2003 | Laridon et al. | 424/486 |
| 6,716,895 | B1 | 4/2004 | Terry | 523/122 |
| 6,728,969 | B2 | 5/2004 | Zeiler | 2/4 |
| 6,767,647 | B2 | 7/2004 | Swofford et al. | 428/537.7 |
| 6,797,278 | B2 | 9/2004 | Jackson et al. | 424/409 |

(Continued)

FOREIGN PATENT DOCUMENTS

| | | | | |
|---|---|---|---|---|
| EP | 2184109 | 5/2010 | | B02C 7/14 |
| EP | 2332554 | 6/2011 | | A61K 33/18 |

(Continued)

OTHER PUBLICATIONS

Office Action, U.S. Appl. No. 13/480,367 dated Oct. 1, 2012 (23 pgs).
International Search Report and the Written Opinion issued for PCT/US12/39462, dated Oct. 15, 2012 (13 pgs).
Office Action issued Nov. 6, 2012 in corresponding U.S. Appl. No. 13/525,115, 21 pgs.
Office Action issued Nov. 14, 2012 in corresponding U.S. Appl. No. 13/525,127, 19 pgs.
Office Action issued Nov. 15, 2012 in corresponding U.S. Appl. No. 13/525,121, 22 pgs.
Office Action issued Nov. 15, 2012 in corresponding U.S. Appl. No. 13/525,809, 18 pgs.
Office Action issued Jan. 22, 2013 in corresponding U.S. Appl. No. 13/480,367, 18 pgs.

(Continued)

*Primary Examiner* — Richard Schnizer
*Assistant Examiner* — Audrea Buckley
(74) *Attorney, Agent, or Firm* — Hayes Soloway P.C.

(57) ABSTRACT

Embodiments of the invention are directed to a composition having antimicrobial activity comprising particles comprising at least one inorganic copper salt; and at least one functionalizing agent in contact with the particles, the functionalizing agent stabilizing the particle in a carrier such that an antimicrobially effective amount of ions are released into the environment of a microbe. The average size of the particles ranges from about 1000 nm to about 4 nm. Preferred copper salts include copper iodide, copper bromide and copper chloride. Preferred functionalizing agents include amino acids, thiols, hydrophilic polymers emulsions of hydrophobic polymers and surfactants.

31 Claims, 3 Drawing Sheets

(56) References Cited

U.S. PATENT DOCUMENTS

| | | | | |
|---|---|---|---|---|
| 6,821,936 | B2 | 11/2004 | Green et al. | 510/319 |
| 6,846,871 | B2 | 1/2005 | Patel et al. | 524/440 |
| 6,849,214 | B2 | 2/2005 | Patil | 264/45.1 |
| 6,852,776 | B2 | 2/2005 | Ong et al. | 523/122 |
| 6,852,782 | B2 | 2/2005 | Patel et al. | 524/287 |
| 6,854,601 | B2 | 2/2005 | Patil | 210/484 |
| 6,866,859 | B2 | 3/2005 | Trogolo et al. | 424/423 |
| 6,897,349 | B2 * | 5/2005 | Gibbins et al. | 602/48 |
| 6,943,205 | B2 | 9/2005 | Patel et al. | 523/122 |
| 6,946,433 | B2 | 9/2005 | Green et al. | 510/319 |
| 6,949,598 | B2 | 9/2005 | Terry | 524/398 |
| 6,979,455 | B2 | 12/2005 | Ong et al. | 424/411 |
| 7,080,412 | B2 | 7/2006 | Zeiler | 2/4 |
| 7,087,255 | B2 | 8/2006 | McGrew et al. | 426/5 |
| 7,098,256 | B2 | 8/2006 | Ong et al. | 522/97 |
| 7,132,378 | B2 | 11/2006 | Kreider et al. | 442/117 |
| 7,135,449 | B2 | 11/2006 | Li et al. | 510/278 |
| 7,169,402 | B2 | 1/2007 | Gabbay | 424/404 |
| 7,199,093 | B2 | 4/2007 | Li et al. | 510/278 |
| 7,223,443 | B2 | 5/2007 | Ong | 427/372.2 |
| 7,250,178 | B2 | 7/2007 | Olsson et al. | 424/641 |
| 7,255,852 | B2 | 8/2007 | Gallis et al. | 424/54 |
| 7,291,570 | B1 | 11/2007 | Green et al. | 442/123 |
| 7,296,690 | B2 | 11/2007 | Gabbay | 210/501 |
| 7,354,596 | B1 | 4/2008 | Banovetz et al. | 424/408 |
| 7,357,949 | B2 | 4/2008 | Trogolo et al. | 424/617 |
| 7,381,715 | B2 | 6/2008 | Sabesan | 514/55 |
| 7,425,526 | B2 | 9/2008 | Li et al. | 510/278 |
| 7,426,776 | B2 | 9/2008 | Love, III et al. | 28/167 |
| 7,507,281 | B2 | 3/2009 | Ong et al. | 106/18.32 |
| 7,576,255 | B2 | 8/2009 | Gibbins et al. | 602/48 |
| 7,579,389 | B2 | 8/2009 | Ong | 523/122 |
| 7,585,902 | B2 | 9/2009 | Trogolo | 523/122 |
| 7,595,355 | B2 | 9/2009 | Trogolo | 523/122 |
| 7,598,300 | B2 | 10/2009 | Trogolo | 523/122 |
| 7,645,824 | B2 | 1/2010 | Hendriks et al. | 524/403 |
| 7,648,534 | B2 | 1/2010 | Li et al. | 8/115.58 |
| 7,700,133 | B2 | 4/2010 | Cooley et al. | 424/600 |
| 7,851,653 | B2 | 12/2010 | Getman et al. | 564/295 |
| 7,858,141 | B2 | 12/2010 | Getman et al. | 427/2.1 |
| 7,858,539 | B2 | 12/2010 | Li et al. | 442/123 |
| 7,858,674 | B2 | 12/2010 | Haas et al. | 523/122 |
| 7,951,853 | B2 | 5/2011 | Ismail et al. | 523/122 |
| 2002/0047058 | A1 | 4/2002 | Verhoff et al. | 241/26 |
| 2003/0029789 | A1 | 2/2003 | Patil | 210/501 |
| 2003/0095230 | A1 | 5/2003 | Neely et al. | 351/159 |
| 2003/0163875 | A1 | 9/2003 | Cliver et al. | 8/115.51 |
| 2003/0234068 | A1 | 12/2003 | Swofford et al. | 156/39 |
| 2004/0086683 | A1 | 5/2004 | Higgins et al. | 428/95 |
| 2004/0121077 | A1 | 6/2004 | Park et al. | 427/383.1 |
| 2004/0166173 | A1 | 8/2004 | Albach | 424/618 |
| 2004/0253435 | A1 | 12/2004 | Nomura | 428/327 |
| 2005/0028563 | A1 | 2/2005 | Mullins et al. | 66/202 |
| 2005/0106336 | A1 | 5/2005 | Ong et al. | 428/15 |
| 2005/0147657 | A1 | 7/2005 | Canada et al. | 424/445 |
| 2005/0154030 | A1 | 7/2005 | Payne | 514/358 |
| 2005/0158400 | A1 | 7/2005 | Olsson et al. | 424/641 |
| 2005/0181691 | A1 | 8/2005 | Klutz et al. | 442/59 |
| 2005/0182140 | A1 | 8/2005 | Payne | 514/442 |
| 2005/0196430 | A1 | 9/2005 | Olsson et al. | 424/443 |
| 2005/0239358 | A1 | 10/2005 | Hanrahan et al. | 442/123 |
| 2005/0258093 | A1 | 11/2005 | Cueman et al. | 210/501 |
| 2006/0014810 | A1 | 1/2006 | Payne | 514/367 |
| 2006/0018966 | A1 | 1/2006 | Lin et al. | 424/484 |
| 2006/0048671 | A1 | 3/2006 | Ong | 106/15.05 |
| 2006/0068662 | A1 | 3/2006 | Hanrahan et al. | 442/123 |
| 2006/0166024 | A1 | 7/2006 | Ong et al. | 428/524 |
| 2006/0167130 | A1 | 7/2006 | Ong et al. | 523/122 |
| 2006/0188487 | A1 | 8/2006 | Thomas et al. | 424/93.7 |
| 2006/0217515 | A1 | 9/2006 | Getman et al. | 528/38 |
| 2006/0223962 | A1 | 10/2006 | Getman et al. | 528/10 |
| 2006/0267234 | A1 | 11/2006 | Ong et al. | 264/71 |
| 2007/0004300 | A1 | 1/2007 | Kreider et al. | 442/59 |
| 2007/0021528 | A1 | 1/2007 | Ong | 523/122 |
| 2007/0072753 | A1 | 3/2007 | Ong | 482/148 |
| 2007/0081958 | A1 | 4/2007 | Bechert et al. | 424/70.1 |
| 2007/0110781 | A1 | 5/2007 | Kotterer et al. | 424/405 |
| 2007/0184079 | A1 | 8/2007 | Gabbay | 424/404 |
| 2007/0195259 | A1 | 8/2007 | Olsson | 351/43 |
| 2007/0195260 | A1 | 8/2007 | Olsson et al. | 351/43 |
| 2007/0196605 | A1 | 8/2007 | Ong | 428/35.7 |
| 2007/0199890 | A1 | 8/2007 | Trogolo | 210/500.1 |
| 2007/0207335 | A1 | 9/2007 | Karandikar et al. | 428/560 |
| 2007/0243263 | A1 | 10/2007 | Trogolo | 424/604 |
| 2007/0254044 | A1 | 11/2007 | Karandikar et al. | 424/618 |
| 2007/0281096 | A1 | 12/2007 | Ong et al. | 427/372.2 |
| 2007/0292486 | A1 | 12/2007 | Sen et al. | 424/443 |
| 2008/0017307 | A1 | 1/2008 | Ong et al. | 156/307.1 |
| 2008/0026028 | A1 * | 1/2008 | Schroeder et al. | 424/405 |
| 2008/0044458 | A1 | 2/2008 | MacDonald et al. | 424/443 |
| 2008/0047894 | A1 | 2/2008 | Trogolo et al. | 210/500.1 |
| 2008/0057134 | A1 | 3/2008 | Crudden | 424/617 |
| 2008/0102122 | A1 | 5/2008 | Mahadevan et al. | 424/484 |
| 2008/0147019 | A1 | 6/2008 | Song et al. | 604/265 |
| 2008/0182125 | A1 | 7/2008 | Krishnan et al. | 428/688 |
| 2008/0193496 | A1 | 8/2008 | Gabbay | 424/404 |
| 2008/0311165 | A1 | 12/2008 | Gabbay | 424/402 |
| 2009/0010969 | A1 | 1/2009 | Gabbay | 424/401 |
| 2009/0010994 | A1 | 1/2009 | Qvist et al. | 424/445 |
| 2009/0035342 | A1 | 2/2009 | Karandikar et al. | 424/411 |
| 2009/0092538 | A1 | 4/2009 | Khanolkar et al. | 423/491 |
| 2009/0104459 | A1 | 4/2009 | Campbell, Jr. | 428/446 |
| 2009/0129541 | A1 | 5/2009 | Ong et al. | 378/44 |
| 2009/0191247 | A1 | 7/2009 | Jose-Yacaman et al. | 424/402 |
| 2009/0260106 | A1 | 10/2009 | Altier et al. | 800/279 |
| 2010/0227052 | A1 | 9/2010 | Carter et al. | 427/161 |
| 2010/0236715 | A1 | 9/2010 | Hanrahan et al. | 156/331.3 |
| 2010/0317640 | A1 | 12/2010 | Nelson et al. | 514/188 |
| 2011/0000616 | A1 | 1/2011 | Hanrahan et al. | 156/307.5 |
| 2011/0065804 | A1 | 3/2011 | Diaddario et al. | 514/690 |
| 2011/0081530 | A1 | 4/2011 | Robinson et al. | 428/212 |
| 2011/0097370 | A1 | 4/2011 | Wang et al. | 424/405 |
| 2011/0195108 | A1 | 8/2011 | Fujimori et al. | 424/443 |
| 2011/0200656 | A1 | 8/2011 | Olsson | 424/405 |
| 2011/0262513 | A1 | 10/2011 | Fujimori et al. | 424/411 |

FOREIGN PATENT DOCUMENTS

| | | | | |
|---|---|---|---|---|
| WO | WO2006096205 | | 9/2006 | F16C 33/58 |
| WO | WO 2008127299 | | 10/2008 | A01N 59/16 |
| WO | WO 2009048556 | | 4/2009 | A61L 12/08 |

OTHER PUBLICATIONS

Fujimori et al., "Novel Antiviral Characteristics of Nanosized Copper(I) Iodide Particles Showing Inactivation Activity against 2009 Pandemic H1N1 Influenza Virus," Applied and Environmental Microbiology, 2012, vol. 78, No. 4, pp. 951-955.

Stenger et al., "Nanomilling in stirred media mills," Chemical Engineering Science, vol. 60, 2005, pp. 4557-4565 (9 pgs).

Kwade et al., "Wet Grinding in Stirred Media Mills," Handbook of Powder Technology: Particle Breakage, Chapter 6, vol. 12, Elsevier, 2007, pp. 251-382 (132 pgs).

PCT International Search Report issued in corresponding application No. PCT/US2012/066550, dated Feb. 8, 2013 (10 pgs).

Jo et al., "Antifungal Activity of Silver Ions and Nanoparticles on Phytopathogenic Fungi," Plant Disease, vol. 93, No. 10, 2009, pp. 1037-1043 (7 pgs).

Morones et al., "The bacterial effect of silver nanoparticles," Nanotechnology, vol. 16, 2005, pp. 2346-2353 (8 pgs).

Badawi et al., "Copper (II)-surfactant complex and its nano analogue as potential antitumor agents," Metal Ions in Biology and Medicine, vol. 10, 2008, pp. 158-166 (9 pgs).

Lichter et al., "Design of Antibacterial Surfaces and Interfaces: Polyelectrolyte Multilayers as a Multifunctional Platform," Macromolecules, vol. 42, No. 22, 2009, pp. 8573-8586 (14 pgs).

Pal et al., "Does the Antibacterial Activity of Silver Nanoparticles Depend on the Shape of the Nanoparticle? A Study of the Gram-Negative Bacterium *Escherichia coli*," Applied and Environmental Microbiology, Mar. 2007, pp. 1712-1720 (9 pgs).

Kvitek et al., "Effect of Surfactants and Polymers on Stability and Antibacterial Activity of Silver Nanoparticles (NPs)," J. Phys. Chem. C, vol. 112, No. 15, 2008, pp. 5825-5834 (10 pgs).

(56) References Cited

OTHER PUBLICATIONS

Michels et al., "Effects of temperature and humidity on the efficacy of methicillin-resistant *Staphylococcus aureus* challenged antimicrobial materials containing silver and copper," Letters in Applied Microbiology, vol. 49, 2009, pp. 191-195 (5 pgs)

Xu et al., "Fabrication, characterization and optical property of CuI nanospheres," Materials Letters, vol. 65, 2011, pp. 1699-1702 (4 pgs).

Yang et al., "A Facile Chemical Solution Route to Convert Bulk Cuprous Iodide into Nanoparticles," Chemistry Letters, vol. 34, No. 7, 2005, pp. 902-903 (2 pgs).

Bokshits et al., "Formation of CuI Colloidal Particles in Aqueous Solution," Colloid Journal, vol. 66, No. 1, 2004, pp. 25-28 (4 pgs).

Bokshits et al., "Formation of Silver and Copper Nanoparticles upon the Reduction of Their Poorly Soluble Precursors in Aqueous Solution," Colloid Journal, vol. 66, No. 5, 2004, pp. 517-522 (6 pgs).

Abbasi et al., "Formation of silver iodide nanoparticles on silk fiber by means of ultrasonic irradiation," Ultrasonics Sonochemistry, vol. 17, 2010, pp. 704-710 (7 pgs).

Gajbhiye et al., "Fungus-mediated synthesis of silver nanoparticles and their activity against pathogenic fungi in combination with fluconazole," Nanomedicine: Nanotechnology, Biology, and Medicine, vol. 5, 2009, pp. 382-386 (5 pgs).

Horie et al., "Inactivation and morphological changes of avian influenza virus by copper ions," Arch Virol, vol. 153, 2008, pp. 1467-1472 (6 pgs).

Lin et al., "Individual and Combined Effects of Copper and Silver Ions on Inactivation of *Legionella pneumophila*," Wat. Res., vol. 30, No. 8, 1996, pp. 1905-1913 (9 pgs).

Fujimori et al., "Introduction of copper iodide fine particles into a poly(acrylic acid) matrix via a complex of polymer-polyiodide ions," Journal of Materials Chemistry, vol. 15, 2005, pp. 4816-4822 (7 pgs).

Wang et al., "Mechanisms of PVP in the preparation of silver nanoparticles," Materials Chemistry and Physics, vol. 94, 2005, pp. 449-453 (5 pgs).

Stoimenov et al., "Metal Oxide Nanoparticles as Bactericidal Agents," Langmuir, vol. 18, No. 17, 2002, pp. 6679-6686 (8 pgs).

Juhnke et al., "Nanoparticles of soft materials by high-energy milling at low temperatures," Institut for Mechanische Verfahrenstechnik, Clausthal University of Technology, Leibnizstrasse 19, 38678 Clausthal-Zellerfeld, Germany (10 pgs), 2005.

Gouveia, I., "Nanobiotechnology: A new strategy to develop non-toxic antimicrobial textiles," Current Research, Technology and Education Topics in Applied Microbiology and Microbial Biotechnology, A. Mendez-Vilas (Ed.) (8 pgs), 2010.

Hoppe et al., "One-Step Synthesis of Gold and Silver Hydrosols Using Poly(N-vinyl-2-pyrrolidone) as a Reducing Agent," Langmuir, vol. 22, 2006, pp. 7027-7034 (8 pgs).

Guo et al., "Preparation and characterization of AgI nanoparticles with controlled size, morphology and crystal structure," Solid State Ionics, vol. 177, 2006, pp. 2467-2471 (5 pgs).

Kauffman et al, "Purification of Copper (I) Iodide," Inorganic Syntheses, vol. 22, 1983, pp. 101-103 (2 pgs).

Gao et al., "Recent Advances in Antimicrobial Treatments of Textiles," Textile Research Journal, vol. 78, No. 1, 2008, pp. 60-72 (13 pgs).

Sambhy et al., "Silver Bromide Nanoparticle/Polymer Composites: Dual Action Tunable Antimicrobial Materials," J. Am. Chem. Soc., vol. 128, 2006, pp. 9798-9808 (11 pgs).

Panacek et al., "Silver Colloid Nanoparticles: Synthesis, Characterization, and Their Antibacterial Activity," J. Phys. Chem. B, vol. 110, No. 33, 2006, pp. 16248-16253 (6 pgs).

Lee et al., "The Silver Nanoparticle (Nano-Ag): A New Model for Antifungal Agents," School of Life Sciences and Biotechnology, College of Natural Sciences, Kyungpook National University, Republic of Korea, pp. 295-308 (14 pgs).

Jain et al., "Silver Nanoparticles in Therapeutics: Development of an Antimicrobial Gel Formulation for Topical Use," Molecular Pharmaceutics, vol. 6, No. 5, pp. 1388-1401 (14 pgs), 2009.

Kumar et al., "Silver-nanoparticle-embedded antimicrobial paints based on vegetable oil," Nature Materials, vol. 7, 2008, pp. 236-241 (7 pgs).

Ruparelia et al., "Strain specificity in antimicrobial activity of silver and copper nanoparticles," Acta Biomaterialia, vol. 4, No. 3, 2008, pp. 707-716 (10 pgs).

Rataboul et al., "Synthesis and characterization of monodisperse zinc and zinc oxide nanoparticles from the organometallic precursor $[Zn(C_6H_{11})_2]$," Journal of Organometallic Chemistry, vol. 643-644, 2002, pp. 307-312 (6 pgs).

Carotenuto, G., "Synthesis and characterization of poly(N-vinylpyrrolidone) filled by monodispersed silver clusters with controlled size," Applied Organometallic Chemistry, vol. 15, 2001, pp. 344-351 (9 pgs).

Liu et al., "Synthesis of β-phase $Ag_{1-x}Cu_xI$ (x=0-0.5) solid solutions nanocrystals," Materials Research Bulletin, vol. 46, 2011, pp. 910-913 (4 pgs).

Niskanen et al., "Synthesis of copolymer-stabilized silver nanoparticles for coating materials," Colloid Polym Sci, vol. 288, 2010, pp. 541-53 (11 pgs).

Biswas et al., "Synthesis of Nanoparticles of CuI, $CuCrO_4$, and CuS in Water/AOT/Cyclohexanone and Water/TX-100 + i-Propanol/Cyclohexanone Reverse Microemulsions," Journal of Dispersion Science and Technology, vol. 25, No. 6, 2004, pp. 801-816 (17 pgs).

Yang et al., "Synthesis of Well-dispersed CuI Nanoparticles from an Available Solution Precursor," Chemistry Letters, vol. 34, No. 8, 2005, pp. 1158-1159 (2 pgs).

Cusumano et al., "Treatment and Prevention of Urinary Tract Infection with Orally Active FimH Inhibitors," Science Translational Medicine, vol. 3, No. 109, 2011, pp. 1-10 (11 pgs).

Office Action issued in corresponding U.S. Appl. No. 13/525,115, dated Feb. 28, 2013 (19 pgs).

Office Action issued in corresponding U.S. Appl. No. 13/527,809, dated Mar. 1, 2013 (20 pgs).

Office Action issued in corresponding U.S. Appl. No. 13/525,127, dated Mar. 7, 2013 (16 pgs).

Office Action issued in corresponding U.S. Appl. No. 13/525,121, dated Mar. 7, 2013 (19 pgs).

\* cited by examiner

**Germination of *Bacillus cereus* spores under defined growth conditions**

Figure 1

**Germination of *Bacillus cereus* spores under defined growth conditions**

Figure 2

COMPOSITIONS AND METHODS FOR ANTIMICROBIAL METAL NANOPARTICLES

CROSS REFERENCE TO RELATED APPLICATIONS

This application is a divisional of co-pending U.S. application Ser. No. 13/480,367, filed May 24, 2012, which application in turn claims priority to U.S. Provisional Patent Application Ser. No. 61/519,523, filed May 24, 2011, and U.S. Provisional Patent Application Ser. No. 61/582,322 filed Dec. 24, 2011, both of which are incorporated herein by reference in their entirety.

FIELD OF THE INVENTION

The invention relates to antimicrobial compositions comprising inorganic copper salt nanoparticles, their preparation, combinations of copper-based nanoparticles with metal and other metal salt nanoparticles, application of the compositions to surfaces and methods of preparation and use.

BACKGROUND OF THE INVENTION

The antimicrobial effect of various metals and their salts has been known for centuries. Hippocrates wrote that silver had beneficial healing and antidisease properties, and the Phoenicians stored water, wine, and vinegar in silver bottles to prevent spoiling. In the early 20th century, silver coins were put in milk bottles to prolong the milk's freshness. Its germicidal effects increased its value in utensils and as jewelry. The exact process of silver's germicidal effect is still not entirely understood, although theories exist. One of these is the "oligodynamic effect," which qualitatively explains the effect on some microorganisms, but cannot explain antiviral effects. Silver is widely used in topical gels and impregnated into bandages because of its wide-spectrum antimicrobial activity.

The oligodynamic effect is demonstrated by other metals, specifically gold, silver, copper, zinc, and bismuth. Copper is one such metal. Copper has long been used as a biostatic surface to line the bottoms of ships to protect against barnacles and mussels. It was originally used in pure form, but has since been superseded by brass and other alloys due to their lower cost and higher durability. Bacteria will not grow on a copper surface because it is biostatic. Copper alloys have become important netting materials in the aquaculture industry for the fact that they are antimicrobial and prevent biofouling and have strong structural and corrosion-resistant properties in marine environments. Organic compounds of copper are useful for preventing fouling of ships' hulls. Copper alloy touch surfaces have recently been investigated as antimicrobial surfaces in hospitals for decreasing transmission of nosocomial infections.

The antimicrobial properties of silver stem from the chemical properties of its ionized form, Ag+, and several mechanisms have been proposed to explain this effect. For example, silver ions form strong molecular bonds with other substances used by bacteria to respire, such as enzymes containing sulfur, nitrogen, and oxygen. When the Ag+ ion forms a complex with these biomolecules, they are rendered inactive, depriving them of necessary activity and eventually leading to the bacteria's death. Silver ions can also complex with bacterial DNA, impairing the ability of the microorganisms to reproduce. The mechanism for copper ions, on the other hand, is not so well understood. Numerous scientific investigations have focused on the role of the metal form of copper, and have concluded that multiple mechanisms may be possible for copper's antimicrobial effect, including increased production of reactive oxidation species such as singlet oxygen and hydroxide radicals, covalent binding of copper metal to reactive sites in enzymes and co-factors, interference with lipid bilayer transport proteins, and interaction of copper ions with moieties of microorganisms analogous to what have been proposed for silver ions.

It is clear that silver and its various compounds and salts have been the overwhelming favorite in terms of its use as an antimicrobial agent. However, silver in the form of the silver halides silver iodide, silver bromide and silver chloride is well-known to be light-sensitive and was used for many years in photography. Copper, aside from its use in preserving marine objects such as ship hulls, has not generally been used in antimicrobial compounds.

Provision of the oligodynamic metal species in the form of fine particles, including the form of nanoparticles, avoids problems such as settling of the particles in solutions—but introduces a complication in trying to estimate the solubility for a given small particle size or the concentration of free ions produced by contact of specific aqueous solutions with a given set of nanometal particles, in addition to the ubiquitous issue of agglomeration. Use of oligodynamic metal species in the form of nanoparticles introduces a further observation—viz., based on several reports in the literature, such particles may under some (generally unspecified) conditions be taken up by the outer membranes of pathogens and transported into the bodies of the pathogens. In many cases, it is expected that this observation would be advantageous for the antimicrobial effectiveness of the metal species.

It is presently unknown under what precise conditions does such penetration by specific nanoparticles of oligodynamic materials take place; and it is certainly unknown what conditions (including particle size and chemistry) promote or mitigate against such penetration. What is needed are better broad-spectrum antimicrobial compositions that may better target oligodynamic metal compounds to microbes and other pathogens.

SUMMARY OF THE INVENTION

The inventors associated with this patent have made the surprising discovery that particles of certain copper salts have much greater efficacy against a broad range of microbes, viruses, molds and fungi than similar silver-based antimicrobial particles. In particular, it has been discovered that copper salts including the copper halide copper iodide ("CuI"), when formulated in accordance with the teachings herein, is surprisingly effective as a broad-spectrum, fast-acting antimicrobial agent.

A first embodiment of the invention is directed to a composition having antimicrobial activity comprising particles comprising at least one inorganic copper salt; and at least one functionalizing agent in contact with the particles, the functionalizing agent stabilizing the particles in a carrier such that an antimicrobially effective amount of ions are released into the environment of a microbe. In one embodiment the carrier is a liquid in which the functionalizing agent is soluble. In another embodiment the carrier is a liquid in which the functionalizing agent is insoluble but stabilized in the carrier. The functionalizing agent acts to complex the particles thereby stabilizing them in the liquid. In some embodiments the liquid carrier is water-based, and in others it is oil-based. In the liquid carrier embodiment the particles are suspended by the liquid carrier in solution. In other embodiments the carrier is a solid such as a melt-blend plastic. In another embodiment the inorganic copper salt comprises a copper halide salt. In other embodiments the halide is selected from the group consisting of iodide, bromide and chloride, and a particularly preferred embodiment is copper iodide (CuI). Preferably the average size of such particles ranges from about 1000 nm to as small as 4 nm. In further embodiments the particles have average sizes of less than about 300 nm, 100 nm, 30 nm or even less than about 10 nm. In yet further embodiments the copper halide has a solubility of less than 100 mg/liter in water, or even less than 15 mg/liter in water.

Another embodiment is directed to a composition having antimicrobial activity comprising particles comprising at least one inorganic copper salt selected from the group consisting of CuI, CuBr and CuCl and having an average size of about 1000 nm or less; at least one functionalizing agent in contact with said particles, said functionalizing agent being present at a weight ratio of from about 100:1 to about 0.5:1.

Embodiments of the invention include functionalizing agents that can include an amino acid, a thiol, a polymer especially a hydrophilic polymer, emulsions of hydrophobic polymers, surfactants, or a ligand-specific binding agent. Preferred embodiments of amino acid agents include aspartic acid, leucine and lysine; preferred embodiments of thiol agents include aminothiol, thioglycerol, thioglycine, thiolactic acid, thiomalic acid, thiooctic acid and thiosilane. Preferred embodiments of hydrophilic polymers include polyvinylpyrollidone, polyethyleneglycol and copolymers and blends comprising at least one of the monomers which form the said polymers. Other preferred polymers include polyurethanes, acrylic polymers, epoxies, silicones and fluorosilicones, particularly when used as emulsions and solutions during surface modification. Preferred embodiments of the invention utilize copper halides such as CuI, CuBr and CuCl. Yet further embodiments of the invention include compositions additionally comprising at least one of a silver particle or a silver halide particle. The silver or silver halide particle may be functionalized with a member selected from the group consisting of an amino acid, a thiol, a hydrophilic polymer or a ligand-specific agent. Further embodiments of the silver halide include a halide chosen from iodide, bromide and chloride.

Another embodiment of the invention described herein is a composition having antimicrobial activity made according to the process comprising the steps of obtaining CuI powder; dissolving the CuI powder in a polar nonaqueous solvent; adding an amount of functionalizing agent sufficient to stabilize said CuI in the polar, nonaqueous solvent; removing the solvent sufficient to dry said stabilized CuI particles whereby a functionalizing agent-complexed CuI particle powder is formed; dispersing the functionalizing agent-complexed CuI particle powder in an aqueous solution having a pH of from about 1 to about 6 to form CuI particles stabilized in water; and optionally drying the stabilized CuI particles sufficient to remove the water. Another optional step is to neutralize the pH of the dispersion prior to the optional drying step.

In a further embodiment of the invention, metal compound particles may also be formed by grinding, particularly wet grinding. Wet grinding is carried out in liquid (aqueous or non aqueous), where the media further comprises any surface modifying agents.

A further embodiment of the invention is directed to a method of inhibiting the growth of microbes on the surface of an article of manufacture comprising coating the antimicrobial composition comprising CuI upon the surface in an amount effective to inhibit growth of a microbe.

A further embodiment of the invention is a method of inhibiting growth of a microbe comprising the steps of contacting the environs of a microbe with an effective amount of a composition comprising a particle comprising at least one inorganic copper salt having an average size of less than about 100 nm; and at least one functionalizing agent in contact with the particle, the functionalizing agent stabilizing the particle in solution such that an antimicrobially effective amount of ions are released into the environment of a microbe.

A further embodiment of the invention is directed to a composition having antimicrobial activity comprising a mixed-metal halide particle comprising at least one copper halide and at least a second metal halide; and at least one functionalizing agent in contact with the mixed-metal halide particle, the functionalizing agent stabilizing the particle in suspension such that an antimicrobially effective amount of ions are released into the environment of a microbe.

A further embodiment of the invention is directed to a composition having antimicrobial activity comprising a mixture of particles comprising particles of an inorganic copper salt and particles of at least a second inorganic metal compound; and at least one functionalizing agent in contact with said mixture of particles, said functionalizing agent stabilizing said mixture of particles in a carrier such that an antimicrobially effective amount of ions are released into the environment of the microbe. Preferably the size of such particles is less than about 300 nm.

A further embodiment of the invention is directed to a composition having antimicrobial activity made according to the process comprising the steps of forming stabilized copper iodide particles; dispersing the stabilized copper iodide particles in a suspending medium; adding a quantity of the dispersed copper iodide particles to a manufacturing precursor; and forming an article of manufacture at least partially from the manufacturing precursor whereby copper iodide particles are dispersed throughout said article. Preferably the size of such particles is less than 300 nm. In some cases, the article may be a coating which is applied to a separate article of manufacture to provide antimicrobial benefits.

A further embodiment of the invention is directed to a composition having antimicrobial activity comprising at least two antimicrobially active ingredients, wherein the first of said ingredients comprises a functionalized copper halide nanoparticle having an average size of less than 300 nm. The composition may also comprise at least one or more different metal or inorganic metal compound nanoparticles having antimicrobial activity. Further, the metal and inorganic metal compounds of the composition may further comprise metals selected from the group consisting of selenium, bismuth, silver, zinc, copper, gold and compounds thereof.

A further embodiment of the invention is directed to a composition having antimicrobial activity comprising a metal halide selected from the group consisting of copper halide and silver halide; and a porous carrier particle in which the metal halide is infused, the carrier particle supporting the metal halide such that an antimicrobially effective amount of ions are released into the environment of the microbe.

In another embodiment of the invention, the porous carrier particles containing copper halide or copper halide and silver halide may be incorporated in matrix materials used as coatings or solid bodies having desirable antimicrobial activity.

In a further embodiment of the invention, the present antimicrobial compositions, whether functionalized particles comprising copper halide nanoparticles or porous carrier particles containing copper halide or copper halide and silver halide nanoparticles, may be combined with polymer-containing coating solutions which may be applied by end users to obtain antimicrobial activity in the coated objects.

A further embodiment of the invention is directed to a composition having antimicrobial activity comprising a copper halide selected from the group consisting of copper iodide, copper bromide and copper chloride; and a porous carrier particle in which said copper halide is infused, said carrier particle supporting said copper halide such that an antimicrobially effective amount of ions are released into the environment of said microbe.

Yet a further embodiment of the invention is directed to an antimicrobial composition comprising one or more antibacterial materials and/or analgesics and further comprising particles of at least one metal halide, said particles having a preferred average size of less than about 1000 nm. At least one inorganic metal halide is selected from the group consisting of copper halide and silver halide, and the halides are selected from the group consisting of iodide, chloride and bromide. A preferred metal halide is copper iodide.

Other embodiment is directed to a composition having antimicrobial activity comprising a metal halide selected from the group consisting of copper halide and silver halide; and porous carrier particles in which said metal halide is infused, said carrier particles supporting said metal halide such that an antimicrobially effective amount of ions are released into the environment of said microbe. The composition may be incorporated into a product of manufacture so as to impart antimicrobial properties to said product by releasing antimicrobially effective amounts of ions into the environment of a microbe. In the said composition said porous carrier particles are selected from the group consisting of silica particles, porous polymeric resins, and ceramic particles. In the said composition said copper halide has a solubility of less than about 100 mg/liter in water, preferably less than about 15 mg/liter in water. In the said composition said copper halide preferably is CuI. The composition may additionally comprise a silver metal. In the said composition said silver halides preferably are selected from the group consisting of AgI, AgBr, and AgCl.

In another embodiment there is provided a composition having antimicrobial activity comprising: a copper halide; and porous carrier particles in which said copper halide is infused, said carrier particles supporting said copper halide such that an antimicrobially effective amount of ions are released into the environment of said microbe. Also provided is a composition having antimicrobial activity comprising a plurality of metal halides comprising copper halide and silver halide; and porous carrier particles in which said metal halides are infused, said carrier particles supporting said metal halides such that an antimicrobially effective amount of ions are released into the environment of said microbe. The aforesaid composition may be incorporated into a product of manufacture so as to impart antimicrobial properties to said product by releasing antimicrobially effective amounts of ions into the environment of a microbe. In such composition said porous carrier particles preferably are selected from the group consisting of silica particles, porous polymeric resins, and ceramic particles. In such composition said copper halide preferably has a solubility of less than about 100 mg/liter in water, more preferably less than about 15 mg/liter in water. In such composition said silver halides preferably are selected from the group consisting of AgI, AgBr, and AgCl. In such composition said copper halide preferably is copper iodide. In such composition the size of the porous particles preferably is below 100 μm in size, more preferably from about 0.5 to about 20 μm, even more preferably from about 2 to about 20nm, most preferably from about 4 to about 15nm. In such embodiment the surface area of the porous particles is greater than about 20m2/g, more preferably greater than about 100m2/g.

Another embodiment is directed to a composition having antimicrobial activity comprising:a mixture of particles comprising particles of an inorganic copper salt and particles of at least a second inorganic metal compound; and at least one functionalizing agent in contact with said mixture of particles, said functionalizing agent stabilizing said mixture of particles in a carrier such that an antimicrobially effective amount of ions are released into the environment of said microbe. In such embodiment said carrier is a liquid, and said functionalizing agent preferably is soluble in said liquid carrier. In such embodiment said particles are complexed by said functionalizing agent, and said liquid carrier preferably is water-based, is oil-based, or said particles are suspended by said liquid carrier in solution. In such embodiment said carrier is a solid, preferably a melt-blend plastic. In such embodiment said inorganic copper salt preferably comprises a copper halide salt. In such embodiment said second metal preferably is selected from the group consisting of Silver, Gold, Copper, Zinc and Bismuth or alloys thereof In such embodiment said second inorganic metal compound may be a metal halide salt wherein the halide is selected from the group consisting of Iodide Bromide and Chloride. In such embodiment said mixture of particles preferably has an average size range of from about 1000 nm to about 4 nm. In such embodiment said mixture of particles preferably has a solubility of less than about 100 ppm in water, more preferably less than about 15 ppm in water. In such embodiment said functionalizing agent preferably is selected from the group consisting of an amino acid, a thiol, a hydrophilic polymer, a hydrophobic polymer, a amphiphilic polymer, surfactants and a target-specific ligand, wherein said hydrophobic polymer preferably may be selected from the group consisting of polyurethanes, acrylic polymers, epoxies, silicones and fluorosilicones, said hydrophilic polymer preferably selected from the group consisting of polyvinylpyrrolidone, polyethyleneglycol and copolymers and blends comprising at least one of the monomers which form the polymers. In such embodiment said functionalizing agent preferabllexes said mixture of particles. In such embodiment said second inorganic metal compound preferably comprises silver. In such embodiment said functionalized mixture of particles releases copper and silver cations into the environment of a microbe, preferably copper and silver cations in an amount sufficient to inhibit the growth of or kill said microbes. In such embodiment said inorganic copper salts and said second inorganic metal compound particles are selected from the group consisting of CuI, CuBr, CuCl, AgI, AgBr and AgCl. The present invention also provides a composition having antimicrobial activity comprising: a mixture of particles comprising particles of a copper halide and particles of a silver halide; and at least one functionalizing agent in contact with said mixture of particles, said particles stabilizing said mixture of particles in a carrier such that an antimicrobially effective amount of ions are released into the environment of said microbe.

The invention also is directed to a composition having antimicrobial activity made according to the process comprisingCuI powder; dissolving said CuI powder in a polar nonaqueous solvent; adding an amount of functionalizing agent sufficient to stabilize said CuI in the polar, nonaqueous solvent; removing the solvent sufficient to dry said stabilized CuI particles whereby a functionalizing agent-complexed CuI particle powder is formed; dispersing the functionalizing agent-complexed CuI particle powder in an aqueous solution having a pH of from about 0.5 to about 6 to form CuI particles stabilized in water; and optionally drying said stabilized CuI particles sufficient to remove the water. In one embodiment of the invention said solvent is a polar aprotic solvent. In one embodiment of the invention said solvent is selected from the group consisting of acetonitrile and dimethylformamide. In such composition said functionalizing agent preferably is selected from the group consisting of amino acids, thiols, hydrophilic polymers, amphiphilic polymers and surfactants. In such composition said hydrophilic polymer preferably is selected from the group consisting of polyvinylpyrrolidone, polyethleneglycol and copolymers and blends comprising at least one of the monomers which form the said polymers. In such composition said functionalizing agent complexes said copper iodide particles. In such composition said functionalized copper iodide particles preferably release copper cations in an aqueous environment. In such composition said functionalized copper iodide particles preferably release copper cations in an amount sufficient to inhibit the growth of microbes. In such composition said functionalized copper iodide particles release copper cations in an amount sufficient to kill said microbes. In such composition said functionalized copper iodide particles preferably release iodide ions into the external environment of said microbes. In such composition said ratio of polymer to particle preferably is from about 0.5:1 to about 100:1 by weight. In such composition the functionalized particle preferably has an average size range of from about 1000 nm to about 4 nm. One embodiment additional cormprise the step of neutralizing said aqueous dispersion prior to the optional drying step.

In another embodiment of the invention there is provided a composition having antimicrobial activity made according to the process comprising the steps of: obtaining CuI powder; dissolving said CuI powder in a polar nonaqueous solvent; adding an amount of polymer comprising PEG and/or PVP and their blends and copolymers sufficient to stabilize said CuI in the polar, nonaqueous solvent; removing the solvent sufficiently to dry said stabilized CuI particles whereby a polymer-complexed CuI particle powder is formed; dispersing the polymer-complexed CuI particle powder in an aqueous solution having a pH of from about 0.5 to about 6 to from CuI particles stabilized in water whereby a polymer-complexed CuI particle; and optionally drying said stabilized CuI particles sufficient to remove the water. Another embodiment is directed to a composition having antimicrobial activity made according to the process comprising the steps of: obtaining a copper compound or a silver compound which is selected from the group consisting of a copper halide, silver halide, copper oxide, silver oxide and copper thiocyanate; grinding said compound in the presence of a functionalizing agent in a fluidic medium so as to surface functionalize the smaller particles being formed; obtaining said compound particles at least in a range of about 1,000 to 4nm; and optionally removing the fluid sufficient to dry said functionalized material particles. In one embodiment the halide preferably is CuI, CuBr, CuCl, AgBr, AgI and AgCl and the oxide is $Cu_2O$ and $Ag_2O$. In another embodiment said functionalizing agent preferably is selected from the group consisting of amino acids, thiols, hydrophilic polymers, hydrophobic polymers, amphiphilic polymers, monomers, surfactants and emulsions of hydrophobic polymers. In such embodiment the fluidic medium may be aqueous or nonaqueous. If desired said composition may be added to an article of manufacture to provide antimicrobial characteristics.

Another embodiment is directed to a composition having antimicrobial activity comprising; a mixed-metal halide particle comprising at least one copper halide and at least a second metal halide; at least one functionalizing agent in contact with said mixed-metal halide particle, said functionalizing agent stabilizing said particle in a carrier such that an antimicrobially effective amount of ions are released into the environment of a microbe. In one embodiment said carrier is a liquid, and said functionalizing agent preferably is soluble in said liquid carrier. In one embodiment said particles are complexed by said functionalizing agent, and said liquid carrier preferably is water-based, or oil-based. In one embodiment said particles are suspended by said liquid carrier in solution. In another embodiment said carrier may be a solid, preferably a melt-blend plastic. In one embodiment said halide is iodide. In one embodiment the composition comprises a mixed-metal halide particle having an average size range of from about 1000 nm to about 4 nm. In one embodiment the composition comprises a mixed-metal halide particle having a solubility of less than about 100 ppm in water, preferably less than about 15 ppm in water. In one embodiment said functionalizing agent preferably is selected from the group consisting of an amino acid, a thiol, a hydrophilic polymer, a hydrophobic polymer, an amphiphilic polymer, surfactants and a target-specific ligand. In such embodiment said hydrophilic polymer preferably is selected from the group consisting of polyvinylpyrrolidone, polyethyleneglycol and copolymers and blends comprising at least one of the monomers which form the said polymers. In one embodiment said functionalizing agent complexes said mixed-metal halide particle. In one embodiment said second metal comprises silver. In one embodiment said functionalized mixed-metal halide particle releases copper and silver cations into the environment of a microbe, preferably in an amount sufficient to inhibit the growth of or kill said microbes. In one embodiment said mixed-metal halides are selected from the group consisting of Cu—AgI, Cu—AgBr and Cu—AgCl. In such embodiment the weight ratio of Cu:Ag ranges preferably from about 10:90 to about 90:10.

Another embodiment is a composition having antimicrobial activity comprising: a mixed-metal halide particle comprising copper iodide and a silver halide; at least one functionalizing agent in contact with said mixed-metal halide particle, said functionalizing agent stabilizing said particle in a carrier such that an antimicrobially effective amount of copper and silver ions are released into the environment of a microbe.

Another embodiment is directed to a method of inhibiting growth of or killing microbes comprising the steps of contacting a microbial environment with an effective amount of a composition comprising: particles comprising at least one inorganic copper salt; at least one functionalizing agent in contact with said particles, said functionalizing agent stabilizing said particles in a carrier such that an antimicrobially effective amount of ions are released into the microbial environment. In such embodiment said carrier preferably is a liquid, and said functionalizing agent preferably is soluble in said liquid carrier. In such embodiment said particles are complexed by said functionalizing agent, and said liquid carrier preferably is water-based, or is oil-based, or said particles are suspended by said liquid carrier in solution. In another embodiment said carrier is a solid, preferably a melt-blend plastic. In such embodiment said inorganic copper salt preferably comprises a copper halide salt.

The invention also provides a method of contacting a microbial environment which comprises dispersing said composition in a monomer or polymer in an antimicrobially effective amount and then applying said monomer or polymer dispersion to a surface capable of being protected against the presence of microbes. In one embodiment contacting a microbial environment comprises dispersing said composition in a liquid in an antimicrobially effective amount, and then contacting a surface capable of being protected against the presence of microbes with said dispersion. In one embodiment said contacting a microbial environment comprises dispersing said composition in a melt-blend, extrudable or injection moldable polymer. In one embodiment the method further comprises the step of combining said dispersion with other melt-blend extrudable or injection moldable-capable polymers, and then manufacturing an article from said composition dispersed in said melt-blend, extrudable or injection-moldable polymer. In such method the composition preferably contains at least about 12 ppm of the antimicrobially-effective composition. In such method said halide preferably is Iodide. In such method said particles preferably have an average size range of from about 1000 nm to about 4 nm. In such method said inorganic copper salt preferably has a solubility of less than about 100 mg/liter in water, more preferably less than about 15 mg/liter in water. In such method said functionalizing agent preferably is selected from the group consisting of amino acids, thiols, hydrophilic polymers, hydrophobic polymers, amphiphilic polymers, surfactants and ligand-specific binding agents, more preferably an amino acid selected from any of aspartic acid, leucine and lysine, a thiol related selected from the group consisting of aminothiol, thioglycerol, thioglycine, thiolactic acid, thiomalic acid, thiooctic acid and thiosilane, a hydrophilic polymer selected from the group consisting of polyvinylpyrrolidone, polyethyleneglycol and copolymers and blends comprising at least one of the monomers which form the said polymers, or a hydrophobic polymer selected from the group consisting of polyurethanes, acrylic polymers, epoxies, silicones and fluorosilicones. In another embodiment said functionalizing agent complexes said copper halide salt.

Another embodiment is directed to a method of inhibiting growth of or killing microbes comprising the steps of contacting a microbial environment with an effective amount of a composition comprising: particles comprising at least one inorganic copper salt selected from the group consisting of CuI, CuBr and CuCl and having an average size of less than about 1000 nm; at least one functionalizing agent in contact with said particles, said functionalizing agent being present at a ratio of from about 100:1 to about 0.5:1.

Another embodiment of the invention is directed to a method of inhibiting growth of or killing bacteria comprising the steps of contacting a bacterial environment with an effective amount of a composition comprising: particles comprising at least one inorganic copper salt; at least one functionalizing agent in contact with said particles, said functionalizing agent stabilizing said particles in a carrier such that an antibacterially effective amount of ions are released into the bacterial environment.

BRIEF DESCRIPTION OF THE DRAWINGS

FIG. 1 is a bar chart showing the growth and/or inhibition of *Bacillus cereus* spores when treated with various combinations of functionalized nanoparticles of the invention.

FIG. 2 is a bar chart showing the effectiveness of CuI against the growth of *Bacillus cereus* spores.

2. Defined Terms

Figure 3:
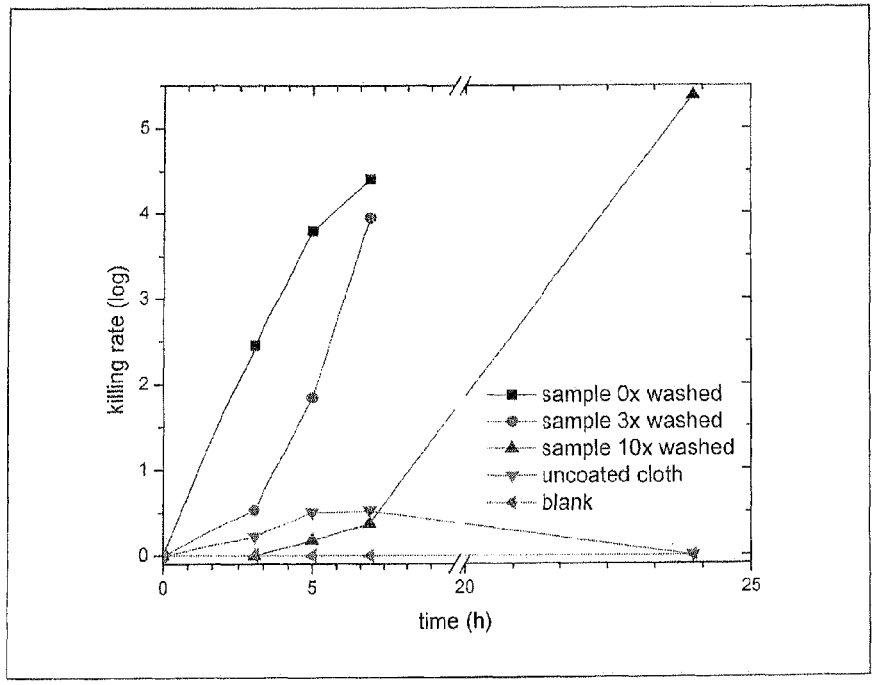
FIG. 3 is a plot of kill rate ($Log_{10}$ reduction) of *Pseudomonas aerugin agents may include polyurethanes and water soluble polymers such as polyvinylpyrrolidone (PVP) and polyethylene glycol (PEG), which stabilize CuI nanoparticles, facilitate dissolution in paints, and also helps adherence to the external microbial surfaces thereby bringing the copper ions into close proximity to their target. Functionalization agents may also include hydrophobic polymers which are used as emulsions and solutions to modify the particulate surfaces. Both of these factors, the nature of the metal halide and the qualities of the functionalizing agent, are material to the overall efficacy of the antimicrobial composition.

The term "amino acids" includes any of the twenty naturally-occurring amino acids known to be critical to human health, but also any non-standard amino acids. An amino acid is conventionally defined as $H_2NCHRCOOH$ where the R group may be any organic substituent. Preferred embodiments of the current invention include a subset including aspartic acid, leucine and lysine which have demonstrated utility in stabilizing the particles in a carrier, although other amino acids may have also have utility as functionalizing agents.

The term "amount of functionalizing agent sufficient to stabilize a metal salt in the solvent" refers to the amount, on a weight-to-weight basis, of any suitable polymer mentioned herein capable of holding in suspension a metal salt in an aqueous or nonaqueous environment so that the metal salt will not settle out of solution (in the case of a liquid composition including monomeric compositions) or more viscous media (such as an ointment, cream, or polymer).

The term "amount sufficient to inhibit the growth of microbes" in one embodiment is determined by the effect upon a microbe's growth as tested in an assay. The growth-inhibiting amount will vary depending upon the type of metal salt, the precise functionalizing agent, the concentration of the salt in the functionalizing agent, the size of the salt particles, the salt's aqueous solubility, the pH, the genus and species of the bacterium, fungus, spore or other pathogen, etc. One conventional measure is the Minimum Inhibitory Concentration (or $MIC_{50}$) of an agent required to inhibit the growth of 50% of the starting population. The related term "minimum amount sufficient to kill a microbe" is also determined empirically. A conventional measurement is the Minimum Bactericidal Concentration to kill 50%, or $MBC_{50}$. The antimicrobial effectiveness can also be evaluated by measuring the decrease in microbial populations as a function of time or by measuring the change in optical density of microbial populations exposed to the antimicrobial agents to vs. without such exposure.

The term "amphiphilic polymers" is directed to water-soluble polymers that have both hydrophilic and hydrophobic moieties which makes them capable of solvating the two disparate phases. Some examples of amphiphilic polymers include but are not limited to block copolymers, including those block copolymers where at least one block is selected from the hydrophilic polymer list, and at least one block may be selected from the list of the hydrophobic polymer list. Other examples are PVP-block-polypropyleneoxide-block; polyethyleneoxide-block-polypropyleneoxide-block-polyethyleneoxide-block; polyethyleneoxide-block-polypropylene oxide-block.

Monomers include those materials which have the ability to attach to the surfaces of the particles and also react or bond with matrices in which such modified particles are introduced into. A "matrix material" is a polymer to which this monomer would bind to by reaction or by physical association such as complexation. Some examples of monomers are polyolys, silanes, metal alkoxides, acrylic polyols, methacrylic polyols, glycidyl esters, acrylics and methacrylics.

The term "an average size of less than about XX nm", where "XX" is a variable for the number of nanometers, is defined herein as the average particle size, as measured by any conventional means such as dynamic light scattering or microscopy, of a sampling of particles wherein the average is less than about XX nanometers in diameter, assuming for purposes of the calculation that the irregular particles have an approximate diameter, that is, that they are approximately spherical. This assumption is purely for the calculation of average particle size, due to the particles often being non-spherical in shape. Methods used to measure particle size include dynamic light scattering, scanning electron microscopy or transmission electron microscopy. Embodiments of the present invention have demonstrated a range of average particle sizes from about 1000 nm to about 4 nm, including average particle sizes of less than about 1,000 nm, less than about 300 nm, less than about 100 nm, less than about 30 nm, and less than about 10 nm. Smaller particle sizes in general may be preferred for certain applications, but the average size relates to the release rate characteristics of the ions from the particles, so particle size and release rate are interdependent. Embodiments of the invention may also be made in other shapes, for example sheets or rods where some of the dimensions may be several microns, in which case the average size of such objects would be measured in relation to their smallest dimension being less than about 1000 nm, 300 nm, 100 nm, 30 nm and less than 10 nm. In the case of a fiber, the smallest dimension is its cross-section diameter; in the case of a sheet it is usually its thickness.

The term "anti-bacterial effect" means the killing of, or inhibition or stoppage of the growth and/or reproduction of bacteria.

The term "anti-fungal effect" means the killing of, or inhibition or stoppage of the growth and/or reproduction of molds and/or fungi.

The term "antimicrobial effect" is broadly construed to mean inhibition or stoppage of the normal metabolic processes required for continued life, or continued growth of any of the microorganisms in the classes of bacteria, viruses, mold, fungus or spores. "Antimicrobial effect" includes killing of any individual or group of bacteria, viruses, mold, fungus or spores.

An "antimierobially effective amount" of any agent mentioned herein as having an antimicrobial effect is a concentration of the agent sufficient to inhibit the normal cellular processes including maintenance and growth of a bacterium, virus, mold, fungus, spore, biofilm or other pathogenic species. Antimicrobially effective amounts are measured herein by use of assays that measure the reduction in growth or decline in their populations of a microbe. One measure of reduction is to express the decrease in population in logarithmic scale typical of a specific microbial species. That is, a 1 log reduction is equivalent to a 90% reduction versus a control, a 2 log reduction is a 99% reduction, etc.

The term "anti-spore effect" means the killing of, or inhibition or stoppage of the growth and/or reproduction of spores.

The term "anti-viral effect" means the killing of, or inhibition or stoppage of the growth and/or reproduction of viruses.

The term "carrier" as used herein is a medium for containing and applying the functionalized inorganic metal salt particles so that they may be incorporated into surfaces so that ions from the metal salts will become available to contact and thereby kill or inhibit microbes that may be or become present on the surface. A carrier may be a liquid carrier, a semi-liquid carrier, or a solid carrier, or it may change states during the processes of dissolution and application. For purposes of exemplification, in the case of a liquid carrier such as an aqueous liquid, a dry powder comprising metal halide particles functionalized with a polymer such as PVP may be added to the water and will dissolve or disperse in the carrier due to the physical and/or chemical characteristics of the PVP, such that the particle-PVP complex is dispersed uniformly. The water carrier may then be evaporated from the surface to which it was applied, leaving a uniform layer of particle-PVP from which ions may be made available to the surface over time. The same considerations apply where additional additives may be added to the carrier, e.g., polymer emulsions, where upon evaporation of carrier (water), a film is formed of this polymer comprising well dispersed functionalized metal salt particles. As an example, many acrylic and urethane polymeric aqueous emulsions are used for a variety of coating applications such as furniture and trim varnishes, floor finishes and paints. These typically comprise of surfactants to disperse the hydrophobic polymers in the aqueous media. Functionalized metal salt particles may be added to these, or they are formed or reduced in size within these emulsions so that the content of the emulsions functionalize the particles as they are formed. The functionalization materials along with the shape and other characteristics of the antimicrobial material (metal salts) may impart a leafing property, which means as the carrier in these coatings dries out, surface tension causes these particles to rise to the surface thus naturally providing a higher concentration of antimicrobial material on the surface of such coatings Similar relevancy applies to a hydrophobic liquid carrier such as an oil-based paint or an epoxy resin. Carriers may be a monomer, or may be optionally supplemented with a monomer that is added into the mix of the removable carrier and functionalized particles, and then during processing the monomer polymerizes (with or without crosslinking) which may be accompanied by the evaporation of the carrier if present to form a polymerized product with functionalized particles dispersed therein. In the case of a solid carrier such as when incorporating functionalized particles in a solid plastic, the same dry powder particle-PVP complex can be added to plastic powders or pellets, and then the plastic is brought to a molten state, where all the components are mixed (or melt blended). The surface functionalization of the particles facilitates one or more of several desirable attributes, such as more uniform dispersion of the particles (less agglomeration); better adhesion of the particles to the plastic so as to not compromise physical properties of the plastic or the product made from it; and provide a pathway for the ions from the metal salt to be released and travel to the surfaces where microbes may be present. In this case the carrier or the plastic does not evaporate but is an integral part of the final product after it changes its state from a liquid to a solid. Some solid plastic materials derive their properties by being multiphasic (having two or more phases). For example, polymer blends and alloys of two different polymers, or block and graft polymers in solid state typically form multiple phases to derive their unique physical and chemical properties. When such multiphasic plastics are used, the functionalization of the functionalized particles may be so tailored that it is more compatible with one of these phases and thus distributes the particles preferentially in that phase, or may be tailored to preferentially position the particles at the interphase area of these phases.

A "copper halide salt" is a member of the copper metal family combined with any of the halides, typically defined in the Periodic Table of the Elements as fluorine, chlorine, bromine and iodine. Of these, preferred embodiments of the invention commonly include iodide, bromide and chloride. Copper halide salts may include both copper (I) and (II) varieties, for example Cu(I)Cl and Cu(II)Cl$_2$.

The term "emulsion" refers to those stabilized fluid suspensions or polymeric latex fluids, where in a fluid, particles or droplets of an incompatible material are stabilized through the use of surfactants.

The term "environs of a microbe" is any 1) surface actually or capable of being inhabited by a microbe that may thereafter be contacted by a human, or 2) in the case of an aerosol, any liquid droplet that may now or in the future contain a microbe whether on a surface or suspended in air, or 3) in the case of a water-borne microbe any body of liquid that may carry a microbe now or in the future.

The terms "external environment of a microbe" and "internal environment of a microbe" refer to the immediate environment external to the microbe, that is, the liquid, gel or solid the microbe inhabits, and the internal volume of a microbe, respectively. The external environment of a microbe is often that of a liquid (usually aqueous) in order for the microbe to live, and for the antimicrobial metal salt or its constituent ions to be communicated to the microbe. The external environment does not need to be liquid, however, but must provide for the transmission of the antimicrobial agent to come into proximity of the microbe, where it can then be taken up by any of several different mechanisms.

The term "functionalization" means modification of the surface chemistry of the particles to effectuate any one or more of the following: 1) improve their interaction with other materials, especially with microbial species and 2) to improve their interaction and uniformity of distribution with constituents of coatings and bulk materials, and 3) to provide increased stability for the particles dispersed in liquid suspension. The term "functionalizing agent" may include in a first embodiment a variety of polymeric species, such as polyvinyl pyrrolidone (PVP), polyethylene glycol (PEG), polyurethane polymers, acrylic polymers, or polymers with ionic moieties. The functionalization agents may also play additional roles, they may modify the pH of the solution and hence bind differently to the particles, or they may act as reducing agents as in the case of PVP. The polymers may be hydrophilic or hydrophobic. Functionalization may also be carried out in a second embodiment using small molecule (non-polymeric) species such as amino acids (or combinations of amino acids), peptides and polypeptides. In a third embodiment thiols (or combinations of thiols) also have demonstrated utility. Other embodiments include carbohydrates, glycols, esters, silanes, surfactants, monomers and their combinations. In yet another embodiment functionalization may refer to adding a ligand or group of ligands to the particle so that it specifically binds to a receptor or other biological target on a microbe. One may also use combinations of the above functionalizing agents in the same functionalizing formulation to effect a targeted approach for specific genus and species of microbes.

The term "hydrophilic polymer" refers to water-soluble polymers having an affinity or ability to complex the nanoparticles of copper salts shown herein. Examples of functionalizing agent compositions include, but are not limited to, polyurethanes, including polyether polyurethanes, polyester polyurethanes, polyurethaneureas, and their copolymers; polyvinylpyrrolidones and their copolymers (e.g., with vinyl acetate and/or caprolactum); polyvinyl alcohols; polyethyleneoxide, polyethylene glycols and their copolymers; polypropylene glycols and their copolymers; polyethyleneimine, polyoxyethylenes and their copolymers; polyacrylic acid; polyacrylamide; poly(diallyldimethylammonium)

chloride, carboxymethyl cellulose; cellulose and its derivatives; dextrans and other polysaccharides; starches; guar; xantham and other gums and thickeners; collagen; gelatins; boric acid ester of glycerin and other biological polymers. Particular embodiments of hydrophilic polymers include polyvinyl pyrrolidone, polyethyleneglycol and copolymers and blends comprising at least one of the monomers which form the aforementioned polymers.

The term "hydrophobic polymers" refers to water-soluble polymers similarly having an affinity or ability to complex the nanoparticles of copper salts shown herein, but being having a hydrophobic nature. Some examples of hydrophobic polymers include but are not limited to polytetrafluoroethylene, polyvinylchloride, polyvinylacetate, cellulose acetate, poly (ethylene terephthalate), silicone, polyesters, polyamides, polyurethanes, polyurethaneureas, styrene block copolymers, polyoxymethylene, polymethyl methacrylate, polyacrylates, acrylic-butadiene-styrene copolymers, polyethylene, polystyrene, polypropylene, polypropylene oxide, polyisoprene, acrylonitrile rubber, epoxies, polyester epoxies, and mixtures, or copolymers thereof.

The term "inorganic copper salt" includes relatively water insoluble, inorganic copper compounds. Inorganic copper salt is an ionic copper compound where copper cations along with anions of other inorganic materials form this compound. Typically these compounds release copper ions ($Cu^+$ or $Cu^{++}$) when such salt is put in proximity to water. Those copper salts are preferred that have low water solubility, i.e., solubility lower than 100 mg/liter and preferably less than 15 mg/liter. Some of the preferred copper salts are cuprous halides, cuprous oxide and cuprous thiocyanate.

The term "polar aprotic solvent" includes those liquids having a dielectric constant greater than about 15 that have no labile protons, non-limiting examples including acetone, acetonitrile, dimethylformamide and dimethylsulfoxide.

The term "polar nonaqueous solvent" includes those liquids (except for water) having a dielectric constant greater than about 15. Non-limiting examples include alcohols such as methanol, ethanol, butanol and propanol, and acids such as formic acid.

The term "releases copper cations" generally refers to the making available of copper cations in the immediate environment of a microbe from the metal salt held in suspension by the functionalizing agent. The release mechanism is not a controlling feature of the invention. In one embodiment, release may occur by dissolution of copper ions from a copper halide particle, for example. In another embodiment, release may be mediated by a functionalizing agent such as PVP which complexes the copper cation until the PVP contacts a microbe thereby transferring the cation to the external environment of the microbe. Any number of mechanisms could account for the release of the copper cations, and the invention is not to be restricted to any mechanism. Also of potential for antimicrobial effect is the release of anions from the copper halide particles, for example triiodide anion ($I_3^-$) is a known antimicrobial agent.

The term "stabilizing said particle in a carrier" means to maintain the functionalized particle dispersed and separate from other particles in the liquid carrier such that agglomeration and/or settling out of suspension is inhibited. The stability of a dispersion is measured according to its "shelf life," or time period over which there is no appreciable settling out of suspension of the dispersed element. Stabilized particles have a longer shelf life as compared to particles of similar shape and size which are not stabilized. Typically for similar particles in similar solvents stabilized with similar materials used at concentrations proportional to the surface area of the particles, the shelf life of larger particles may be lower than the shelf life of the smaller particles. It should be noted that in some cases a few large particles are formed which may settle fast, however as long as appreciable amounts (greater than 25%) by volume or by weight of the particles remain dispersed, that would still be a stable dispersion. Shelf lives preferably of at least eight hours, more preferably at least 30 days, and most preferably at least 180 days are contemplated for the compounds and particles of the invention hereunder. The term "dispersion" is distinguishable from a "suspension" in that a dispersion does not imply any permanence to the suspension.

The dispersions or liquid suspensions may be intermediate products or may be the end products in which the antimicrobial materials are used. Examples are low viscosity liquids such as those used for liquid sprays to treat surfaces suspected of having a microbial problem in a specific area, or the low viscosity liquids may be used as intermediates to be added to paint formulations to make them antimicrobial. The inorganic metal salt nanoparticles of the current invention may also be used in high viscosity liquid suspensions such as creams for topical use. In end-use products higher suspension stability is preferred and in intermediates, the stability has to be sufficient for the process in which this intermediate is used. The terms "dispersion" and "suspension" are used interchangeably throughout this specification.

The term "surfactants" means nonionic, cationic, anionic or amphoteric surfactants, some specific examples are Brij, Tween, Triton X-100, Sodium dodecyl sulfate (SDS), cetyltrimethylammonium chloride or cetyltrimethylammonium bromide. A large variety of surfactants are commercially available. So long as the surfactant stabilizes the particles of the invention, it falls within the spirit and scope of the claims.

The term "thiol" generally refers to a chemical having an —SH substituent. Embodiments of the invention include thiols such as aminothiol, thioglycerol, thioglycine, thiolactic acid, thiomalic acid, thiooctic acid and thiosilane. Other thiols may also have utility in the current invention. Other thiols useful in the invention will be water soluble and have the capability of complexing metal halides and holding them in suspension in an aqueous environment.

3. The Compositions a. Oligodynamic Metals

In one embodiment of the invention, the preferred material compositions comprise at least one metal halide and the combination of one or more metals with at least one metal halide. Presently preferred metals are copper, zinc, silver and their alloys and also their halides, including those mixed halides formed simultaneously from more than one element. Compositions may include alloys comprising at least one of silver, copper and zinc. Example of these alloys are those of silver+copper, copper+tin (bronze) and copper+zinc (brass is an alloy of copper and zinc with typical copper concentrations in the range of 40 to 90% by weight, and may have additional elements, e.g., as in phosphor bronze). These alloys may provide better stability of particles in the processing or in end use applications against oxidation or non-desirable surface reactions. Some other exemplary metal halides are germanium (II) iodide, germanium(IV) iodide, Tin(II) iodide, tin (IV) iodide), platinum(II)iodide, platinum(IV) iodide, Bismuth(III)iodide, Gold(I)iodide, Gold(III)iodide, Iron(II) iodide), cobalt(II)iodide), Nickel(II)iodide, Zinc(II)iodide, indium(III)iodide). The particles of this invention may also be fabricated in a core-shell geometry, wherein the core may be a solid support for a coating comprising the desirable materials as described above. As examples, core materials may be selected from silica, titania and carbon, or the cores may be porous. Preferred functionalized particles and combinations of particles of particular interest are silver halides and copper halides.

b. Copper Salts

The inorganic copper salt embodiments of the present invention include conventional inorganic copper salts, with limited water solubility. By way of exemplification the following inorganic copper compounds are illustrative but not limiting: Copper(II)iodate; Copper(I)iodide; Copper(I)chloride; Copper(I)bromide; Copper(I)oxide; Copper(I)acetate; Copper(I)sulfide; and Copper(I)thiocyanate.

The inorganic copper salts may have a range of water solubility characteristics. However, it is preferred that the copper salts of the present invention have low water solubility (or water insoluble salts with solubility less than 1 g/liter of water at room temperature) so that they may have slow and predictable copper cation release characteristics. In some formulations it may be desirable to also add Cu(II) or more soluble salts so that some fraction of Cu ions are instantly available. Cu(I) cations have shown the most efficacy against the various microbes tested. At room temperature, copper(I) salt solubilities of less than about 100 mg/liter are preferred, and more preferred are copper salts having less than about 15 mg/liter.

Other embodiments of copper (I) salts that may be useful in the present invention include halides where some of the copper has been substituted with other cations which may be other metals (forming mixed halide materials), or a given halide may be substituted with other anions. Alternatively, the substitution may be organic in nature, Examples of such substitutions include e.g., $AgCuI_2$, $CH_3NCuI_2$, $Rb_3Cu_7Cl_{10}$, $RbCu_3Cl_4$, $CsCu_9I_{10}$, $CsCu_9Br_{10}$, $Rb_4Cu_{16}I_7Cl_{13}$ and $RbCu_4Cl_3I_2$. In general one may express these copper salts as $P_sCu_tX_{(s+t)}$, where P is the organic or a metal cation and X is a halide, preferably selected from one or more of Cl, Br and I.

c. Copper Halides

Copper iodide (CuI), like most "binary" (containing only two elements) metal halides, is an inorganic material and forms a zinc blende crystal lattice structure. It can be formed from a simple substitution reaction in water with copper (II) acetate and sodium or potassium iodide. The product, CuI, simply precipitates out of solution since it is sparingly soluble (0.020 mg/100 mL at 20° C.) in water. Copper iodide powder can be purchased in bulk from numerous vendors. A grade with over 98% purity is particularly preferred.

Copper bromide (CuBr) is also an inorganic material having the same crystal structure as CuI. It is commonly prepared by the reduction of cupric salts with sulfite in the presence of bromide. For example, the reduction of copper(II) bromide with sulfite yields copper(I) bromide and hydrogen bromide. CuBr is also very slightly soluble in water.

Copper chloride shares the same crystal structure with CuBr and CuI and has a solubility of 62 mg/100 mL. It can be made by the reaction of mercury(II) chloride and copper metal.

Copper(I) fluoride disproportionates immediately into Cu(II) fluoride unless it is stabilized by complexation, so CuF is not a very useful copper halide particle source. Cu(II) fluoride is soluble in water and so it is not a source of $Cu^{2+}$ cations, but is a source of $Cu^{2+}$ cations.

d. Mixed-Metal Halides

Further embodiments of the invention are directed to mixed-metal halides resultant from combinations of metal salts of which at least one element is an oligodynamic metal. Such embodiments include silver-copper halide, silver-zinc halide, copper-zinc halide, etc. Preferred embodiments include silver-copper halides. Embodiments may include halogens such as Iodide, Bromide and Chloride. A particularly preferred embodiment is Iodide.

A general procedure for synthesizing silver-copper-iodide ($Ag_{1-x}Cu_xI$) nanoparticles using silver nitrate, copper nitrate, potassium iodide, and polyvinylpyrrolidone (PVP) as the functionalizing agent follows. This method results in solid solutions, meaning not separate distinct phases of CuI and AgI but where one metal is substituted for the other randomly: $(1-x)AgNO_3+xCu(NO_3)_2+KI \rightarrow Ag_{1-x}Cu_xI$. The x coefficient was varied to change the silver to copper ratio. The PVP concentration, which is known to stabilize the nanoparticles, was varied for x=0.5 ($Ag_5Cu_5I$).

Figure 5:
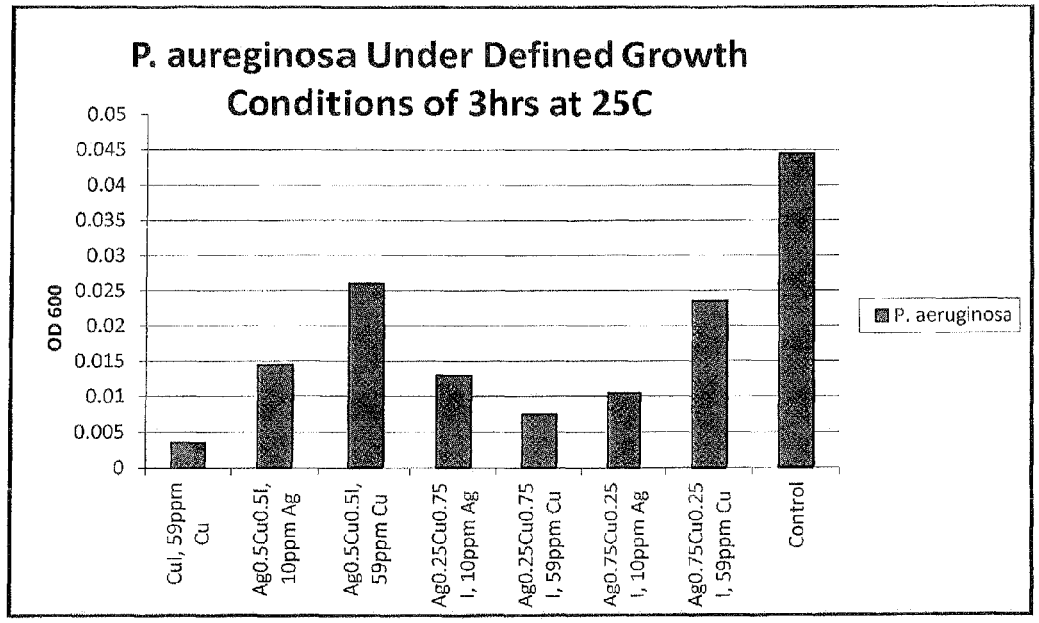
Figure 6:
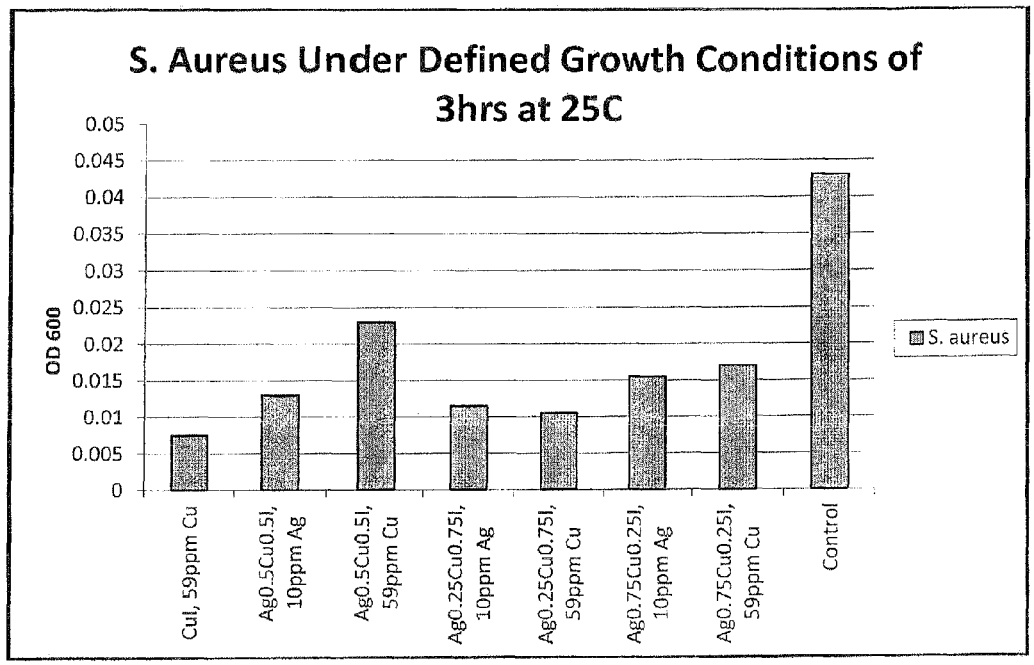

Silver-copper-bromide nanoparticles were synthesized following the same procedure as for silver-copper-iodide using KBr instead of KI. Silver-copper-iodide-bromide nanoparticles were prepared in the same fashion using a combination of KI and KBr in a (1−y):(y) mole ratio. Antimicrobial activity was determined for $Ag_{1-x}Cu_xI$ (x=0.25, 0.50, 0.75) by measuring optical density at 600 nm after 3 hours at 25° C. for *P. aureginosa* and *S. aureus*. Results are shown in FIGS. 5 and 6 discussed under the Experimental section.

e. Mixtures of Particles

In other embodiments the functionalized particles comprise mixtures or combinations of functionalized inorganic salts of metals such as silver or copper. The functionalized particles comprise halides of other oligodynamic metals, in some cases combined with functionalized particles of silver metals and/or copper halides or silver metal or copper metal. In a further embodiment, the functionalized particles comprise compounds of silver and copper other than their halides. In a further embodiment, these compositions, particularly compositions comprising copper halides especially copper iodide may be combined with other known antimicrobial or antifungal agents. One may also combine particles of different sizes/composition/solubilities to control the delivery rate and the longevity of the antimicrobial efficacy of the products where such particles are incorporated into. As an example, one may combine particles about 300 nm in size with those that are less than 30 nm, or one may combine particles larger than 300 nm in size with those that are smaller than 300 nm, etc. In applications such as those where copper or other compounds are used for antimicrobial effects, one may combine those with materials of this invention. As a specific example in marine coatings where zinc pyrithione, cuprous oxide or copper thiocyanate may be used for antimicrobial properties, one may combine those with the same composition (e.g., cuprous oxide and copper thiocyanate) but with size smaller than 300 nm and/or functionalized nanoparticles as taught in this invention. As another specific example these materials may be combined with copper iodide as taught in this invention.

Embodiments of the mixture of particles are directed to a composition having antimicrobial activity comprising (a) a mixture of particles comprising particles of an inorganic copper salt and particles of at least a second inorganic metal compound or metal; and (b) at least one functionalizing agent in contact with the mixture of particles, the functionalizing agent stabilizing the mixture of particles in a carrier such that an antimicrobially effective amount of ions are released into the environment of the microbe. A further embodiment of the inorganic copper salt comprises a copper halide salt. Yet a further embodiment of the invention includes the second metal being selected from the group consisting of silver, gold, copper, zinc and bismuth or alloys thereof. Yet a further embodiment of the invention comprises a second inorganic metal compound being a metal halide salt wherein the halide is selected from the group consisting of iodide, bromide and chloride. Yet a further embodiment of the invention includes the previous composition wherein the mixture of particles has an average size of less than about 100 nm, less than about 30 nm, or less than about 10 nm. Further embodiments of the invention include where the mixture of particles has a solubility of less than about 100 ppm in water, or less than about 15 ppm in water. Embodiments of the invention are also directed to functionalizing agents selected from the group consisting of an amino acid, a thiol, a hydrophilic polymer and a target-specific ligand. Another embodiment of the invention is directed to the previous composition wherein the second inorganic metal compound comprises silver. A further embodiment of the invention is directed to the previous composition wherein the functionalized mixture of particles releases copper and silver cations into the environment of a microbe. Embodiments of the invention are also directed to compositions wherein the functionalized mixture of particles releases copper and silver cations in an amount sufficient to inhibit the growth of or kill the microbes.

Further embodiments of the invention are directed to compositions wherein the inorganic copper salts and a second inorganic metal compound particles are selected from the group consisting of CuI, CuBr, CuCl, AgI, AgBr and AgCl.

For many applications cost is an important issue. Addition of precious metals or their salts to the compositions of this invention could make antimicrobial materials less attractive economically. As the copper halides of this invention have shown high efficacy against a variety of microbes and are less costly than their cousins the silver halides, thus for many applications mixing copper halides with silver, gold, platinum or other precious metals and their salts is not necessary. If needed for specific applications, the precious metals and their salts may be utilized in much lower concentrations.

f. Functionalizing Agents

An embodiment of the present invention is the "functionalization" of the metal salt particles. In functionalizing the surfaces of the particles of oligodynamic metals and their compounds or salts, a number of chemical species may effectively be used, which may be selected from one or more of the categories below. These functionalization agents are preferably present while the particles are being formed, either during chemical synthesis, or during physical grinding when they are being ground to a finer size from larger particles. The amount of surface functionalization agent increases with decreasing particle size in proportion to the overall change in surface area exposed for functionalizing. Any ratio of the relative amounts of the metal salt particles and the functionalization material may be used, typically these are present in a molar ratio (metal salt:functionalization agent) in a range of about 1:0.5 to about 1:100. For polymeric functionalization agents, the molarity is calculated based on their repeat units.

Surface functionalization typically imparts one or more of many attributes, such as preventing particles from agglomeration (e.g., promoting suspension stability, particularly in liquid products), enabling particles to attach to various surfaces of an object or even to the microbes, and assisting particles to attach to matrix materials when these are incorporated as composites into other materials. This functionalization also helps to disperse the antimicrobial particles easily into these matrices (e.g., blending with thermoset or thermoplastic polymers which are later molded into objects). An advantage of using finer particles as long as they are well dispersed in liquids or solids (including coatings) is that at even lower use concentrations the distance between particles is small. This results in better surface coverage of articles by such antimicrobial materials, and also increases their efficacy as there is more surface area of these materials available to interact with the microbes. For particles that are a few nanometers in size, the surface functionalization can also influence their transportation into the interior of the microbes. Functionalizing agents that may facilitate transport of nanoparticles to the surface of a microbe include amino acids and combinations of amino acids, peptides and polypeptides. Using these species as the functionalizing agents, it was found that when certain embodiments of amino acids are used to functionalize the surfaces of the oligodynamic metal-containing nanoparticles, enhanced antimicrobial activity was obtained. Amino acids which are particularly preferred as amino acid functionalizing agents for the present nanoparticles include aspartic acid, leucine and lysine, although numerous other amino acids may have efficacy. Potentially useful are combinations of amino acids as well as peptides, dipeptides, tripeptides and polypeptides of amino acids. Other embodiments of functionalizing agents include carbohydrates such as mono- and di-saccharides and their derivatives, glycol and alcoholic esters (e.g., Schercemol™ and Hydramol™ esters from Lubrizol (Wickliffe, Ohio)).

Other embodiments of the invention are directed to various polymers that may be used for functionalization. Typically the functionalization procedure is done in a medium in which these polymers are present in a solution and/or an emulsion form. Polyvinylpyrollidone and its copolymers are one embodiment that can be an effective agent for modifying the surface chemistry of tailored particles and imbuing them with desirable antimicrobial activity. Examples of other polymeric surface modifiers are polyacrylic acid, copolymers comprising acrylic (including methacrylic acid) groups, polyethylene and polypropylene glycols (and their copolymers), polymers with alcoholic groups, urethanes, epoxies and carbohydrate polymers. Each of the above polymers may have a range of molecular weights, typically in the range of about 1,500 and 2,000,000 Daltons, although molecular weights less than 500,000 are preferred, and molecular weights less than 25,000 are most preferred. Solubility and solution viscosity of the polymer generally correlates to average molecular weight with high weights being less soluble in water and resulting in more viscous solutions.

Another embodiment of functionalizing agents includes thiol functionalizing agents in addition to the amino acid or polyvinylpyrrolidone. Thiol modifying agents useful for functionalizing the antimicrobial nanoparticles include aminothiol, thioglycerol, thioglycine, thiolactic acid, thiomalic acid, thiooctic acid and thiosilane. Combinations of thiol modifying agents can also be used in the present invention. The functionalization of the particles may also provide additional attributes desirable for using them in practical applications. These attributes include the promotion of adhesion and/or reaction of the particles to specific matrices such as in bulk materials and coatings and the enhancement of their antimicrobial properties by making the interaction between particles and microbes more attractive or by coupling or combining them with other materials for specific applications. Examples of other materials with which the present antimicrobial particles can be combined include antimicrobial agents which target a specific microbe or group of microbes, or materials that under illumination or humid conditions provide modified antimicrobial activity, or materials that under anerobic conditions exhibit decreased antimicrobial activity for their safe disposal in landfills. Examples of coupling agents and monomers for increasing their compatibility with various polymeric matrices include organosilanes (e.g., epoxy silanes for use in epoxy matrices, mercapto silanes for use in urethane and nylon matrices, acrylic, methacrylic and vinyl silanes for use in reactive polyester and acrylic polymers). Other monomers include those materials which have the ability to attach to the surfaces of the particles and also react or bond with matrices in which such modified particles are introduced into. Some examples are polyolys, silanes, metal alkoxides, acrylic polyols, methacrylic polyols, glycidyl ester acrylics and methacrylics.

Embodiments of the invention also make use of surfactants for surface modification. The term surfactants would mean nonionic, cationic, anionic and amphoteric surfactants, some specific examples being Brij, Tween, Triton X-100, Sodium dodecyl sulfate (SDS), cetyltrimethylammonium chloride or cetyltrimethylammonium bromide (all available from Sigma-Aldrich Co, Milwaukee, Wis.).

One may also use surfactants (includes emulsifiers) to form emulsions (includes latex) of polymers and other materials, wherein such emulsions are used to modify the surfaces of the particles. For this purpose the polymers may be hydrophobic. Some examples are polyurethane emulsions, acrylic emulsions, fluorosilicone emulsions, epoxy emulsions, etc.

Another embodiment of a functionalizing agent is a ligand-specific binding agent. As a specific example, it has been demonstrated (Corinne K. Cusumano, et al., Sci Transl Med 3, 109ra115 (2010 (DOI: 10.1126/scitranslmed.3003021 "Treatment and Prevention of Urinary Tract Infection with Orally Active FimH Inhibitors") that mannoside compounds are effective in preventing uropathogenic E. coli infection in women by inhibiting the bacteria's ability to bind to epithelial cells of the bladder via FimH receptors. Since it has been demonstrated that mannoside compounds inhibit binding of E. coli to uroepithelial cells by binding FimH receptors, one may use such compounds to modify the surfaces of particles of this invention to specifically target E. coli. In one embodiment the mannoside compounds could be included in a functionalization formulation for the metal salt nanoparticles of the invention. In another embodiment mannoside compounds could be included within the coatings used in urinary tract catheters which would locally release the inorganic metal salt compounds to specifically target the particles to E. coli or any number of other pathogens for which a specific ligand-based approach is desired. There are numerous examples of other pathogenic infections which are specific to different parts of the body and tailored chemistries may be desirable to modify the particles/and or the matrices where particles of this invention are present. One of ordinary skill will be able to identify the various ligand-target combinations to design any manner of ligand-specific targeting approach for the particles of the present invention.

Other embodiments of the invention include affinity-based targeting mechanisms such as using certain inherent properties of microbes' external structures to target the metal halide nanoparticles to. For example, the peptidoglycan layer of Gram-positive bacteria is a polymer of sugars and peptides and has a generally negative charge. Other polymers, such as PVP or PEG may be attracted to the peptidoglycan surface on the basis of hydrophobic interactions, and once there, may stick to and deliver the stabilized metal halide particles as they slowly dissolve. Likewise, Mannose-binding lectin (MBL) and/or Lipopolysaccharide binding protein (LBP) may be included as functionalizing agents. MBL recognizes certain carbohydrate patterns on microbial surfaces and LBP binds to Lipopolysaccharide, which comprises a majority of the outer membrane of Gram-negative bacteria.

g. Porous Particles

Other embodiments of the invention are directed to compositions having antimicrobial activity comprising a metal halide, and a porous carrier particle in which the metal halide is infused, the carrier particle stabilizing the metal halide such that an antimicrobially effective amount of ions are released into the environment of the microbe. The terms "porous particle," "porous carrier particle" and "carrier particle" are used interchangeably herein. In one embodiment, one may form the antimicrobial compositions within the porosity of larger porous carrier particles. Metals and metal compounds or salts, particularly metal halides are preferred materials for this infusion. For example one may infuse silver bromide or particularly copper iodide into the pores. The porous particles should preferably have interconnected pores. A preferred upper range of the carrier particle is below 100 μm, and more preferably below 20 μm and most preferably below 5 μm. In other embodiments it is preferred that the surfaces of the porous particles (including pore surfaces) are hygroscopic (e.g., an abundance of silanol or other hydroxyl groups on the surface leads to hygroscopic materials). One preferred class of carrier particles that can be used are "wide pore" silicas. The carrier particles may be of any shape, e.g., spherical, irregular, angular, cylindrical, etc. For example, SILIAS-PHERE™ silicas from Silicycle (Quebec, Canada) may be used. The preferred silicas have a pore size (also referred to as average pore diameter) in the range of 2 to 100 nm, more preferably 4 to 20 nm). The porous carrier particles containing antimicrobial compositions in the pores can then be incorporated into bulk products, coatings, creams, gels and solutions to impart antimicrobial properties. These may be added as fillers to polymers which may then be shaped into bulk products via molding, extrusion, etc.

These porous materials are not zeolites, as the zeolites contain molecular channels formed as part of the crystal structures of aluminosilicates where the pore size (or average channel diameter) is generally less than 1 nm. The pore size in zeolites typically allows only single ions and very small molecules to pass through, and cannot accommodate the formation of discrete nanoparticles of antimicrobial materials. Larger molecules (including polymers) and solutions can be passed into and through the pores in the porous materials of this invention, and typically the pore geometry and/or sizes is irregular.

In a process embodiment of the invention, infusion of silver metal in a porous carrier particle is generally performed by starting with an aqueous solution of silver salt (e.g. silver nitrate with the surface modifiers (if used) dissolved therein) in water as described in the procedures below. The porous particles would be added to this solution so as to infuse the solution into the pores. The porous carrier particles would then be removed and optionally dried. These particles would then be added to an aqueous solution of reducing agent (e.g., 0.25% w/w $NaBH_4$) which causes silver metal to precipitate within the pores and also on the surfaces of the porous carrier particles. In another process embodiment metal halides may be formed in the pores where the porous carrier particles are treated with aqueous copper or silver salt solutions (or precursor solutions) followed by subjecting these to salt solutions of the required halide ions. If surface functionalization of the deposited materials is required, these salt solutions may have surface functionalization agents, or these may be sequentially treated with surface functionalization agent solutions, before being treated with catalysts or reactive solutions to convert them to the desired halides or metals. These may then be subjected to another series of similar treatment to precipitate more of the target metal or metal compound (as copper iodide) in the pores, or to precipitate a second compound or metal in the pores (e.g., depositing AgBr in pores which previously have been treated to deposit CuI). One may also mix different types of porous particles comprising different compositions of metals and metal compounds. Of particular utility are porous to particles containing CuI and porous particles where a significant fraction of the particles contain CuI and the remaining fraction contain other antimicrobial species, as Ag metal or AgBr.

Solvent selection plays a fundamental role in the use of porous carrier particles for delivery of inorganic metal compounds. Since an important part of the process is to ensure that solutions easily soak into the pores of the porous particles, it is required that the surfaces of the pores are compatible with the solvents used to form these solutions. In one embodiment, when the surfaces of the pores have hydrophilic properties solvents with high dielectric constant such as water, ethanol, methanol, acetonitrile, dimethylformamide, etc., are easily wicked into the pores by capillary forces. The rate of release of ions can be tailored by varying the size of the porous particles, particle shape, pore geometry (including pore size). In general, smaller particle sizes, elongated or irregular particle shapes vs spherical particle shapes given the same particle volume, and larger pore sizes will result in increased rates of ion release. One may mix different sized particles and also particles with different pore sizes to tailor release properties to suit both short term and long term release of ions in final products. Generally the particle size is varied between about 0.5 to 20 microns and pore size between 2 nm to 20 nm, with 4 to 15 nm being more preferred. These particles also have high surface areas and typically particles with surface areas greater than about 20 $m^2/g$ are desirable with more than 100 $m^2/g$ being preferred.

h. Particle Formation by Grinding

The particles of the compounds of this invention may be formed using other known methods. One such method of forming the desired microparticles and nanoparticles is by grinding of larger particles in a wet media mill. Such grinding is done in the presence of the functionalizing agents and an appropriate liquid medium, e.g. water. Wet media mills are available from several sources such as NETZSCH Fine Particle Technology, LLC., Exton Pa. (e.g., Nanomill Zeta®); Custom Milling and Consulting, Fleetwood, Pa. (e.g., Super Mill Plus); Glen Mills Inc, Clifton N.J. (e.g., Dyno® Mill). These mills typically comprise chambers in which hard ceramic or metal beads are vigorously stirred along with the slurries of the powders which result in grinding of the powders down to finer sizes. Typically, the size of the beads is about 1,000 times larger than the smallest average size to which the particles are ground to. Generally, the procedure starts using larger beads and as the particles are pulverized smaller beads are used in subsequent stages. As an example when one starts grinding particles which have a starting size in the range of about 1 to 10 microns, a bead size of 0.3 mm is used, which would result in particles of about 100-400 nm in size. In the next stage one may use beads of 0.1 mm in diameter which would result in particles ground to about 30-100 nm, and next one would use 0.05 mm diameter beads which would provide particles in the range of about 15-50 nm. Any particle size may be used that provides antimicrobial properties to the product which incorporates such particles, however, particle sizes below about 300 nm are preferred. The liquid media with ground particles may be directly incorporated in products (e.g., in coating formulations, creams, etc.), or these may be dried (in a rotoevap, or by spray drying, etc.) so that the particles along with the functionalizing agents are obtained as powders/flakes, etc, where these powder or flake particle sizes are preferably larger (several microns to several millimeters) to minimize possible health issues of workers, and then they are incorporated in formulations including melt blending with other polymers to form products by molding, extrusion, powder coating, etc.

i. Product-by-Process

Another embodiment of the invention described herein is a composition having antimicrobial activity made according to the process comprising the steps of obtaining CuI powder; dissolving the CuI powder in a polar nonaqueous solvent; adding an amount of hydrophilic polymer sufficient to stabilize the CuI in the polar, nonaqueous solvent; removing the solvent sufficient to dry the stabilized CuI particles whereby a polymer-complexed CO particle powder is formed; dispersing the polymer-complexed CuI particle powder in an aqueous solution having a pH of from about 1 to about 6 to form CuI particles stabilized in water whereby a polymer-complexed CuI particle; and optionally drying said stabilized CuI particles sufficient to remove the water.

The process is simple, efficient and highly quantitative.

Selection of the CuI powder source is the first step. CuI powder is typically purchased from any of numerous vendors including Wako Chemicals, Sigma Aldrich, VWR Scientific, etc. Any grade is acceptable, although a preferred brand and purity is at least 98% pure CuI available from Sigma Aldrich. Dissolution of the CuI is the next step. The CuI powder was dissolved in a polar nonaqueous solvent such as acetonitrile, although one of ordinary skill will realize that other nonaqueous solvents will function for this purpose, and come within the scope of the invention. CuI dissolves in polar nonaqueous liquids such as acetonitrile, dimethylformamide, etc. It is preferred not to use protic polar solvents. The next step is adding a polymer to the dissolved CuI solution. The function of the polymer is to complex with the CuI, so that when acetonitrile is removed the precipitating particles of CuI are prevented from coming together to form relatively large crystals. A preferred polymer is polyvinylpyrrolidone, which has dipole-bearing moieties. PVP effectively stabilizes emulsions, suspensions and dispersions. The polymer is adsorbed in a thin molecular layer on the surface of the individual colloidal particles to prevent contact between them and thereby overcome the tendency of these particles to form a continuous phase. Other polymers having dipole-bearing moieties are polyethylene glycol (PEG), surfactants, polymeric colloids, etc. The polymers may be hydrophilic such as PVP, polyacrylamide and PEG, copolymers of vinyl acetate and vinyl pyrrolidone or they may be hydrophobic such as several acrylic, methacrylic and polyesters and polyurethanes. Preferred hydrophobic polymers include acrylics, urethanes, polyesters and epoxies. The ratio of metal halide to polymer is preferably from about 1:0.5 to about 1:100, more preferably 1:1 to 1:80, and a most preferred ratio in the case of PVP is about 1:1 to 1:65.

The next step is to create nanoparticles of CO in the presence of the stabilizing agent. In one embodiment acetonitrile is removed using a rotoevap, which causes the CuI particles to precipitate out of solution complexed to the functionalizing agent as nanoparticles. This can be done at room temperature or the temperature can be elevated to hasten the drying process. The resulting powder can be stored indefinitely ("Step 1 Powder").

An optional step includes increasing the ratio of particle to functionalizing agent. The dry Step 1 Powder comprising CuI nanoparticles and the surface modifying polymer is dissolved in water to give a suspension of the nanoparticles. The concentration of CuI in the suspension is adjusted by varying the powder to water ratio. Adjusting the pH of the solution at this stage helps further improve the binding of the polymer to the nanoparticles and helps to break any agglomerates which may have formed. The preferred pH range is from about pH 0.5 to about pH 6. A specific pH value is dependent on the type of surface functionalizing agent, the size of the particles desired, the loading of the metal salt relative to the functionalization agent and the medium in which this would be dispersed in later. Useful acids to adjust pH include organic acids such as acetic acid, or mineral acids such as HCl, $H_2SO_4$ and $HNO_3$. The solution is stirred until optical clarity stabilized. The typical size of the resulting CuI particles ranges from about 4 nm to about 300 nm. Clear aqueous solutions typically have CuI particle sizes below about 10 nm, and with increasing particle size they become translucent to turbid. These solutions may also be dried and stored as powders ("Step 2 Powder"), which may be later dispersed into solutions. The average particle sizes of CuI in Step 2 Powders are typically smaller than the CuI particle sizes in Step 1 Powders.

The Powder (either from Step 1 or from Step 2) may be made from polymers other than PVP as discussed above. Such powders are mixed in a molten state with typical thermoplastic materials, such as nylons, polyesters, acetals, cellulose esters, polycarbonates, fluorinated polymers, acrylonitrile-butadiene-styrene (ABS) polymers, and polyolefins using a twin screw extruder. PEG is a preferred material for incorporating such nanoparticles into nylons, polycarbonates and polyester matrices, as transesterification will cause PEG to react with these materials and form covalent bonds to the polymer matrix. The high shear forces in a twin screw extruder will also help the agglomerated particles to disperse. This is preferably done in two steps. In the first step a concentrated antimicrobial polymer material is made with a relatively high concentration of antimicrobial metal halide particles of the invention, typically 1 to 10% by weight. This is usually blended in a twin screw type setup to provide a very intimate mixing. This is called a "master batch." This master batch can then be blended with resins so that the concentration of the antimicrobial material drops by a factor of about 5 to 25, and these blends are then used to make polymeric products by molding, extrusion, etc, where typically the concentration of the antimicrobial material in the final product is generally less than 2%, preferably less than 1%. The master batch can be blended with the neat resin on the processing equipment such as injection molding or the extrusion machine which makes the final product.

j. Theory

While not wanting to be bound by a particular theory regarding the origin of the surprising antimicrobial effectiveness of the novel compositions of the present invention, it is currently believed that the compositions of the invention (or ions released therefrom) are attracted to the surfaces of target pathogens. Once attached to the surfaces of the pathogens, the active oligodynamic species (generally ions such as metal cations but also included are the anions such as iodide) are transferred from the particles onto and/or into the pathogens. In some embodiments, the interaction between the functionalized particles and the pathogens may be sufficiently strong that the particles become embedded in the outer membrane of the pathogen, which can have a deleterious effect on membrane function as certain transport proteins may be inactivated by the cations. In other embodiments, particularly when the particles are very small (as less than 10 nm in size), the functionalized particles can be transported across the outer membrane of the pathogen and become internalized. Under these conditions, the oligodynamic species can directly transfer from the particles into the pathogen, bind to organelles, RNA, DNA etc. thereby hindering normal cellular processes. In the case of bacteria, this would correspond to the direct deposition of the active oligodynamic species in the periplasm or cytoplasm of the bacteria. This theory of the operative mechanism of the invention is just that, and is one of many that could explain the underlying efficacy.

4. Uses of the Compositions

The embodiments of the present invention have utility in a wide range of antimicrobial applications. Some of these applications are set forth in Table 1 below. Besides their direct use as antimicrobial compounds, other embodiments include several ways in which the functionalized particles can be incorporated into other materials to obtain novel and useful objects.

TABLE 1

Representative Applications of Functionalized Antimicrobial Nanoparticles

| No. | Application |
|---|---|
| 1. | Antimicrobial agents, administered either orally or via IV infusion |
| 2. | Coatings on implants |
| 3. | Constituents of implants |
| 4. | Sutures and medical devices |
| 5. | Pacemaker housings and leads |
| 6. | Filters for water supplies and air |
| 7. | Clothing for medical personnel, including nurses and surgeons |
| 8. | Coatings on or direct incorporation in components of ventilators, air ducts, cooling coils and radiators (for use in buildings and transportation) |
| 9. | Masks |
| 10. | Medical and surgical gloves |
| 11. | Textiles including bedding towels, undergarments and socks |
| 12. | Upholstery, carpets and other textiles, wherein the particles are incorporated into the fibers |
| 13. | Coatings on furniture for public use, as in hospitals, doctors' offices and restaurants |
| 14. | Wall coatings in buildings, including public buildings such as hospitals, doctors' offices, schools, restaurants and hotels |
| 15. | Coatings or compositions for use in transportation, such as ships, planes, buses, trains and taxis, where the antimicrobial compositions and coatings may be used for/applied to walls, floors, appliances, bathroom surfaces, handles, knobs, tables and seating |
| 16. | Coatings on and constituents of shopping bags |
| 17. | Coatings on school desks |
| 18. | Coatings on plastic containers and trays |
| 19. | Coatings on leather, purses, wallets and shoes |
| 20. | Coatings on shower heads |
| 21. | Self-disinfecting cloths |
| 22. | Coatings on bathroom door knobs, handles, sinks and toilet seats |
| 23. | Coatings on bottles containing medical or ophthalmic solutions |
| 24. | Coatings on or direct incorporation in keyboards, switches, knobs, handles, steering wheels, remote controls, of automobiles, cell phones and other portable electronics |
| 25. | Coatings on toys, books and other articles for children |
| 26. | Coatings on gambling chips, gaming machines, dice, etc. |
| 27. | Topical creams for medical use including use on wounds, cuts, burns, skin and nail infections |
| 28. | Shampoos for treating chronic scalp infections |
| 29. | Coatings on handles of shopping carts |
| 30. | Coatings on cribs and bassinettes |
| 31. | Bottle coatings for infant's bottles |
| 32. | Coatings or direct incorporation in personal items such as toothbrushes, combs and hair brushes |
| 33. | Coatings on currency, including paper, tissue paper, plastic and metal |
| 34. | Coatings or direct incorporation in sporting goods such as tennis rackets, gold clubs, gold balls and fishing rods |
| 35. | Adhesives used in bandages |
| 36. | Anti-odor formulations, including applications for personal hygiene such as deodorants |
| 37. | Objects and coatings to prevent formation of biofilms, particularly in marine applications |
| 38. | Dental coatings, sealants, fillings, crowns, bridges and implants |
| 39. | Molded and extruded products, including waste containers, devices, tubing, films, bags, liners and foam products. | a. Incorporation Methods

Embodiments of the invention are directed to compositions having antimicrobial activity made according to the following process comprising the steps of (a) forming stabilized copper iodide nanoparticles having an average size between 1000 nm and 4 nm; (b) dispersing the stabilized copper iodide nanoparticles in a suspending medium; (c) adding a quantity of the dispersed copper iodide nanoparticles to a manufacturing precursor; and (d) forming an article of manufacture at least partially from the manufacturing precursor whereby copper iodide nanoparticles are dispersed throughout the article. The manufacturing precursor may comprise a polymeric material. In further embodiments incorporation of the nanoparticles of the invention in molded and extruded thermoplastic products is typically achieved by first making master batches, wherein the antimicrobial compound (as particles or infused in porous matrices) are present in relatively high concentrations in polymeric matrices (preferably 1 to 10% of metal by weight). The master batches are then compounded with the polymer (resin) to make the molded or extruded product. This is typically done by first making the desired particles which are functionalized by polymers which are expected to have compatibility with the resins. These functionalized particles are formed in a dry state by removing water or any other solvents which are used and mixing them with the desired resins, usually on a mill or a twin screw extruder so that these mix intimately to have a high concentration of the antimicrobial compound. This is called a "master batch." This master batch is typically produced by companies which specialize in homogenously blending the two together and deliver their products as pulverized powders or pellets. These master batches are then used as additives to their resins by processors who use molding and/or extrusion operations to make these products. Such plastic processing operations include injection molding, injection blow molding, reaction injection molding, blown film processing, blow molding, rotational molding, calendaring, melt casting, thermoforming, rotational molding and multishot molding, etc. Starting with the antimicrobial concentration in a master batch as listed above, the processors use a typical ratio of resin to master batch material of 10:1 or so, which would then provide end products with antimicrobial concentrations of from about 0.1 to 1% (based on metallic concentration). Another important aspect should be considered when preparing the nanosized antimicrobial materials to be incorporated in downstream processing (e.g. at the facility of the masterbatch producer). To protect the health and safety of the workers employed at the antimicrobial material producing facility or other downstream processor, the possibility of getting the nanoparticles airborne should be minimized. One method that is commonly employed includes making the particle size of the dried powders (nanoparticles surface functionalized by polymers) relatively large (several microns to several millimeters) in comparison to the nanoparticles themselves. These dry powders are then easily handled and transported for downstream operators to use in paints, resins and other liquid carriers to create coatings of objects incorporating the functionalized nanoparticles.

Antimicrobial compositions of this invention may be added to extruded or molded polymer products homogeneously or to these objects as coatings or a layer using extrusion and molding operations. In the later case, operations such as co-extrusion, in-mold decoration, in-mold coating, multi-shot molding, etc are used where the antimicrobial additive is only present in that resin/material which forms the skin of the product as a result of these operations.

The functionalized microparticles and nanoparticles of the present invention may also be used by combining them with monomeric compositions or with solutions of pre-formed polymers, where the resulting materials containing the functionalized particles may be used to create two- and three-dimensional objects, adhesives and coatings, where the compositions are polymerized or crosslinked or densified after processing/setting the compositions into their final form. Coatings may also be deposited from solutions and aqueous polymeric emulsions containing the functionalized particles, where the formulations preferably comprise one or more film-forming polymers, or the particles may be employed in powder-coat formulations which are then processed into coatings.

When used in coatings and molded and other three dimensional products, these particles may scatter light, depending on their concentration, size and refractive index relative to the matrix. This can give rise to opacity or haze with increasing product thickness, particularly larger particles, higher particulate concentrations and larger differences in the refractive index (RI) of the particles and the matrix (e.g., see published US patent application 20100291374). In many applications this is not an issue, as the products have other opacifiers such as titanium dioxide. In other cases, e.g., for optical and ophthalmic use such as contact lenses, clarity is important, and one may optionally use these materials provided some of the parameters are controlled. Usually, the polymeric matrices of most common polymers have an RI in the range of 1.4 to 1.6. Silicones will be closer to 1.4, acrylics closer to 1.5 and polycarbonate closer to 1.6. The RI of copper iodide is 2.35, as an example if used as an antimicrobial additive. For high clarity (or low haze, typically less than 2% in the visible wavelengths as measured by ASTM test method D1003), it is preferred that the size of CuI particles is about less than 120 nm, volume loading less than 2% and product thickness less than 0.1 mm. CuBr and CuCl have lower refractive index as compared to CuI and will allow further relaxation of these numbers (meaning bigger particle sizes, higher volume loading and thicker products with high clarity).

Another embodiment of a product formed from such antimicrobial compositions are topical creams for both pharmaceutical and consumer product use. As an example, functionalized nanoparticles may be added to/formulated with Carbopol® polymers from Lubrizol to result in gels and creams which may be used as antimicrobial creams for treatment of infections, fungus, wounds, acne, burns, etc. Although any concentration of the functionalized nanoparticles may be used which provides effective treatment, a useful range of metal concentration (from the nanoparticles) in the finished product is 10 to 50,000 ppm. The precise concentration of any particular topical treatment can be assessed by testing the cream in any of the assays for antimicrobial effect presented herein, or known to one of ordinary skill.

The functionalized nanoparticles may also be formulated in petroleum jelly to provide superior water resistance. One may use additional surfactants and compatibilizers so that while the hydrophobic petroleum jelly protects the application area, it is also able to release the antimicrobial material to the underlying areas which may be hydrophilic. One of ordinary skill in the pharmaceutical art of compounding will know how to create antimicrobially active creams and ointments in combination with the functionalized metal halide powders of the present invention.

The antimicrobial materials of this invention may be used as an additive to other drug formulations including other antibiotic creams or formulations for infection control or related purposes. The antimicrobial materials of this invention may be added in a burn cream, which while assisting the repair of burned tissue will also keep any infection away, or it may be mixed with other antibiotics, infection reducing/prevention analgesic materials such as bacitracin, neomycin, polymyxin, silver sulfadiazine, selenium sulfide, zinc pyrithione and paramoxine, Many of these compositions listed above are available in commercial products, and the antimicrobial materials of this invention can be added to them to result in a concentration that is most effective. A preferred range of addition of the inventive antimicrobial materials herein is about 0.001 to 5% (based on the weight of the metal concentration of active ingredients) in the final product. For those formulations where solutions (or suspensions) are used as end products, a preferred range of the inventive antimicrobial material is below 1% by weight.

Imparting a thin coating to a surface allows one to obtain antimicrobial properties on a surface without infusing the potentially expensive materials into the bulk of the object. Powder coatings with the antimicrobial additives of this invention can be formed on metals, ceramics and other polymers (thermoplastics and thermosets). The technology for powder coating of materials is well established (e.g., see "A Guide to High Performance Powder Coating" by Bob Utec, Society of Manufacturing Engineers, Dearborn, Mich. (2002).) The matrices for powder coats are typically epoxies for indoor use where high chemical resistance is required and acrylics and polyesters including epoxy-polyester hybrids for outdoor use where superior UV resistance is needed. In typical powder coating operations, the object to be coated is suspended in a fluidized bed or subject to an electrostatic spray so that particles flowing past this object may stick on its surface (where the particles contact and melt due to higher surface temperature or the particles are attracted due to the static attraction and melted later). Typically, the powders melt and cure forming a coating. The coating processing temperatures are typically in the range of about 80 to 200° C. In the past, mainly metals were coated with polymeric powders. Recently, however, increasing use is being made of polyurethane powders for coating objects made of thermoset polymers and acrylic powders for coating thermoplastics objects (including acrylics which are cured using UV after the coating is deposited).

The antimicrobial additives of the current invention can be added to powder resins which are used for powder coatings. There are several ways to achieve this. In one method, the resin powders may be treated with solutions comprising the nanoparticles, and then the solvent is removed from the mixtures. These solvents may be solvents or non-solvents for the powders. In the former case, the powders may have to be pulverized again, and in the latter case the antimicrobial material forms a coat around the powders.

In another embodiment, the antimicrobial particles are formed as dry powders using surface modification polymers which are compatible with the resin powders. The two, i.e., powders with antimicrobial particles and resin powders are mixed (dry blending), and then subsequently the mixture is melt blended in an extruder and then the extrudate is pulverized into a resin powder with antimicrobial material for coating.

Another embodiment of the functionalized metal halide particles is directed to an antimicrobial composition comprising a povidone-iodine solution and at least one type of inorganic metal halide salt particle, the particle having an average size of from about 1000 nm to about 4 nm. A further embodiment of the povidone-iodine solution is wherein the at least one type of inorganic metal halide salt particle is selected from the group consisting of copper halide and silver halide, and a further embodiment comprises halides selected from the group consisting of iodide, chloride and bromide. The povidone-iodine compositions of the present invention may also be used to treat animals or humans to treat infected topical areas. As one example aqueous topical solutions of PVP and iodine (where iodine is about 8 to 12% by weight of PVP) are commonly used as disinfectants for wounds and for disinfecting skin prior to surgery. BETADINE® is a commercially available PVP-iodine solution. Povidone-iodine (PVP-I) is a stable chemical complex of polyvinylpyrrolidone (aka povidone, PVP) and elemental iodine. It contains from 9.0% to 12.0% available iodine, calculated on a dry basis. Some methods of making PVP-I are found in U.S. Pat. No. 2,706,701 (Beller et al.), U.S. Pat. No. 2,739,922 (Shelanski) U.S. Pat. No. 2,900,305 (Siggia) and U.S. Pat. No. 4,402,937 (Denzinger et al.) all incorporated herein by reference. 10% solutions in water are commonly used as a topical antiseptic. One may add the functionalized particles of metals and metal halides of the present invention to such PVP-iodine solutions to obtain new disinfectant solutions with notably enhanced disinfecting ability. Compositions of metal halide particles added to such PVP-I solutions also come within the scope of the current invention. Such a metal halide-enhanced PVP-I solution would be formulated having about 88-99% PVP, 2 to 10% Iodine, and 0.005-10% metal halide particles on a wt/wt basis. These weight proportions are relative to these three components excluding water and other solvents.

The compositions of the present invention can also contain any combination of additional medicinal compounds. Such medicinal compounds include, but are not limited to, antimicrobials, antibiotics, antifungal agents, antiviral agents, anti thrombogenic agents, anesthetics, anti-inflammatory agents, analgesics, anticancer agents, vasodilation substances, wound healing agents, angiogenic agents, angiostatic agents, immune boosting agents, growth factors, and other biological agents. Suitable antimicrobial agents include, but are not limited to, biguanide compounds, such as chlorhexidine and its salts; triclosan; penicillins; tetracyclines; aminoglycosides, such as gentamicin and Tobramycin™; polymyxins; rifampicins; bacitracins; erythromycins; vancomycins; neomycins; chloramphenicols; miconazole; quinolones, such as oxolinic acid, norfloxacin, nalidixic acid, pefloxacin, enoxacin, and ciprofloxacin; sulfonamides; nonoxynol 9; fusidic acid; cephalosporins; and combinations of such compounds and similar compounds. The additional antimicrobial compounds provide for enhanced antimicrobial activity. Some of these may be treat humans or animals as a whole (e.g., by oral administration, injection, etc).

Other embodiments of the present invention comprise medical devices that are rendered antimicrobial using methods comprising contacting the surfaces of the devices with the nanoparticle compositions of the invention. Medical devices, without limitation, include catheters (venous, urinary, Foley or pain management or variations thereof), stents, abdominal plugs, cotton gauzes, fibrous wound dressings (sheet and rope made of alginates, CMC or mixtures thereof, crosslinked or uncrosslinked cellulose), collagen or protein matrices, hemostatic materials, adhesive films, contact lenses, lens cases, bandages, sutures, hernia meshes, mesh based wound coverings, ostomy and other wound products, breast implants, hydrogels, creams, lotions, gels (water based or oil based), emulsions, liposomes, ointments, adhesives, porous inorganic supports such as silica or titania and those described in U.S. Pat. No. 4,906,466, the patent incorporated herein in its entirety by reference, chitosan or chitin powders, metal based orthopedic implants, metal screws and plates etc.

Also contemplated by the present invention are antimicrobial fabrics, such as those based on synthetic fibers, e.g., nylon, acrylics, urethane, polyesters, polyolefins, rayon, acetate; natural fiber materials (silk, rayon, wool, cotton, jute, hemp or bamboo) or blends of any of these fibers. The fibers or yarns may be impregnated with the functionalized metal salt nanoparticle formulations or for synthetic fibers the functionalized nanoparticles may be incorporated into resin melts/solutions that are used to form (extruded or spun) these fibers. In an alternative embodiment, the fabrics may be provided with coatings containing the antimicrobial compositions of the present invention. Devices, medical including dental and veterinary products and non-medical, made of silicone, polyurethanes, polyamides, acrylates, ceramics etc., and other thermoplastic materials used in the medical device industry and impregnated with functionalized nanoparticles using liquid compositions of the present invention are encompassed by the present invention. Various coating compositions for different polymeric, ceramic or metal surfaces that can be prepared from liquid compositions are also contemplated by the present invention, as are coating compositions which are impregnated with functionalized nanoparticles after their deposition. The coating compositions deposited from liquid solutions can be hardened by solvent loss or cured by thermal or radiation exposure or by incorporation of polymerization (e.g., cross-linking) agents in the coating formulations.

Antimicrobial medical and non-medical devices of the present invention can be made by treating the devices with antimicrobial functionalized metal salt compositions of the present invention by different methods. One disclosed method of the present invention comprises the steps of making the compositions in a dry particulate form that may be redispersed in an aqueous or nonaqueous carrier liquid, then contacting the compositions and the device surfaces for a sufficient period of time to allow accumulation of nanoparticles and then rinsing the excess of said composition away and drying the device. A modification of the disclosed method may involve drying or curing the surface of material first and then rinsing off the surface to remove excess. The method of contact may be dipping the device in the compositions or spraying the compositions on the device or coating blends of polymer solution and the compositions.

In other cases, the functionalized antimicrobial nanoparticles or porous particles containing antimicrobial compounds may be incorporated in polymer-based coating solutions from which antimicrobial coatings are deposited by end users. For example, the compositions of the invention may be applied to marine surfaces as a bactericidal agent. As another example, the compositions of the invention may be incorporated in polyurethane coating solutions and applied to furniture or flooring by the end users.

In another aspect, the present invention provides methods and compositions for applying antifouling coatings to an article such as a boat hull, aquaculture net, or other surface in constant contact with a marine environment. Materials that are immersed for long periods of time in fresh or marine water are commonly fouled by the growth of microscopic and macroscopic organisms. The accumulation of these organisms is unsightly and in many instances interferes with function. The natural process of accumulated growth is often referred to as fouling of the surface. There are a number of agents that may be applied to the surfaces to inhibit this growth, and may be combined with the materials of this invention. These agents are known in the art as anti-fouling agents. While many of these agents are highly effective, some of them may betoxic that often leech from the surface of the article and accumulate in the local environment. In one embodiment, the present invention provides a composition for treating a marine surface comprising a particle having at least one inorganic copper salt, and at least one functionalizing agent in contact with the particle, the functionalizing agent stabilizing the particle in suspension such that an amount of ions are released into the environment of a microbe sufficient to prevent its proliferation.

In many of these examples the materials of this invention may be combined with other known antimicrobial materials used for that particular application.

The following examples are illustrations of the embodiments of the inventions discussed herein, and should not be applied so as to limit the appended claims in any manner.

EXAMPLES

List of Chemicals Used
1. Silver nitrate>99%, Sigma-Aldrich (Milwaukee, Wis.) #S6506, 169.87 g/mol
2. Copper(I) Bromide>98% (Sigma Aldrich #61163)
3. Copper(II) acetate monohydrate≥98%, Sigma-Aldrich #217557, 199.65 g/mol
4. Sodium borohydride≥98.0%, Sigma-Aldrich #452882, 37.83 g/mol
5. Sodium hydroxide≥97.0%, Sigma-Aldrich #221465, 40 g/mol
6. Mereaptosuccinic acid (Thiomalic acid)≥99.0%, Sigma-Aldrich #88460, 150.15 g/mol, HOOCCH(SH)CH$_2$COOH
7. N-(2-Mercaptopropionyl)glycine (Thioglycine), Sigma-Aldrich #M6635, 163.19 g/mol, CH$_3$CH(SH)CONHCH$_2$COOH
8. Thioglycerol 95%, TCI America (Portland, Oreg.) #T0905, 108.16 g/mol, HSCH$_2$CH(OH)CH$_2$OH
9. Lipoic acid≥98.0% (Thioctic acid), Sigma-Aldrich #62320, 206.33 g/mol
10. Thiolactic acid 95%, Sigma-Aldrich T31003, 106.14 g/mol, CH$_3$CH(SH)COOH
11. (3-Mercaptopropyl)trimethoxysilane 95% (Thiosilane), Sigma-Aldrich #175617, 196.34 g/mol
12. 2-Aminoethanethiol>95% (Aminothiol), TCI America #77.15 g/mol
13. Aspartic acid≥99%, Sigma-Aldrich #A9006, 133.10 g/mol
14. Leucine≥99%, Sigma-Aldrich #L7875, 131.17 g/mol, $(CH_3)_2$cHCH$_2$CH(NH$_2$)CO$_2$H
15. Lysine>97%, TCI America #L0129, 146.19
16. Polyvinylpyrrolidone Mw=1,300,000 (PVP-1300K), Sigma-Aldrich #437190
17. Polyvinylpyrrolidone Mw=10,000 (PVP-10K), Sigma-Aldrich #PVP10
18. Polyvinylpyrrolidone, Luvitec K17 (BASF, Germany)
19. Copolymer Vinyl acetate-Vinyl pyrrolidone, Luvitec VA64 (BASF, Germany)
20. Polyethyelene glycol (PEG, MW 10,000) (Sigma-Aldrich 309028)
21. Hydrobromic acid 48%, Sigma-Aldrich #268003, 80.91 g/mol
22. Hydrochloric acid 36.5%, EMD Chemicals (Bridgetown, N.J.) #HX0603-75, 36.46 g/mol
23. Sodium iodide≥99.0%, Sigma-Aldrich #S8379, 149.89 g/mol
24. Potassium bromide≥99%, Sigma-Aldrich #22,186-4, 119 g/mol
25. Sodium chloride≥99.5%, Fluka (Milwaukee, Wis.) #71379, 58.44 g/mol
26. Acetonitrile anhydrous 99.8% (Sigma-Aldrich 271004)

27. Copper Iodide 98% (particle size 2 to 3 µm), 99.5% (particle size 1 to 2 µm) and 99.999% (particle size 1-2 µm) (Sigma Aldrich 205540; 3140 and 215554 respectively)
28. AgI nanoparticles, 25 nm (0.7% by weight) in PVP matrix (Chempilots a/s, Denmark
29. Copper metal, Sigma Aldrich Cat. #326453

5. Processes of Making the Functionalized Metal Salt Nanoparticles

The following methods were used in synthesizing the functionalized nanoparticles. The procedures below are divided into two sets, Procedure Set 1 and Procedure Set 2. The first set comprises procedures for making nanoparticles of various metal halides and silver metal; and the antimicrobial results from these are discussed in. Tables 2 through 9.

The following precursor solutions were made which were used for synthesizing particles for both sets:

Solution A: 4% $AgNO_3$ solution: 0.945 g Silver nitrate (Sigma-Aldrich #S6506) was dissolved in 14.055 g water (deionized). (This solution theoretically contains 4% by weight metallic silver.)

Solution B: 0.7% $NaBH_4$-solution: 0.07 g Sodium borohydride (Aldrich #452882) was dissolved in 9.93 g water. This solution was always prepared freshly just before its use.

Solution C: 10% Aspartic acid solution: 0.296 g NaOH pellets (7.4 mmol) was dissolved in 8.6 g water, 0.988 g Aspartic acid (7.4 mmol) (Sigma #A9006) added into it and then stirred until a clear solution was obtained.

Solution D: 10% Thioglycine-solution (TGN) 0.0245 g NaOH pellets (0.613 mmol) was dissolved in 0.875 g water, 0.1 g N-(2-Mercaptopropionyl)glycine (0.613 mmol) (Thioglycine Sigma #M6635) added into it and then stirred until a clear solution was obtained.

Solution E: 10% Thiomalic acid (TMAN) solution: 0.134 g NaOH pellets (3.35 mmol) was dissolved in 2.12 g water, 0.25 g Mercaptosuccinic acid (3.35 mmol) (Thiomalic acid, Aldrich #88460) added into it and then stirred until a clear solution was obtained.

Solution F: 10% Thioctic acid solution(TOA): 0.0193 g NaOH pellets (0.483 mmol) was dissolved in 0.88 g water, 0.1 g Lipoic acid (0.483 mmol) (Thioctic acid, Sigma #M6635) added into it and then stirred.

Solution G: Copper solution—Dissolve 0.0213 g CuBr in 0.048 g HBr 48%, diluting with 16 g water and, finally stirring until clear solution Solution H: 10% PVP-1300K or 10K-solution: 1 g Polyvinylpyrrolidone, mol. wt.=1,300,000 or 10,000 was dissolved in 9 g water.

Procedure Set 1

Examples 1-20

Synthesis of Functionalized Metallic Silver Nanoparticles

Example 1

Synthesis and Functionalization of Ag° Particles with Thiomalic Acid at Ag/SH=1/0.25 and Ag/Aspartic=1/5

1 g Solution A (0.371 mmol) was diluted with 2.39 g water. 2.47 g of Solution C (1.855 mmol) and 3-5 mins later 0.139 g Solution E (0.0926 mmol) were dropped under stirring into the diluted solution. After stirring further for 5 mins, 2 g Solution B (0.37 mmol) were dropped slowly into it under stirring. The final concentration of silver based on the calculation of metallic silver is 0.5% w/w.

Example 2a

Synthesis and Functionalization of Ag° Particles with Thioglycine at Ag/sH=1/0.25 and Ag/Aspartic=1/5

1 g Solution A (0.371 mmol) was diluted with 2.368 g water. 2.47 g Solution C (1.855 mmol) and 3-5 mins later 0.151 g Solution D (0.0925 mmol) were dropped under stirring into the diluted solution. After stirring further for 5 mins, 2 g Solution B (0.37 mmol) were dropped slowly into it under stirring. The final concentration of silver based on the calculation of metallic silver is 0.5% w/w.

Example 2b

Synthesis and Functionalization of Ag° Particles with Thioglycine at Ag/SH=1/0.25 and Ag/Aspartic=1/2

1 g Solution A (0.371 mmol) was diluted with 2.368 g water. 0.99 g Solution C and 3-5 mins later 0.151 g Solution D (0.0925 mmol) were dropped under stirring into the diluted solution. After stirring further for 5 mins, 2 g Solution B (0.37 mmol) were dropped slowly into it under stirring. The final concentration of silver based on the calculation of metallic silver is 0.5% w/w.

Example 3

Synthesis and Functionalization of Ag° Particles with PVP 0.1366 g silver nitrate was dissolved in 9.825 g water and then 2.168 g Solution H (PVP MW 10,000) in water added into it. Finally, 5.202 g of freshly prepared 0.25% w/w $NaBH_4$ in water was dropped slowly into the silver nitrate solution and kept stirring overnight to obtain silver particles. The final concentration of silver based on the calculation of metallic silver is 0.5% w/w.

Example 4

Synthesis and Functionalization of Ag° Particles with PVP and Thioglycine 0.1366 g silver nitrate was dissolved in 8.25 g water and then 2.168 g of Solution H (PVP MW 10,000) in water added into it. Finally, 5.202 g of freshly prepared 0.25% w/w $NaBH_4$ in water was dropped slowly into the silver nitrate solution and kept stirring overnight to obtain silver particles. The final concentration of silver based on the calculation of metallic silver is 0.55% w/w. 3.5 g of the silver sol produced in this way was diluted with 2.4 g of water and 0.146 g of Solution D, and the mixture was stirred for 2 hours to obtain silver particles modified both with PVP and thioglycine.

Example 5

Synthesis and Functionalization of AgBr Nanoparticles with PVP 0.2079 g silver nitrate was dissolved in 12.785 g water and then 3.30 g Solution H added into it. Finally a solution of 0.146 g potassium bromide in 5.20 g water was slowly dropped under stirring and kept stirring overnight to allow the formation of particles. The final concentration of silver based on the calculation of metallic silver is 0.61% w/w.

Example 6

Synthesis and Functionalization of AgBr Nanoparticles with Thiomalic Acid and Aspartic Acid at Ag/SH=1/0.25 and Ag/Aspartic=1/2

1 g Solution A (0.371 mmol) was diluted with 4.176 g water. 0.99 g Solution C (0.744 mmol) and 3-5 mins later 0.139 g Solution E (0.0925 mmol) were dropped under stirring into the diluted solution. After stirring further for 5 mins, the solution of 0.047 g HBr 48% (0.279 mmol) (Aldrich #268003) diluted in 2 g water was dropped slowly into it under stirring. The final concentration of silver based on the calculation of metallic silver is 0.5% w/w.

Example 7

Synthesis and Functionalization of AgCl Nanoparticles with Thiomalic and Aspartic Acid at Ag/SH=1/0.25 and Ag/Aspartic=1/2

1 g Solution A (0.371 mmol) was diluted with 3.843 g water. 0.99 g Solution C (0.744 mmol) and 3-5 mins later 0.139 g Solution E (0.0925 mmol) were dropped under stirring into the diluted solution. After stirring further for 5 mins, the solution of 0.028 g HCl 36.5% (0.280 mmol) (EMD Chem. #HX0603-75) diluted in 2 g water was dropped slowly into it under stirring. The final concentration of silver based on the calculation of metallic silver is 0.5% w/w.

Example 8

Synthesis and Functionalization of AgI Nanoparticles with Thioglycine at Ag/SH=1/0.25

1 g Solution A (0.371 mmol) was diluted with 4.804 g water. 0.151 g Solution D (0.0925 mmol) was dropped under stirring into the diluted solution. After stirring further for 5 mins, the solution of 0.042 g sodium iodide (Sigma-Aldrich #S8379) diluted in 2 g water was dropped slowly into it under stirring. The final concentration of silver based on the calculation of metallic silver is 0.5% w/w.

Example 9

Synthesis and Functionalization of AgBr Nanoparticles with Thioglycine and Aspartic Acid at Ag/SH=1/0.25 and Ag/Aspartic=1/2

1 g Solution A (0.371 mmol) was diluted with 3.826 g water. 0.99 g Solution C (0.744 mmol) and 3-5 mins later 0.151 g Solution D (0.0925 mmol) were dropped under stirring into the diluted solution. After stirring further for 5 mins, the solution of 0.033 g potassium bromide (0.277 mmol) (Aldrich #22, 186-4) dissolved in 2 g water was dropped slowly into it under stirring. The final concentration of silver based on the calculation of metallic silver is 0.5% w/w. The particle size was about 25 nm.

Example 10

Synthesis and Functionalization of AgBr Nanoparticles with Thioglycine and Aspartic Acid at Ag/SH=1/0.25 and Ag/Aspartic=1/5

Same procedure as Example 9, except that the amount of Solution C was 2.47 g (1.855 mol). In this case, the particle size was in the range of 10 to 15 nm.

Example 11

Synthesis and Functionalization of AgI Nanoparticles with 5 mol-% CuBr and Thioglycine at Ag/SH=1/0.5 and Ag/Aspartic=1/2

1 g Solution A (0.371 mmol) was diluted with 1.675 g water. 0.99 g Solution C (0.744 mmol) and 3-5 mins later 0.303 g Solution D (0.186 mmol) were dropped under stirring into the diluted solution. After stirring further for 5 mins, 2.010 g Solution G (0.0356 mmol bromide from HBr), was dropped slowly into the solution under stirring. At the final step, 0.0225 g sodium iodide (0.15 mmol) dissolved in 2 g water was added. The final concentration of silver based on the calculation of metallic silver is 0.5% w/w.

Example 12

Synthesis of AgBr or AgCl) Nanoparticles with Thioglycerol at Ag/SH=1/0.10 and Ag/PVP=1/2.5 w/w For preparation of AgBr nanoparticles, 1 g Solution A (0.371 mmol) was diluted with 3.88 g water. 1 g of Solution H (PVP-1300K) and 2-3 mins later 0.080 g 5% w/w aqueous solution of thioglycerol (0.037 mmol) (TCI America #T0905) were dropped under stirring into the diluted solution. In 2-3 mins, the solution of 0.0397 g potassium bromide (0.334 mmol) (Aldrich #22, 186-4) for AgCl) diluted in 2 g water was dropped slowly into it under stirring. The final concentration of silver based on the calculation of metallic silver is 0.5% w/w.

For preparation of AgCl nanoparticles the same procedure was used, but instead of 3.88 g of water 3.90 g of water was used and instead of 0.0397 g of potassium bromide, 0.0195 g of sodium chloride (Fluka #71379) was used.

Example 13

Synthesis of AgBr or AgCl Nanoparticles with Thioglycine at Ag/SH=1/0.5 and Ag/PVP=1/2.5 w/w a. production of silver bromide nanoparticles: 3.30 g Solution A were diluted with 12.056 g water. 3.30 g 10% PVP-10K-solution and the solution of 0.1426 g potassium bromide and 5.2 g water were respectively dropped slowly, and the nanoparticle suspension was stirred overnight.

b. surface modification: 0.204 g water and 0.146 g 10% Thioglycine-solution were dropped into 3.5 g portion of the synthesized silver halide nanoparticles above, and then stirred for, at least, six hours. The final concentration of silver based on the calculation of metallic silver is 0.5% w/w.

For preparation of AgCl nanoparticles the same procedure was used as above but instead of 12.056 g of water 12.128 g of water was used and instead of 0.1426 g of potassium bromide, 0.0715 g of sodium chloride was used.

Example 14

Synthesis of AgBr Nanoparticles with 5 mol-% CuBr and Thioglycine at Ag/SH=1/0.5 and Ag/PVP=1/2.5 w/w a. production of silver bromide nanoparticles: 3.30 g Solution A (1.224 mmol) were diluted with 10.585 g water. 3.30 g 10% PVP-10K-solution and 6.815 g copper solution (1.224 mmol bromide from HBr), which was made by dissolving 0.0213 g CuBr in 0.50 g HBr 48%, diluting with 16 g water and, finally stirring until a clear nanoparticle suspension was obtained, and the particle suspension was stirred overnight.

b. surface modification: 0.204 g water and 0.146 g Solution D were dropped into 3.5 g portion of the synthesized silver bromide nanoparticle suspension above, and then stirred for at least six hours. The final concentration of silver based on the calculation of metallic silver is 0.5% w/w.

Example 15

Synthesis of AgI Nanoparticles with 5 mol-% CuBr and Thioglycine at Ag/SH=1/0.5 and Ag/PVP=1/2.5 w/w a. production of silver iodide nanoparticles: 1.65 g Solution A (0.612 mmol) were diluted with 4.452 g water. 1.65 g Solution H. (PVP-10K) and 1.674 g copper solution (0.118 mmol bromide from HBr), which was made by dissolving 0.0213 g CuBr in 0.096 g HBr 48%, diluting with 8 g water and, finally stirring until a clear nanoparticle suspension. At the final step, 0.074 g sodium iodide (0.494 mmol) dissolved in 2 g water was added and stirred overnight.

b. surface modification: 0.204 g water and 0.146 g Solution D were dropped into 3.5 g portion of the synthesized silver iodide nanoparticle suspension above, and then stirred for, at least, six hours. The final concentration of silver based on the calculation of metallic silver is 0.5% w/w.

Example 16

Synthesis of AgI with 5 mol-% CuBr and Thioglycine at Ag/SH=1/0.5 and Ag/PVP=1/2.5 w/w; and Excess of Free Silver Ions a. production of silver iodide nanoparticles: 1.65 g Solution A (0.612 mmol) were diluted with 4.452 g water. 1.65 g Solution H (PVP-10K) and 1.674 g copper solution (0.118 mmol bromide from HBr), which was made by dissolving 0.0213 g CuBr in 0.096 g HBr 48%, diluting with 8 g water and, finally stirring until a clear sol were respectively dropped slowly. At the final step, 0.023 g sodium iodide (0.151 mmol) dissolved in 2.05 g water was added and stirred overnight. The molar ratio of silver nitrate to the sodium iodide ions was such that 56% of the silver was available as free ions.

b. surface modification: 0.204 g water and 0.146 g Solution D were dropped into 3.5 g portion of the synthesized silver iodide sol above, and then stirred for, at least, six hours. The final concentration of silver based on the calculation of metallic silver is 0.5% w/w.

Example 17

Synthesis of CuI nanoparticles with PVP at Cu/PVP=1/3.3 w/w 2.232 g Solution H (PVP-10K) solution was added into the solution of 0.211 g Copper(II) acetate monohydrate (1.057 mmol) dissolved in 6.227 g water under stirring. Afterwards, 0.3168 g sodium iodide (2.114 mmol) dissolved in 5 g water was dropped slowly into the copper solution and stirred overnight. Next day, the CuI suspension was washed to remove the formed iodine by extracting 7-10 times 2.5-3 ml with diethyl ether. The remaining ether was separated from the solution by evaporation under vacuum and then water was added to compensate for the loss of weight during processing. The final concentration of copper based on the calculation of metallic copper is 0.48% w/w. Reaction: $Cu^{2+}+2I^-\rightarrow CuI_2\rightarrow CuI_{(s)}+I_2$.

Example 18

CuI particles with Excess $Cu^{++}$ 1.86 g Solution H (PVP-10K) was added into the solution of 0.176 g Copper(II) acetate monohydrate dissolved in 6.448 g water under stirring. Afterwards, 0.132 g sodium iodide dissolved in 3 g water was dropped slowly into the copper solution and stirred overnight. The remainder of the process was the same as in Example 18, and the final concentration of copper in the suspension was 0.48% w/w.

Example 19

Synthesis of Silver Halide Nanoparticles with 5 mol-% CuI 0.236 g water and 0.114 g CuI as prepared in Method 17 were respectively dropped into 3.5 g solution of silver halide nanoparticles made by the procedure in Example 13 under stirring. The final concentration of silver based on the calculation of metallic silver is 0.5% w/w

Example 20

Synthesis of Silver Halide Nanoparticles with 5 mol-% CuI and Thioglycine at Ag/SH=1=0.5

0.09 g water, 0.114 g CuI in Method 17 and, 0.146 g Solution D were respectively dropped into 3.5 g solution of silver halide nanoparticles made by the procedure in Example 13 under stirring. The final concentration of silver based on the calculation of metallic silver is 0.5% w/w.

Procedure Set 2

Examples 21-42b

Example 21

Synthesis of Silver Nanoparticles Functionalized with Polyvinylpyrrolidone

To a reaction flask fitted with a stir bar and shielded from ambient light was added 0.1366 g of silver nitrate and 6.7 g of deionized water (DI water). This was stirred to give a clear solution. To this solution was added 2.168 g of a 40% w/w PVP, Aldrich, Mol wt 10 k). Under rapid stirring 5.202 g of a 0.25% w/w solution of sodium borohydride was added dropwise. This resulted in a very dark gray solution. The weight % silver in the final dispersion was 0.61% with a particle size of 10 to 40 nm as measured by dynamic light scattering after converting the data to volume fraction.

Example 22

Synthesis of Silver Bromide Nanoparticles Functionalized with Polyvinylpyrrolidone To a reaction flask covered to shield for ambient light, fitted with a stir bar and placed on an ice bath at 0° C. was added 0.2 g of silver nitrate and 51 g of DI-water. This was stirred for five minutes to form a complete solution. To this was added 3.34 ml of a 10 wt % solution in water of PVP (Aldrich, Mol. Wt. 10K) and stirred for ten minutes. To a second reaction vessel fitted with a stir bar and placed on an ice bath was added 0.157 g of potassium bromide and 21.4 g of DI-water. This was stirred for ten minutes to form a complete solution. This solution was transferred to a dropping funnel and added drop-wise (drop rate 0.436 ml/min) to the stirred silver nitrate/PVP solution at 0° C. During this process the silver nitrate solution was shielded from ambient light. The mixture was stirred overnight at 0° C. to give a light tan translucent mixture. Weight percent silver in the final mixture was 0.17%. The average particle size was 4 nm (based on volume fraction distribution by dynamic light scattering).

Example 23

Synthesis of Copper Iodide Nanoparticles Modified with PVP

To a 100 ml round bottom flask was added 0.380 g of copper iodide powder (Aldrich, 98%) and 60 mls of anhydrous acetonitrile. The flask was stoppered and placed under sonication for 10 minutes to form a clear yellow solution. To this solution was added 1.956 g of PVP (Aldrich, Mol, wt. 10K) and sonicated for 10 minutes to form a light green solution. The solution was placed on a rotovap and the acetonitrile removed under vacuum at 30° C. for approximately 30 minutes, then the temperature was increased to 60° C. for 15 minutes. This resulted in a bright green solid (a polymeric powder with coarse grain size that can be ground to any sized powder, preferably in a size much larger than nanosize). This solid was stable and could be redispersed in water to yield nanoparticles. To the flask containing the CuI/PVP solid was added a stir bar and 100 ml of DI-water to form a white milky opaque mixture. The mixture was shield form ambient light and stirred at 25° C. for three days this resulted in a translucent light pink stable dispersion. The weight % of Cu in the dispersion was 0.13%. The average particle size was 4 nm (based on volume fraction distribution by dynamic light scattering).

Example 24

Synthesis of CuI-PEG Dispersion w/ pH Modifier

A dispersion of CuI surface modified with polyethylene glycol (PEG), prepared in water using nitric acid as a pH modifier. To a reaction flask fitted with a stir bar was added 4.5 g of PEG (MW=10,000), and 0.0476 g CuI (99.999%) and 50 ml of acetonitrile. The mixture was stirred at room temperature for about 30 minutes to give a light green solution. The reaction flask was placed on a rotovap and the solvent removed at 25° C. to a paste-like consistency. The temperature was then increased to 45° C. to complete removal of acetonitrile. This resulted in a yellow powder. This powder was dispersed in 50 ml of DI water and 0.05 ml (0.07 g) of concentrated nitric acid was added to form an off-white mixture. Upon stirring in the dark over night the dispersion became clear to give a light yellow dispersion.

Example 25

Synthesis of AgBr:CuI/PVP Dispersion with a Molar Ratio $Ag^+$:$Cu^+$ 1:10 a. A copper iodide dispersion was prepared by direct reaction of the elements copper and iodine as follows: To a reaction flask was added 8.75 g of polyvinylpyrrolidone PVP (10,000 MW, Sigma Aldrich Cat. #PVP10), 50 ml DI water (18 Mohm-cm) and 0.125 g Cu metal (Sigma. Aldrich Cat. #326453). The mixture was stirred and cooled to 0° C. on an ice bath.

A second solution was prepared where 0.25 g of iodine (≥99.8% Sigma Aldrich Cat. #20, 777-2) and 8 ml of toluene (99.8% Sigma Aldrich Cat. #244511) were added to a reaction vessel. The mixture was stirred and cooled to 0° C. on an ice bath.

The iodine/toluene mixture was added slowly, 1 ml/minute, to the copper dispersion at 0° C. This was stirred for 30 minutes at 0° C. and then allowed to warm to room temperature under stirring. The solution was transferred to a separator funnel to give a clear toluene phase and dark orange aqueous phase of CuI dispersion. The aqueous phase (CuI) was separated from the toluene phase and stored shielded from light.

b. A 1:10 molar ratio of $Ag^+$:$Cu^+$ was prepared by mixing 1.5 g of AgBr dispersion prepared in Example #27 and 14.8905 g of CuI aqueous dispersion as described above. This resulted in a transparent dispersion yellow/brown dispersion.

Example 26

Preparation of Ag/PVP Dispersion

To a round bottom flask fitted with a condenser was added 50 ml of DI water (18 Mohm-cm) and 20 g of PVP (10,000 MW, Sigma Aldrich Cat.#PVP10). The mixture was stirred at room temperature to form a clear yellow solution. To this solution was added 0.04926 g of silver nitrate (≥99.0% ACS reagent Sigma Aldrich Cat. #209139) and the solution heated to 70° C. for 7 hours while stirring. During this time the reaction was followed by PVP absorption with the formation of the Plasmon peak at 425 nm due to the reduction of silver nitrate to silver metal by PVP. The final dispersion of Ag nano-particles was orange/brown in color and was transparent. Dynamic light scattering on a dilute sample of the dispersion gave a mean particle size of 7 nm.

Example 27

Synthesis of AgBr/PVP Dispersion

A silver bromide dispersion was prepared by dissolving 20 g of PVP (10,000 MW, Sigma Aldrich Cat.#PVP10) in 40 ml of DI water (18 Mohm-cm). To this solution while stirring was added 0.0492 g of silver nitrate, (≥99.0% ACS reagent Sigma Aldrich Cat. #209139), resulting in a clear yellow solution. In a separate reaction vessel a reducing solution was prepared by dissolving 0.0357 g of potassium bromide (anhydrous powder 99.95% Sigma Aldrich Cat. #451010), in 10 ml DI water (18 Mohm-cm). This KBr solution was added drop wise to the $AgNO_3$/PVP solution to form a yellow/orange transparent dispersion of AgBr. Dynamic light scattering on a dilute sample of the dispersion gave a mean particle size of 4 nm.

Example 28

Synthesis of CuI/PVP Dispersion

To a reaction flask containing 50 ml of anhydrous acetonitrile, (99.8% Sigma Aldrich Cat. #271004), was added 10 g of PVP (10,000 MW, Sigma Aldrich Cat.#PVP10) and stirred to form a light yellow solution. To this solution was added 0.0476 g of CuI (98.0% Sigma Aldrich Cat. #205540) and after stirring for 30 minutes this resulted in a clear pale green solution. Then the bulk of the acetonitrile was removed under reduced pressure at 30° C. to form a viscous paste. The temperature was then increased to 60° C. to completely remove the solvent to give a pale green solid. To this solid was added 50 ml of DI water (18 Mohm-cm) and stirred to give a transparent bright yellow dispersion. Dynamic light scattering on a dilute sample of the dispersion gave a mean particle size of 4 nm.

Example 29

Synthesis of Ag+AgBr Dispersion Molar Ratio $Ag^0$: $Ag+=1:5$

A 1:5 molar ratio of $Ag^0$:$Ag^+$ was prepared by mixing 2.0 g of Ag/PVP dispersion prepared in Example 26 and 10.022 g of AgBr/PVP dispersion as prepared in Example 27. This resulted in a transparent dispersion yellow/brown dispersion. Dynamic light scattering on dilute samples of the dispersions before mixing gave a mean particle size for Ag of 7 nm and AgBr of 4 nm.

Example 30

Synthesis of Ag:CuI Dispersion Molar Ratio $Ag^0$:$Cu^+$ 1:10

A 1:10 molar ratio of $Ag^0$: $Cu^+$ was prepared by mixing 1.5 g of Ag/PVP dispersion prepared in Example #26 and 14.8905 g of CuI/PVP dispersion as prepared in Example #28.

This resulted in a transparent yellow/brown dispersion. Dynamic light scattering on dilute samples of the dispersions before mixing gave a mean particle size for Ag of 7 nm and CuI of 4 nm.

Example 31

Synthesis of AgBr:CuI Dispersion Molar Ratio $Ag^+$:$Cu^+$ 1:10

A 1:10 molar ratio of $Ag^+$: Cu was prepared by mixing 1.5 g of AgBr/PVP dispersion prepared in Example #27 and 14.8905 g of CuI/PVP dispersion as prepared in Example #28. This resulted in a transparent yellow/brown dispersion.

Example 32

Synthesis of PVP-BASF-CuCl Dispersion

To a reaction flask containing 50 ml of anhydrous acetonitrile (99.8% Sigma Aldrich Cat. #271004) was added 14 g of PVP (BASF K17) and stirred to form a clear solution. To this solution was added 0.0239 g of CuCl (ACS reagent>99.0% Sigma Aldrich Cat. #307483) and after stirring for 30 minutes this resulted in a green/yellow solution. Then the bulk of the acetonitrile was removed under reduced pressure at 30° C. to form a viscous paste. The temperature was then increased to 60° C. to completely remove the solvent to give a pale green solid. To this solid was added 50 ml of DI water (18 Mohm-cm) and stirred to give a transparent bright yellow dispersion.

Example 33

Synthesis of CuI/PVP-BASF+Acetic Acid+$HNO_3$

To a reaction vessel were added 4.05 g of PVP (BASF K17) and 50 ml of anhydrous acetonitrile (99.8% Sigma Aldrich. Cat. #271004). This was capped and left to stir at room temperature to form a clear colorless solution. To this solution was added 0.0476 g of CuI (99.999% Sigma Aldrich Cat. #215554) and stirred at 25° C. for 30 minutes to form a transparent light yellow solution. The bulk of the acetonitrile was removed under reduced pressure at 30° C. to form a viscous paste. The temperature was then increased to 60° C. to completely remove the solvent to give a yellow uniform solid. To this solid was added 50 ml of DI water (18 Mohm-cm) and stirred to give a cloudy white dispersion. This was left to stir for 3 days in the dark the dispersion remained cloudy with a light white precipitate. While stirring 0.3 ml of glacial acetic acid (ACS reagent≥99.7% Sigma Aldrich Cat. #320099) was added immediately and the dispersion turned a orange/yellow color but was cloudy with a slight precipitate. To this mixture was added 0.05 ml of concentrated nitric acid (ACS reagent≥90% Sigma Aldrich Cat. #258121) and the solution cleared up to give a transparent light yellow solution.

Example 34

Synthesis of CuI/VP-VA Copolymer-BASF+$HNO_3$ Dispersion

To a reaction flask containing 50 ml of anhydrous acetonitrile (99.8% Sigma Aldrich Cat, #271004) was added 6.75 g of the copolymer PV-VA (BASF Luvitec VA 64) and stirred to form a clear solution. To this solution was added 0.0476 g of CuI (99.999% Sigma Aldrich Cat. #215554) and after stirring for 30 minutes this resulted in a green/yellow solution. The bulk of the acetonitrile was removed under reduced pressure at 30° C. to form a viscous paste. The temperature was then increased to 60° C. to completely remove the solvent to give a yellow uniform solid. To this solid was added 50 ml of DI water (18 Mohm-cm) and stirred to give a cloudy light yellow slurry. Under stirring 0.05 g of concentrated nitric acid (ACS reagent≥90% Sigma Aldrich Cat. #258121) was added to the mixture and it turned a light yellow color and was transparent.

Example 35

Synthesis of CuI/VP-VA Copolymer-BASF+$HNO_3$+Sodium Sulfite Dispersion

To a reaction flask containing 50 ml of anhydrous acetonitrile (99.8% Sigma Aldrich Cat. #271004) was added 13.5 g of the copolymer PV-VA (BASF Luvitec VA 64) and stirred to form a clear solution. To this solution was added 0.0952 g of CuI (99.999% Sigma Aldrich Cat. #215554) after stirring for 30 minutes this resulted in a green/yellow solution. Then the bulk of the acetonitrile was removed under reduced pressure at 30° C. to form a viscous paste. The temperature was then increased to 60° C. to completely remove the solvent to give a yellow uniform solid. To this solid was added 100 ml of DI water (18 Mohm-cm) and stirred to give a cloudy light yellow slurry. While stirring 0.05 g of concentrated nitric acid (ACS reagent≥90% Sigma Aldrich Cat. #258121) was added to the mixture and it turned a light yellow color and was transparent. To this CuI nano-dispersion was added 0.0135 g sodium sulfite (>98% Sigma Aldrich Cat. #S50505) which was equivalent to a concentration of 0.1 wt % based on total weight of copolymer. This addition had no effect on the appearance of the dispersion.

Example 36a

Synthesis of CuI/PVP-BASF+HNO$_3$

To a round bottom flask fitted with a stir bar were added 4.275 g of PVP (BASF K17) and 50 ml of anhydrous acetonitrile (99.8% Sigma Aldrich Cat. #271004). This was capped and left to stir at room temperature to form a clear colorless solution. To this solution was added 0.225 g of CuI (99.999% Sigma Aldrich Cat. #215554) and stirred at 25° C. for 30 minutes to form a transparent light yellow solution. The bulk of the acetonitrile was removed under reduced pressure at 30° C. to form a viscous paste. The temperature was then increased to 60° C. to completely remove the solvent to give a yellow uniform solid. To this solid was added 50 ml of Di water (18 Mohm-cm) and stirred to give a cloudy light yellow dispersion. While stirring 0.07 g of concentrated nitric acid (ACS reagent≥90% Sigma Aldrich Cat. #258121) was added to the mixture and it turned colorless and lightly cloudy with no precipitate. Dynamic light scattering on a diluted sample of the dispersion showed a bimodal distribution for volume fraction analysis with particles with peaks at diameter of 263 and 471 nm.

In another preparation following the above route, the proportion of components was changed. The amount of PVP (BASF K17) was 2.25 g in 50 ml acetonitrile, To this was added 0.0476 g of CuI (99.999%). This was processed as before and the dry powder was redispersed in 60 ml DI water. The solution was milky/pale yellow. After stirring 0.05 ml of nitric acid was added and stirred for two days. The solution became clear yellow with no precipitate. The solution remains stable after this process. The particle size was 4 mm.

Example 36b

Syntheses of CuI/PVP Particles—Control of Particle Size Using Acid

Copper iodide functionalized with PVP was prepared at different particle sizes by controlling the amount of nitric acid in the aqueous dispersion. The dispersions were prepared as described in Example 36a with the exception that the acid was added in the form of an aqueous solution in which the CuI/PVP powder was dispersed. The acid concentration was varied between 0 to 8.46 mM and gave a corresponding particle size variation of between 1070 to 5 nm as measured by dynamic light scattering. pH was read using a Fisher Scientific pH meter calibrated between 4 and 7 pH. The data is summarized in Table 1A which shows the effect of nitric acid in controlling the particle size. Samples were also made with acid but without copper iodide (samples S45, S47 and S49 with 0.846, 4.227 and 8.46 mM nitric acid respectively but without any copper iodide), these samples were tested to ensure that acidity of the sample was not responsible for the antimicrobial effect. Another aspect of note is that different sources of PVP may have different acidity depending on the method used to produce them, and may require a different extent of pH adjustment to control the particle size. As an example in this case when no nitric acid was used, the particle size was 1070 nm, whereas in Example 28 where a different PVP (PVP from Aldrich) was used (without added acid), the particle size was 4 to 6 nm.

TABLE 1A

| Sample # | % Cu | pH of dispersion | [HNO$_3$] | Particle Size (nm) |
|---|---|---|---|---|
| S44 | 0.0749 | 6.17 | 0.00 mM | 1070 |
| S46 | 0.0749 | 2.59 | 0.846 mM | 323 |
| S48 | 0.0749 | 2.36 | 4.227 mM | 315 |
| S50 | 0.0749 | 1.37 | 8.460 mM | 5 |

To a 50 ml round bottom flask was added 0.81 g of PVP (Luvitec K17 from BASF) and 15 ml acetonitrile. This was stirred to form a solution free of color. To the PVP solution was added 0.0095 g CuI (Aldrich, 99.5% purity). This was stirred to form a transparent yellow solution. The PVP/CuI solution was dried on a rotary evaporator at 45° C. This formed a yellow solid. This solid was redispersed in 7.5 ml of deionized water. This was stirred to form a cloudy white solution. To the redispersed PVP/CuI solution was added different acids in a volume of 7.5 ml in different concentrations (strengths) as shown in the table below. This solution was stirred while keeping it away from light. After 1 day of stirring the solution in most cases it became transparent as shown in Table 1B ("Solution Clarity" column). The pH of these solutions was also measured. The pH is dependent on several factors, type and amount of PVP, amount of CuI, type and concentration of acid in the solution. The average particle size in clear solutions is expected to be below 10 nm, and significantly higher for others. The solution was diluted to 59.07 ppm of total copper content in phosphate buffered saline (PBS; pH 7.4; Sigma-Aldrich, St. Louis, Mo.) and pH measurements were again taken. This was the typical concentration of copper that was used in generating several of the antimicrobial testing results in liquid suspensions. This test was done to assure that antimicrobial properties of these nanoparticles are measured in suspensions which are in a consistent pH range of about 6 and 7.4 (or up to the pH of the buffer). As a reference, the pH of human skin is about 5.5, urine is about 6.0 and of blood 7.34 to 7.45. The results after adding different strengths of hydrochloric acid, nitric acid, and sulfuric acid are summarized in Table 1B. This table shows that different acids can be used in different concentrations to control both the pH and the particle size, but all of these in the buffer solution can result in pH greater than 6.

TABLE 1B

| Experiment | wt % Cu+ | Wt % PVP | [Acid] | Neat pH of aqueous dispersion | Solution clarity | pH in buffer, 59.07 ppm Cu$^+$ |
|---|---|---|---|---|---|---|
| 1 | 0.00317 | 8.1 | 0 | 6.110 | Cloudy | 7.303 |
| 2 | 0.00317 | 8.1 | HCl 2 mM | 3.153 | Cloudy | 7.020 |
| 3 | 0.00317 | 8.1 | HCl 4 mM | 2.636 | Clear | 7.020 |
| 4 | 0.00317 | 8.1 | HCl 6 mM | 2.285 | Clear | 6.810 |
| 5 | 0.00317 | 8.1 | HNO$_3$ 2 mM | 2.621 | Clear | 7.019 |

TABLE 1B-continued

| Experiment | wt % Cu+ | Wt % PVP | [Acid] | Neat pH of aqueous dispersion | Solution clarity | pH in buffer, 59.07 ppm Cu$^+$ |
|---|---|---|---|---|---|---|
| 6 | 0.00317 | 8.1 | HNO$_3$ 4 mM | 2.130 | Clear | 6.690 |
| 7 | 0.00317 | 8.1 | HNO$_3$ 6 mM | 1.885 | Clear | 6.297 |
| 8 | 0.00317 | 8.1 | H$_2$SO$_4$ 2 mM | 2.458 | Clear | 6.877 |
| 9 | 0.00317 | 8.1 | H$_2$SO$_4$ 4 mM | 2.074 | Clear | 6.448 |

Example 37

Synthesis of Ag$_{0.5}$Cu$_{0.5}$I Nanoparticles

This method results in "solid solutions," meaning not separate distinct liquid phases of CuI and AgI but where one metal is substituted for the other randomly throughout the crystal or a non-crystalline lattice structure of the solid. 10 g of PVP (10,000 MW, Sigma Aldrich Cat.#PVP10) was dissolved in 40 ml of DI water (18 Mohm-cm) and to this was added 0.0246 g (0.145 mmol) of silver nitrate (≥99.0% ACS reagent Sigma Aldrich Cat. #209139). To this pale yellow solution was added 0.0350 g (0.145 mmol) of copper nitrate trihydrate, (≥98% Sigma Aldrich Cat. #61197), to give a dark yellow solution. In a separate vessel 0.0481 g (0.29 mmol) of potassium iodide, (≥99.0% ACS reagent Sigma Aldrich Cat. #60400), was dissolved in 10 ml DI water (18 Mohm-cm) and added drop wise (0.34 ml/minute) to the silver, copper nitrate PVP solution. This resulted in a pale yellow dispersion of a solid solution of silver-copper iodide (Ag$_{0.5}$Cu$_{0.5}$I). Dynamic light scattering on a dilute sample of the dispersion gave a mean particle size of 29 nm.

Example 38

Synthesis of Ag$_{0.25}$Cu$_{0.75}$I Nanoparticles

Nano-particle dispersion of silver copper iodide solid was prepared according to example #37 except that the molar concentrations of the metal ions were adjusted according to the formula Ag$_{0.25}$Cu$_{0.75}$I. Dynamic light scattering of a dilute sample of the dispersion gave a mean particle size of 10 nm.

Example 39

Synthesis of Ag$_{0.75}$Cu$_{0.25}$I Nanoparticles

Nano-particle dispersion of silver copper iodide solid was prepared according to example #37 except that the molar concentrations of the metal ions were adjusted according to the formula Ag$_{0.75}$Cu$_{0.25}$I. Dynamic light scattering of a dilute sample of the dispersion gave a mean particle size of 8 nm.

Example 40

Infusion of Metal and Inorganic Metal Compounds into Porous Particles

This example teaches the synthesis and antimicrobial testing of a composition having antimicrobial activity comprising a copper halide particle selected from the group consisting of copper iodide, copper bromide and copper chloride, and a porous carrier particle in which the copper halide particle is infused, the carrier particle stabilizing the copper halide particle such that an antimicrobially effective amount of ions are released into the environment of the microbe.

The copper halide-porous particle composition is demonstrated by two process embodiments which were used to infuse copper halide into porous silica carrier particles. These methods may also be used to incorporate other metal compounds (including other metal halides) and metals by reactive precipitation and/or by the evaporation of the solvent. To increase the amount of the infused material in the carrier particle, concentrated solutions (including saturated or close to saturated solutions) of metal halides can be used. Once the solutions are infused in the pores, the porous particles are removed and dried so that the metal compound deposits on the surface of the particles (including surfaces of the pores). To increase the concentration of the metal halides further, one can repeat the process several times using saturated or close to saturated solutions so that the already deposited material is not solubilized. Various types of porous silica particles were used from Silicycle Inc. (Quebec City, Canada). These were IMPAQ® angular silica gel B10007B hydrophilic silica. They had average particle size of 10 μm and a pore size of 6 nm, with pore volume of about 0.8 ml/g and a surface area of >450 m$^2$/g); or silica with particle size of 0 to 20 μm range (pore size 6 nm, surface area 500 m$^2$/g); or silica 0.5 to 3 μm in range (product number R10003B, pore size 6 nm).

Method 1

0.6 g of CuI (from Sigma Aldrich, 98.5% purity) was dissolved in 20 ml acetonitrile at room temperature (use of about 0.68 g of CuI would have saturated the solution). 1 g of silica powder (0-20 μm) was added to this solution. The solution was stirred for three hours at room temperature (this time period could have varied from a few seconds to more than three hours), then filtered through 0.45 μm nylon filter (from Micron Separations Inc., Westboro, Mass.) and finally dried at 70° C. Using a spatula, the material is easily broken down into a fine powder. The analysis of this silica using inductively coupled plasma (ICP) atomic absorption spectroscopy at a commercial laboratory showed that the copper by weight was 1.88% of silica.

Example 41

Infusion of Metal and Inorganic Metal Compounds into Porous Particles

Method 2

In this method the solvent for CuI was 3.5 M KI solution in water. KI solution was prepared by dissolving 29 g of KI in 40 ml of deionized water, stirring and adding water to complete a final volume of 50 ml. The volume of the KI solution after mixing was measured to be 50 ml. 1.52 g of CuI was added and stirred at room temperature. The solution turned yellow immediately and by the next day it darkened somewhat. To 6 ml of this solution, 0.5 g of porous silica carrier particles (0.5 to 3 μm) were added and stirred for six hours. The silica particles were filtered and were then added to water so as to precipitate CuI trapped on the surface of the silica. The analysis of this silica using ICP AA instrument showed that the copper by weight was 1.46% of silica.

Example 42a

Preparation of Polyurethane/CuI Dispersions by Wet Grinding

The samples were ground in a wet grinding mill produced by Netzsch Premier Technologies LLC (Exton Pa.), equipment model was Minicer®. The grinding beads were made of YTZ ceramic (300 μm in diameter). The interior of the mill was also ceramic lined. 99.9% purity CuI was used to be ground to finer particle size using aqueous media. Two different types of aqueous media were used. In the first case the material was an aliphatic urethane 71/N aqueous dispersions (35% solids) sold under the Tradename of ESACOTE® obtained from Lamberti SpA, (Gallarate, Italy). This material is used for aqueous furniture varnishes and also for metal coatings. The second material was a PVP (Aldrich molecular weight 10,000) solution in water.

For the polyurethane dispersion, 10 g of copper iodide was added for every 100 ml of dispersion. As the grinding proceeded, the viscosity increased and the dispersion was diluted with a mixture of 7% n-ethyl pyrrolidone and 93% water by weight. 60 ml of diluents was added throughout the process. The samples started out with 50 grams CuI and 500 grams of the PU dispersion. It should be noted that the surface of the ground particles was being functionalized by the PU dispersion (which comprised of hydrophobic polyurethane and a surfactant amongst other additives). A total of 60 grams of 7% 1-ethyl-2-pyrrolidone was added periodically throughout the milling process as follows: 25 grams at 75 minutes, 10 grams at 105 minutes, 15 grams at 120 minutes, and 10 grams at 150 minutes. Approximately 100 mL of product was taken out of the mill at 75 and 105 minutes (before the addition of the solvent), and the remainder was pumped out at the 210 minute mark. At the end the process, the total solids content including CuI was 35%, the polymeric content was 27.2% and the % of CuI to that of the polymer was 28.6%. During grinding the maximum temperature was 38° C. After 210 minutes of grinding, the particle size was measured. The circulation speed and agitation speed settings on the equipment were both at six. Particle size measurement was conducted by HORIBA Laser Scattering Particle Size Distribution Analyzer (model LA-950A). The average particle size was 68 nm with a standard deviation of 7.4 nm. To test the stability of the suspension with ground particles, the particle size was measured again the next day which gave the mean size as 70 nm with a standard deviation of 8.2 nm.

Example 42b

Preparation of PVP/CuI Dispersions by Wet Grinding

For the PVP dispersion, the formulation was 480 grams: 20 grams CuI, 60 grams PVP (Aldrich 10,000MW), 400 grams de-ionized water. Grinding parameters were the same as in 42a. Samples were pulled out after 45, 120 and 210 minutes of grinding under the same conditions as above (Example 42a), the particle size (mean size) was respectively 920 nm (bimodal distribution with peaks at 170 and 1,500 nm), 220 nm and 120 nm respectively, when measured using the HORIBA apparatus as described above.

6. Testing of Particle Suspensions for Efficacy Against Bacteria, Viruses and Fungi a. Microbial Assays The antimicrobial effectiveness of the functionalized particles was evaluated using the following standard methods.

Maintenance and Preparation of Microbial Isolates:

Test bacteria were obtained from the American Type Culture Collection (ATCC, Manassas, Va.) or The University of Arizona, Tucson, Ariz.: *Escherichia coli* (ATCC #15597), *Enterococcus faecalis* (ATCC #19433), *Pseudomonas aeruginosa* (ATCC #27313), *Staphylococcus aureus* (ATCC #25923), *Mycobacterium fortuitum* (ATCC #6841), *Salmonella enterica* serovar *Typhimurium* (ATCC 23564), and *Streptococcus mutans* (ATCC #25175). *Escherichia coli* 77-30013-2 a copper resistant strain was obtained from Dr. Chris Reusing and *Bacillus Cereus* was obtained from Dr. Helen Jost at the University of Arizona, Tucson, Ariz.

Bacterial isolates used in these studies were routinely cultured on Tryptic Soy Agar (TSA; Difco, Sparks, Md.) at 37° C. or in Tryptic Soy Broth (TSB) medium at 37° C. on an orbital shaker at 200 r.p.m. in the case of *M. fortuitum*, Tween 80 (polyethylene glycol to sorbitan monooleate; Sigma Aldrich, St. Louis, Mo.) was added to the broth to a final concentration of 0.1% (v/v) to inhibit the formation of bacterial aggregates.

Maintenance and Preparation of Viruses:

Test viruses were obtained from the ATCC or Baylor College of Medicine Houston, Tex.: MS2 coliphage (ATCC#15597-B1) and Poliovirus 1 (strain LSc-2ab) Baylor College of Medicine Houston, Tex.

MS2 was maintained as described: Test tubes containing approximately 5 mss of soft TSA containing 0.8% Bacto agar (Difco, Sparks, Md.) at 45° C. were inoculated with overnight cultures of *E. coli* and approximately $1 \times 10^5$ plaque forming units (PFU) of MS2. The soft agar overlay suspensions were gently vortexed and poured evenly across the top of TSA plates and allowed to solidify. Following incubation of 24 hours at 37° C., 6 ml of sterile phosphate buffered saline (PBS; pH 7.4; Sigma-Aldrich, St. Louis, Mo.) was added to the agar overlays and allowed to sit undisturbed for 2 hours at 25° C. Following the incubation the PBS suspension was collected and centrifuged (9,820×g for 10 min) to pellet the bacterial debris. The remaining supernatant containing MS2 was filtered through a 0.22 μm (Millex; Millipore, Bedford, Mass.) membrane pre-wetted with 1.5% beef extract and stored in sterile tubes at 4° C. until use. To determine the MS2 titer, the double-agar overlay method as described above was used, however after the 24 hour incubation at 37° C., MS2 was enumerated by plaque formation to determine the number of PFU/ml.

Poliovirus 1 (strain LSc-2ab) was maintained as described: Poliovirus 1 were maintained in cell culture flasks containing BGM (Buffalo green monkey kidney; obtained from Dan Dahling at the United States Environmental Protection Agency, Cincinnati, Ohio) cell monolayers with minimal essential medium (MEM, modified with Earle's salts; Irvine Scientific, Santa Ana, Calif.) containing (per 100 ml total volume) 5 ml of calf serum (CS; HyClone Laboratories, Logan, Utah), 3 ml of 1 M HEPES buffer (Mediatech Inc., Manassas, Va.), 1.375 ml of 7.5% sodium bicarbonate (Fisher Scientific, Fair Lawn, N.J.), 1 ml of 10 mg/ml kanamycin (HyClone Laboratories, Logan, Utah), 1 ml of 100× antibiotic-antimycotic (HyClone Laboratories, Logan, Utah), and 1 ml of 200 mM glutamine (Glutamax; HyClone Laboratories, Logan, Utah) at 37° C. with 5% $CO_2$.

Viruses were propagated by inoculating BGM cell monolayers. Following the observation of ≥90% destruction of the cell monolayer, the cell culture flasks were frozen at −20° C. and thawed three successive times to release the viruses from the host cells. The culture suspension was then centrifuged (1000×g for 10 min) to remove cell debris, and then precipitated with polyethylene glycol (PEG; 9% w/v) and sodium chloride (5.8% w/v) overnight at 4° C. (Black et al. "Determination of Ct values for chlorine resistant enteroviruses," J. Environ. Sci. Health A Tox. Hazard Subst. Environ. Eng. 44: 336-339, 2009). Following the overnight incubation the viral suspension was centrifuged (9,820×g for 30 min at 4° C.) and the viral pellet re-suspended in 10 ml PBS. A Vertrel XF extraction was performed at a 1:1 ratio to promote monodispersion of the virus and, the removal of lipids (centrifugation at 7,500×g for 15 mM at 4° C.) (Black et al., 2009). The top aqueous layer containing the virus was carefully removed using a pipette and aliquoted in 1 ml volumes in sterile cryogenic vials (VWR, Radnor, Pa.). A viral titration for poliovirus 1 was performed using a 10-fold serial dilution plaque-forming assay described by Bidawid et al., "A feline kidney cell line-based plaque assay for feline calicivirus, a surrogate for Norwalk virus." J. Virol. Methods 107: 163-167. (2003). BGM cell monolayers in 6-well tissue culture plates (Corning Inc., Corning, N.Y.) were rinsed twice with 0.025 M TRIS buffered saline [0.32 L TBS-1 (31.6 g/L Trizma base, 81.8 g/L NaCl, 3.73 g/L KCl, 0.57 g/L $Na_2HPO_4$—anhydrous) in 3.68 L ultrapure $H_2O$] and then inoculated with 0.1 ml volumes of 10-fold serial dilutions of the virus stock and incubated at 37° C. for 30 minutes. Following this incubation period, 3 ml of a soft solution of MEM containing (per 100 ml) 0.75% Bacto-agar (Becton, Dickenson and Co., Sparks, Md.), 2% FBS (HyClone Laboratories, Logan, Utah), 3 ml of 1M HEPES buffer (Mediatech Inc., Manassas, Va.), 1 ml of 7.5% sodium bicarbonate (Fisher Scientific, Fair Lawn, N.J.), 1 ml of 10 mg/ml kanamycin (HyClone Laboratories, Logan, Utah), 1 ml of 100× antibiotic-antimycotic (HyClone Laboratories, Logan, Utah), and 1 ml of 200 mM glutamine (Glutamax; HyClone Laboratories, Logan, Utah) was added as an overlay to each well and allowed to solidify. The plates were then incubated at 37° C. with 5% $CO_2$ for two days. Following incubation, the agar overlays were removed and the cell monolayers were stained with 0.5% (w/v) crystal violet (Sigma-Aldrich, St. Louis, Mo.) dissolved in ultrapure water and mixed 1:1 with 95% ethanol. Plaques were counted to enumerate infectious viruses.

Maintenance and Preparation of Molds:

Test molds were obtained from The University of Arizona, Tucson, Ariz.: *Penicillium* and *Aspergillus niger* isolates were obtained from Dr. Charles Gerba.

*Penicillium* and *Aspergillus niger* isolates were maintained on Sabouraud's agar (Neogen Corporation, Lansing, Mich.) slants at 25° C. Mature slant cultures containing fruiting bodies were washed repeatedly with 10 mL of sterile PBS to release spores. The spore suspension was then transferred to a 15 mL conical tube and vortexed to disperse the spores.

1) Bacterial Kill Assay.

Overnight suspensions were harvested by centrifugation (9,820×g, 15 min, 20° C., JA-14 rotor, Beckman J2-21 centrifuge; Beckman Coulter, Inc., Fullerton, Calif.) and resuspended in 100 mls of sterile PBS. The above centrifugation process was carried out two additional times and the final harvest was resuspended in 10 mls of PBS. Bacterial suspensions were then adjusted in PBS to an optical turbidity (measured using a BIOLOG turbidimeter, Hayward, Calif.) equivalent to a McFarland number 0.5 standard. Sterile 50 ml polypropylene conical tubes (Becton Dickinson and Company, Franklin Lakes, N.J.) containing PBS were inoculated with test suspensions to a final concentration of approximately $1.0\times10^6$ CFU/ml. Functionalized particles of the present invention were evaluated at either 10 ppm silver or 59 ppm copper. Test samples were then placed on an orbital shaker (300 rpm) at 25° C. for the duration of the experiment. At predetermined time intervals (e.g., 1, 3, 5, 24 hours), 100 μl samples were collected and neutralized with Dey Engley neutralizing broth (D/E; Difco, Sparks, Md.) at a ratio of 1:10. Bacterial samples were serially diluted in sterile PBS and enumerated using the spread plate method (Eaton et al., "Spread. Plate Method," in Standard Methods for the Examination of Water & Wastewater, $21^{st}$ ed., American Public Health Association, Washington, D.C., pp. 9-38-9-40.9215C. 2005) at 37° C. for either 24 hours (*E. coli, P. aeruginosa, S. aureus*, and *E. faecalis*) or 48 and 72 hours (*M. fortuitum* and *S. mutans*).

Evaluation of Antimicrobial Properties of Porous Silica Particles:

Experiments for porous silica particles without CuI and those comprising CuI were conducted in 100 ml of sterile PBS in 250 ml Erlenmeyer flasks. Bacterial suspensions were added to a final concentration of $1.0\times10^6$ CFU/ml. Powdered silica samples were tested at 0.1 g dry weight per 100 ml of PBS. A control with bacteria but no added particles was also included. Powdered silica samples were added to each flask and kept in suspension by agitation using stir plates (VWR VMS-C7, VWR, Radnor, Pa.) for the duration of the experiment at 25° C. At predetermined time intervals (e.g. 15 minutes, 1, 6, 24 hours), 1 ml samples were collected and neutralized with Dey Engley neutralizing broth (D/E; Difco, Sparks, Md.) at a ratio of 1:2.

2) Viral Kill Assay.

Poliovirus 1 experiments were conducted in 10 ml of sterile PBS in 50 ml sterile polypropylene conical tubes (Becton Dickinson and Company, Franklin Lakes, N.J.). MS2 experiments were conducted in 50 ml of sterile PBS in 250 ml sterile covered Pyrex beakers. The purified stocks of the viruses were added separately to the tubes/beakers to achieve the desired final test concentration of approximately $1.0\times10^6$ PFU/ml. Functionalized particles of the present invention were evaluated at either 10 ppm silver or 59 ppm copper. The tubes/beakers were then placed on an orbital shaker (300 rpm) for the duration of the experiment. Experiments were performed at 25° C. At predetermined time intervals (e.g., 3, 5, 7, 24 hours), 100 μl samples were collected and neutralized with Dey Engley neutralizing broth (D/E; Difco, Sparks, Md.) at a ratio of 1:10. Functionalized particle efficacy was determined by the agar overlay method as described above in maintenance and preparation of viruses section.

3) Mold Kill Assay.

Sterile 50 ml polypropylene conical tubes (Becton Dickinson and Company, Franklin Lakes, N.J.) containing PBS were inoculated with mold spore suspensions of approximately $1.0\times10^6$ CFU/ml. Functionalized particles of the present invention were evaluated at either 10 ppm silver or 59 ppm copper. Test samples were then placed on an orbital shaker (300 rpm) at 25° C. for the duration of the experiment. At predetermined time intervals (e.g., 1, 3, 5, 24 hours), 100 μl samples were collected and neutralized with Dey Engley neutralizing broth (DIE; Difco, Sparks, Md.) at a ratio of 1:10. Mold samples were serially diluted in sterile PBS and enumerated with the spread plate method (Eaton et al., "Spread Plate Method," in Standard Methods for the Examination of Water & Wastewater, $21^{st}$ ed., American Public Health Association, Washington, D.C., pp. 9-38-9-40. 9215C, 2005) at 25° C. for 48 and 72 hours.

4) Determination of Antimicrobial Activity by Optical Density Measurements.

Bacterial suspensions with or without antimicrobial particles where monitored for growth using a turbidimetric measurement. Turbid or cloudy suspensions indicated growth or increase in biomass whereas clear suspensions indicate no growth or no increase in biomass. A deficiency or lack of growth correlates to the effectiveness of the antimicrobial particles. Optical densities where monitored using a spectrophotometer such as an Eppendorf Bio Photometer cuvette reader (Eppendorf North America, Inc, Enfield, Conn.) or Biotek Synergy 2 multiwell plate reader (Biotek Inc., Winooski, Vt.).

5) Determination of Activity Against Bacterial Spore Germination.

Preparation of spores. One-liter cultures were grown in Erlenmeyer flasks containing trypticase soy broth (TSB; Difco, Sparks, Md.) inoculated with exponential-phase cells from trypticase soy precultures. The cultures were incubated at 37° C. on a rotary shaker at 200 rpm. Spore development was visualized by phase contrast microscopy. The cultures were harvested after 72 hours. All harvesting and washing procedures were performed at 25° C. Spores were harvested by centrifugation and resuspended with one quarter culture volume of a solution containing 1M KCL and 0.5M NaCl. Centrifugation was repeated and cultures were resuspended in one tenth culture volume of 50 mM Tris-HCL (pH 7.2) containing 1 mg lysozyme per milliliter. Cell suspensions were then incubated at 37° C. for 1 hour followed by alternate centrifugation and washing with 1M NaCl, deionized water, 0.05% sodium dodecyl sulfate (SDS), 50 mM Tris-HCl, pH 7.2; 10 mM EDTA and three additional wash steps in deionized water. Spore suspensions were heat-shocked at 80° C. for 10 min and stored at 4° C. until use (Nicholson, W. L. and P. Setlow, 1990. Sporulation, germination, and outgrowth. pp. 391-450. In Harwood, C R and Cutting, S M (eds.) Molecular biological methods for *Bacillus*. John Wiley & Sons, New York).

Germination assay. Two milliliter polypropylene tubes were inoculated with *B. cereus* spore suspensions treated with approximately 2 µM or 59 ppm of nanoparticles for 24 hours at room temperature. After 24 hours of incubation, suspensions were pelleted by centrifugation at 13,000×g, and the supernatant removed and discarded. Pellets were resuspended in 200 µl of TSB. The tubes were then incubated for 24 hours at 25° C. and 37° C. Germination characteristics of *B. cereus* spores after 24 hours of incubation with nanoparticle chemistries were determined by optical density (Eppendorf Bio Photometer) at a wavelength of 600 nm (OD600).

Example 43

Antimicrobial Effectiveness of Particle Suspensions Against Target Microbes

The results listed above do not cover each and every variation of the materials used in Tables 2 through 9. The formula numbers are only a guide to correlate the samples among these tables. All the samples in these tables were made by PROCEDURE SET 1 (Examples 1 through 20).

For purposes of illustration, Formula #E33$_B$ in Table 2 comprises a mixture of different functionalized metal halide particles including silver iodide and copper bromide, where the particles are surface modified with PVP and then TGN. This particular formula was made using the process of Example 16. Since in this formulation silver is 5.6 ppm in excess of the iodide, the silver stoichiometry was 56% more as compared to the sodium iodide salt.

In all cases for testing against microbes, the solutions were diluted so as to result in 10 ppm silver metal concentration unless mentioned otherwise.

This example reflects the testing of a variety of binary mixed metal halide particle compositions and their efficacy against seven different pathogenic species. The results obtained from evaluating the antimicrobial effectiveness of a range of particles prepared with different chemistries and surface modifications against target microbes are presented in Tables 2-9 for the following microbes: *E. coli* (ATCC 15579), Table 2; *P. aeruginosa* (ATCC 27313), Table 3; *M. fortuitum* (ATCC 6841), Table 4; *S. aureus* (ATCC 25923), Table 5; *E. faecalis* (ATCC 19433), Table 6; Copper-resistant *E. coli* (77-30013-2), Table 7; MS2 colliphage (ATCC 15597-B1), Table 8; Poliovirus (PV-1, LSc-2ab), Table 9.

The abbreviations used in the following tables are as follows:

Amino Acid Modifiers column: Leu=Leucine; Lys=Lysine; Asp=Aspartic acid; PVP=Polyvinylpyrrolidone. Thiol Modifier Column: AT=Aminothiol; TGO=Thioglycerol; TGN=Thioglycine; TLA=Thiolactic acid; TMA=Thiomalic acid; TOA=Thiooctic acid; TS=Thiosilane.

Subscripts for Formula Numbers: R#=repeat test with same sample for the "#" time, i.e. R1 is the 1$^{st}$ repeat of this sample. Letters other than "R" indicate a sample that has been remade, i.e. A is the first remake, B is the second remake, etc.

The headers in Tables 2-9 are explained as follows: "Formula #" refers to an internal tracking number; "1° Constituent (% weight)" refers to the metal constituent and to its weight percent in the first metal halide particle; "1° Halogen" refers to the halogen in the primary metal halide salt particle; "2° Constituent" refers to the metal constituent in the second metal halide particle; "2° Halogen" refers to the halogen in the second metal halide salt particle; "AA Modifier (Ag:AA, in mol)" refers to the amino acid or polymer, if any, used to stabilize the particle(s) in solution, and its silver to amino acid/polymer ratio in moles; "Thiol modifier (Ag: SH)" refers to the thiol modifier used to stabilize the particle(s) in water, and the ratio of silver to thiol in moles; "Exposure time" is the time (usually stated in hours) that a bacterial sample was exposed to a test article coated with a composition of the present invention; "Log$_{10}$" is the resulting reduction in the number of bacterial counts versus a control, on a logarithmic scale.

TABLE 2

Nanoparticle Results against *Escherichia coli* (ATCC 15597)

| Formula # | 1° Constituent (% weight) | 1° Halogen | 2° Constituent * | 2° Halogen | AA Modifier (Ag:AA) | Thiol Modifier (Ag:SH) | Exposure Time (hours) | Log$_{10}$ |
|---|---|---|---|---|---|---|---|---|
| E-30$_B$ | Ag (0.50%) ex: 5.6 ppm | I | Cu (5.0%) | Br | PVP(1:2.5) | — | 5 | 3.57 |
| E-33$_B$ | Ag (0.50%) ex: 5.6 ppm | I | Cu (5.0%) | Br | PVP(1:2.5) | TGN (1:0.50) | 5 | 4.32 |
| H-02$_B$ | Ag (0.50%) | Br | Cu (5.0%) ex: 0.15 ppm | I | PVP(1:2.5) | — | 5 | >4.80 |
| H-04$_A$ | Ag (0.50%) | Br | Cu (5.0%) ex: 0.15 ppm | I | PVP(1:2.5) | TGN (1:0.50) | 5 | 3.80 |

*2° Constituent metal concentration is given in relative molar percentage based on silver moles from 1° constituent (e.g., Ag 0.5%, Cu 5% means formulation has 0.5Wt % silver and the copper/silver ratio is 5%. Before use the formulation is diluted to 10 ppm silver, unless mentioned otherwise.)

Table 2 contains the numbers of *E. coli* bacteria after exposure for 5 hours to selected combinations of the functionalized particles, which are seen to decrease by more than 4 logs (i.e., fewer than 1 microbe in 10,000 survive). Specifically, Formulae E-33$_B$, a combination of AgI and CuBr particles functionalized with PVP and TGN show a 4.32 log$_{10}$ reduction in *E. coli*. Also, Formula H-02$_B$, a combination of AgBr/CuI particles functionalized with PVP only, showed the single highest *E. coli* reduction, a greater than 4.8 log$_{10}$ reduction.

TABLE 3

Nanoparticle Results against *Pseudomonas aeruginosa* (ATCC 27313)

| Formula # | 1° Constituent (% weight) | 1° Halogen | 2° Constituent * | 2° Halogen | AA Modifier (Ag:AA) | Thiol Modifier (Ag:SH) | Exposure Time (hours) | Log$_{10}$ |
|---|---|---|---|---|---|---|---|---|
| D-02 | Ag (0.50%) | Br | Cu (2.5%) | Br | Asp (1:2) | TGN (1:0.50) | 5 | 3.42 |
| D-03 | Ag (0.50%) | Br | Cu (2.5%) | Br | Asp (1:2) | TLA (1:0.50) | 5 | 2.18 |
| D-04 | Ag (0.50%) | Br | Cu (2.5%) | Br | Asp (1:2) | TMA (1:0.50) | 5 | 2.60 |
| D-07 | Ag (0.50%) | I | Cu (2.5%) | Br | Asp (1:2) | TGN (1:0.50) | 5 | 2.42 |
| D-08 | Ag (0.50%) | I | Cu (2.5%) | Br | Asp (1:2) | TLA (1:0.50) | 5 | 3.21 |
| D-09 | Ag (0.50%) | I | Cu (2.5%) | Br | Asp (1:2) | TMA (1:0.50) | 5 | 4.12 |
| D-09$_{R1}$ | Ag (0.50%) | I | Cu (2.5%) | Br | Asp (1:2) | TMA (1:0.50) | 5 | 2.16 |
| D-12 | Ag (0.50%) | Br | Cu (5.0%) | Br | Asp (1:2) | TGN (1:0.50) | 5 | 3.62 |
| D-17 | Ag (0.50%) | I | Cu (5.0%) | Br | Asp (1:2) | TGN (1:0.50) | 5 | 3.86 |
| D-17$_{R1}$ | Ag (0.50%) | I | Cu (5.0%) | Br | Asp (1:2) | TGN (1:0.50) | 5 | 4.35 |
| D-18 | Ag (0.50%) | I | Cu (5.0%) | Br | Asp (1:2) | TLA (1:0.50) | 5 | 3.20 |
| D-19 | Ag (0.50%) | I | Cu (5.0%) | Br | Asp (1:2) | TMA (1:0.50) | 5 | 4.20 |
| D-19$_{R1}$ | Ag (0.50%) | I | Cu (5.0%) | Br | Asp (1:2) | TMA (1:0.50) | 5 | 3.81 |
| E-05 | Ag (0.50%) | Br | Cu (10.0%) | Br | PVP (1:2.5) | — | 5 | >5.65 |
| E-06 | Ag (0.50%) | Br | Cu (15.0%) | Br | PVP (1:2.5) | — | 5 | >5.65 |
| E-07 | Ag (0.50%) | Br | Cu (2.5%) | Br | PVP (1:2.5) | — | 5 | 2.11 |
| E-08 | Ag (0.50%) | Br | Cu (2.5%) | Br | PVP (1:2.5) | TGO (1:0.50) | 5 | 2.66 |
| E-09 | Ag (0.50%) | Br | Cu (2.5%) | Br | PVP (1:2.5) | TGN (1:0.50) | 5 | 2.53 |
| E-10 | Ag (0.50%) | Br | Cu (2.5%) | Br | PVP (1:2.5) | TLA (1:0.50) | 5 | 2.42 |
| E-11 | Ag (0.50%) | Br | Cu (2.5%) | Br | PVP (1:2.5) | TMA (1:0.50) | 5 | 2.08 |
| E-12 | Ag (0.50%) | Br | Cu (5.0%) | Br | PVP (1:2.5) | — | 5 | 2.49 |
| E-13 | Ag (0.50%) | Br | Cu (5.0%) | Br | PVP (1:2.5) | TGO (1:0.50) | 5 | 3.06 |
| E-14 | Ag (0.50%) | Br | Cu (5.0%) | Br | PVP (1:2.5) | TGN (1:0.50) | 5 | 3.45 |
| E-15 | Ag (0.50%) | Br | Cu (5.0%) | Br | PVP (1:2.5) | TLA (1:0.50) | 5 | 3.33 |
| E-16 | Ag (0.50%) | Br | Cu (5.0%) | Br | PVP (1:2.5) | TMA (1:0.50) | 5 | 3.19 |
| E-17 | Ag (0.50%) | I | Cu (10.0%) | Br | PVP (1:2.5) | — | 5 | 5.05 |
| E-18 | Ag (0.50%) | I | Cu (15.0%) | Br | PVP (1:2.5) | — | 5 | >5.65 |
| E-19 | Ag (0.50%) | I | Cu (5.0%) | Br | PVP (1:2.5) | — | 5 | 4.54 |
| E-20 | Ag (0.50%) | I | Cu (5.0%) | Br | PVP (1:2.5) | TGO (1:0.50) | 5 | 3.54 |
| E-21 | Ag (0.50%) | I | Cu (5.0%) | Br | PVP (1:2.5) | TGN (1:0.10) | 5 | 3.85 |
| E-22 | Ag (0.50%) | I | Cu (5.0%) | Br | PVP (1:2.5) | TGN (1:0.50) | 5 | 4.19 |
| E-23 | Ag (0.50%) | I | Cu (5.0%) | Br | PVP (1:2.5) | TLA (1:0.50) | 5 | 3.22 |
| E-24 | Ag (0.50%) | I | Cu (5.0%) | Br | PVP (1:2.5) | TMA (1:0.50) | 5 | 2.77 |
| E-25 | Ag (0.50%) ex: 6.3 ppm | I | Cu (2.5%) | Br | PVP (1:2.5) | — | 5 | 4.51 |
| E-25$_{R1}$ | Ag (0.50%) ex: 6.3 ppm | I | Cu (2.5%) | Br | PVP (1:2.5) | — | 5 | 5.53 |
| E-26 | Ag (0.50%) ex: 6.3 ppm | I | Cu (2.5%) | Br | PVP (1:2.5) | TGO (1:0.50) | 5 | >5.76 |
| E-26$_{R1}$ | Ag (0.50%) ex: 6.3 ppm | I | Cu (2.5%) | Br | PVP (1:2.5) | TGO (1:0.50) | 5 | 5.53 |
| E-26$_{R1}$ | Ag (0.50%) ex: 6.3 ppm | I | Cu (2.5%) | Br | PVP (1:2.5) | TGO (1:0.50) | 3 | 2.02 |
| E-27 | Ag (0.50%) ex: 6.3 ppm | I | Cu (2.5%) | Br | PVP (1:2.5) | TGN (1:0.50) | 5 | >5.76 |
| E-27$_{R1}$ | Ag (0.50%) ex: 6.3 ppm | I | Cu (2.5%) | Br | PW (1:2.5) | TGN (1:0.50) | 5 | 5.53 |
| E-27$_{R1}$ | Ag (0.50%) ex: 6.3 ppm | I | Cu (2.5%) | Br | PVP (1:2.5) | TGN (1:0.50) | 3 | 3.97 |
| E-28 | Ag (0.50%) ex: 6.3 ppm | I | Cu (2.5%) | Br | PVP (1:2.5) | TLA (1:0.50) | 5 | 2.74 |
| E-29 | Ag (0.50%) ex: 6.3 ppm | I | Cu (2.5%) | Br | PVP (1:2.5) | TMA (1:0.50) | 5 | 5.28 |
| E-29$_{R1}$ | Ag (0.50%) ex: 6.3 ppm | I | Cu (2.5%) | Br | PVP (1:2.5) | TMA (1:0.50) | 5 | 2.48 |
| E-30 | Ag (0.50%) ex: 5.6 ppm | I | Cu (5.0%) | Br | PVP (1:2.5) | — | 5 | >5.76 |
| E-30$_A$ | Ag (0.50%) ex: 5.6 ppm | I | Cu (5.0%) | Br | PVP (1:2.5) | — | 5 | 4.42 |
| E-30$_B$ | Ag (0.50%) ex: 5.6 ppm | I | Cu (5.0%) | Br | PVP (1:2.5) | — | 5 | 5.32 |
| E-30$_{R1}$ | Ag (0.50%) ex: 5.6 ppm | I | Cu (5.0%) | Br | PVP (1:2.5) | — | 5 | >5.53 |
| E-30$_{R1}$ | Ag (0.50%) ex: 5.6 ppm | I | Cu (5.0%) | Br | PVP (1:2.5) | — | 3 | 2.17 |

TABLE 3-continued

Nanoparticle Results against *Pseudomonas aeruginosa* (ATCC 27313)

| Formula # | 1° Constituent (% weight) | 1° Halogen | 2° Constituent * | 2° Halogen | AA Modifier (Ag:AA) | Thiol Modifier (Ag:SH) | Exposure Time (hours) | $Log_{10}$ |
|---|---|---|---|---|---|---|---|---|
| E-31 | Ag (0.50%) ex: 5.6 ppm | I | Cu (5.0%) | Br | PVP (1:2.5) | TGO (1:0.50) | 5 | 5.46 |
| E-31$_{R1}$ | Ag (0.50%) ex: 5.6 ppm | I | Cu (5.0%) | Br | PVP (1:2.5) | TGO (1:0.50) | 5 | 3.75 |
| E-33 | Ag (0.50%) ex: 5.6 ppm | I | Cu (5.0%) | Br | PVP (1:2.5) | TGN (1:0.50) | 5 | 5.16 |
| E-33$_A$ | Ag (0.50%) ex: 5.6 ppm | I | Cu (5.0%) | Br | PVP (1:2.5) | TGN (1:0.50) | 5 | 5.20 |
| E-33$_B$ | Ag (0.50%) ex: 5.6 ppm | I | Cu (5.0%) | Br | PVP (1:2.5) | TGN (1:0.50) | 5 | 5.06 |
| E-33$_C$ | Ag (0.50%) ex: 5.6 ppm | I | Cu (5.0%) | Br | PVP (1:2.5) | TGN (1:0.50) | 5 | >5.30 |
| E-33$_{R1}$ | Ag (0.50%) ex: 5.6 ppm | I | Cu (5.0%) | Br | PVP (1:2.5) | TGN (1:0.50) | 5 | >5.53 |
| E-33$_{R1}$ | Ag (0.50%) ex: 5.6 ppm | I | Cu (5.0%) | Br | PVP (1:2.5) | TGN (1:0.50) | 3 | 4.25 |
| E-34 | Ag (0.50%) ex: 5.6 ppm | I | Cu (5.0%) | Br | PVP (1:2.5) | TLA (1:0.50) | 5 | 3.53 |
| E-35 | Ag (0.50%) ex: 5.6 ppm | I | Cu (5.0%) | Br | PVP (1:2.5) | TMA (1:0.50) | 5 | 5.46 |
| E-35$_{R1}$ | Ag (0.50%) ex: 5.6 ppm | I | Cu (5.0%) | Br | PVP (1:2.5) | TMA (1:0.50) | 5 | 4.75 |
| F-01 | Ag (0.50%) | Br | Cu (2.5%) ex: 0.074 ppm | I | PVP (1:2.5) | — | 5 | 4.09 |
| F-02 | Ag (0.50%) ex: 0.194 ppm | Br | Cu (5.0%) ex: 0.15 ppm | I | PVP (1:2.5) | — | 5 | >5.65 |
| F-03 | Ag (0.50%) ex: 0.5 ppm | Br | Cu (10.0%) ex: 0.3 ppm | I | PVP (1:2.5) | — | 5 | >5.65 |
| F-06 | Ag (0.50%) ex: 0.5 ppm | I | Cu (10.0%) ex: 0.3 ppm | I | PVP (1:2.5) | — | 5 | 4.81 |
| G-01 | Cu (0.50%) ex: 5 ppm | I | — | — | PVP (1:2.5) | — | 5 | 5.35 |
| H-01 | Ag (0.50%) | Br | Cu (2.5%) ex: 0.074 ppm | I | PVP (1:2.5) | — | 5 | 4.40 |
| H-02 | Ag (0.50%) | Br | Cu (5.0%) ex: 0.15 ppm | I | PVP (1:2.5) | — | 5 | >5.65 |
| H-02$_A$ | Ag (0.50%) | Br | Cu (5.0%) ex: 0.15 ppm | I | PVP (1:2.5) | — | 5 | 5.50 |
| H-02$_B$ | Ag (0.50%) | Br | Cu (5.0%) ex: 0.15 ppm | I | PVP (1:2.5) | — | 5 | 5.60 |
| H-04 | Ag (0.50%) | Br | Cu (5.0%) ex: 0.15 ppm | I | PVP (1:2.5) | TGN (1:0.50) | 5 | 5.50 |
| H-04$_A$ | Ag (0.50%) | Br | Cu (5.0%) ex: 0.15 ppm | I | PVP (1:2.5) | TGN (1:0.50) | 5 | 3.92 |
| H-04$_B$ | Ag (0.50%) | Br | Cu (5.0%) ex: 0.15 ppm | I | PVP (1:2.5) | TGN (1:0.50) | 5 | 5.00 |
| H-05 | Ag (0.50%) | Br | Cu (10.0%) ex: 0.3 ppm | I | PVP (1:2.5) | — | 5 | 5.65 |
| H-06 | Ag (0.50%) | Br | Cu (5.0%) | I | PVP (1:2.5) | — | 5 | >5.30 |
| H-07 | Ag (0.50%) | Br | Cu (5.0%) | I | PVP (1:2.5) | TGN (1:0.50) | 5 | 4.46 |
| I-1 | Cu (0.50%) | I | — | — | PVP (1:2.5) | — | 5 | >5.30 |
| X-01 | Ag (0.50%) | Br | Cu (5.0%) | I | PVP (1:2.5) | — | 5 | 5.20 |
| X-02 | Ag (0.50%) | Br | Cu (15.0%) | I | PVP (1:2.5) | — | 5 | 5.50 |
| X-03 | Ag (0.50%) | Br | Cu2+ (5.0%) ex: 0.15 ppm | I | PVP (1:2.5) | — | 5 | 4.60 |
| X-04 | Ag (0.50%) | Br | Cu2+ (15.0%) ex: 0.45 ppm | I | PVP (1:2.5) | — | 5 | 4.46 |

Table 3 shows selected results of combinations of functionalized metal halide particles against *P. aeruginosa*. Surprisingly, there are twenty-nine different combinations of silver halide and copper halide particles that exhibited at least 5 $log_{10}$ reduction over the test period of 5 hours. Considering the results on *P. aeruginosa*, it is seen that functionalized silver halide-copper halide nanoparticle combinations are notably more effective in killing the microbes than functionalized silver metal nanoparticles alone. Functionalized silver metal nanoparticles alone showed no more than 0.93 $log_{10}$ reduction, functionalized silver bromide particles 3.68 $log_{10}$, and functionalized silver iodide particles 0.97 $log_{10}$ (data not shown). Silver chloride nanoparticles, with the exception of Formula A-07 (not shown) did not have much effect on *P. aeruginosa*. It is also seen that combinations of functionalized silver halide particles with functionalized copper halide particles are more effective than functionalized silver halide particles alone, given the twenty-nine results in excess of 5 $log_{10}$ reduction. It is further seen that combinations of functionalized silver halide particles with functionalized copper halide particles where the halides are different on the two cations provide further enhanced antimicrobial effectiveness. It is noteworthy that two examples of CuI-PVP, Formulae G-01 and I-1, recorded a 5.35 and 5.30, respectively, $log_{10}$ reduction without any silver halide co-particle.

TABLE 4

Nanoparticle Results against *Mycobacterium fortuitum* (ATCC 6841)

| Formula # | 1° Constituent (% weight) | 1° Halogen | 2° Constituent * | 2° Halogen | AA Modifier (Ag:AA) | Thiol Modifier (Ag:SH) | Exposure Time (hours) | $Log_{10}$ |
|---|---|---|---|---|---|---|---|---|
| E-19$_A$ | Ag (0.50%) | I | Cu (5.0%) | Br | PVP (1:2.5) | — | 48 | 2.62 |
| E-22$_A$ | Ag (0.50%) | I | Cu (5.0%) | Br | PVP (1:2.5) | TGN (1:0.50) | 48 | 2.84 |
| E-30$_B$ | Ag (0.50%) | I | Cu (5.0%) | Br | PVP (1:2.5) | — | 48 | 2.73 |
|  | ex: 5.6 ppm |  |  |  |  |  |  |  |
| E-30$_C$ | Ag (0.50%) | I | Cu (5.0%) | Br | PVP (1:2.5) | — | 48 | 4.41 |
|  | ex: 5.6 ppm |  |  |  |  |  |  |  |
| E-30$_C$ | Ag (0.50%) | I | Cu (5.0%) | Br | PVP (1:2.5) | — | 18 | 2.58 |
|  | ex: 5.6 ppm |  |  |  |  |  |  |  |
| E-33$_B$ | Ag (0.50%) | I | Cu (5.0%) | Br | PVP (1:2.5) | TGN (1:0.50) | 48 | 4.73 |
|  | ex: 5.6 ppm |  |  |  |  |  |  |  |
| E-33$_C$ | Ag (0.50%) | I | Cu (5.0%) | Br | PVP (1:2.5) | TGN (1:0.50) | 48 | 3.84 |
|  | ex: 5.6 ppm |  |  |  |  |  |  |  |
| E-33$_C$ | Ag (0.50%) | I | Cu (5.0%) | Br | PVP (1:2.5) | TGN (1:0.50) | 18 | 2.31 |
|  | ex: 5.6 ppm |  |  |  |  |  |  |  |
| F-05$_A$ | Ag (0.50%) | I | Cu (5.0%) | I | PVP (1:2.5) | — | 48 | 3.05 |
|  | ex: 0.194 ppm |  | ex: 0.15 ppm |  |  |  |  |  |
| F-05$_B$ | Ag (0.50%) | I | Cu (5.0%) | I | PVP (1:2.5) | — | 48 | 4.19 |
|  | ex: 0.194 ppm |  | ex: 0.15 ppm |  |  |  |  |  |
| F-05$_B$ | Ag (0.50%) | I | Cu (5.0%) | I | PVP (1:2.5) | — | 18 | 2.10 |
|  | ex: 0.194 ppm |  | ex: 0.15 ppm |  |  |  |  |  |
| G-01$_B$ | Cu (0.50%) | I | — | — | PVP (1:2.5) | — | 48 | 2.07 |
|  | ex: 5 ppm |  |  |  |  |  |  |  |
| H-02$_B$ | Ag (0.50%) | Br | Cu (5.0%) | I | PVP (1:2.5) | — | 48 | 4.73 |
|  |  |  | ex: 0.15 ppm |  |  |  |  |  |
| H-02$_C$ | Ag (0.50%) | Br | Cu (5.0%) | I | PVP (1:2.5) | — | 18 | 3.17 |
|  |  |  | ex: 0.15 ppm |  |  |  |  |  |
| H-02$_C$ | Ag (0.50%) | Br | Cu (5.0%) | I | PVP (1:2.5) | — | 48 | 2.89 |
|  |  |  | ex: 0.15 ppm |  |  |  |  |  |
| H-04$_A$ | Ag (0.50%) | Br | Cu (5.0%) | I | PVP (1:2.5) | TGN (1:0.50) | 48 | 4.13 |
|  |  |  | ex: 0.15 ppm |  |  |  |  |  |
| H-04$_B$ | Ag (0.50%) | Br | Cu (5.0%) | I | PVP (1:2.5) | TGN (1:0.50) | 18 | 2.81 |
|  |  |  | ex: 0.15 ppm |  |  |  |  |  |
| H-04$_B$ | Ag (0.50%) | Br | Cu (5.0%) | I | PVP (1:2.5) | TGN (1:0.50) | 48 | 2.59 |
|  |  |  | ex: 0.15 ppm |  |  |  |  |  |
| H-06 | Ag (0.50%) | Br | Cu (5.0%) | I | PVP (1:2.5) | — | 48 | 3.45 |
| H-06 | Ag (0.50%) | Br | Cu (5.0%) | I | PVP (1:2.5) | — | 18 | 2.84 |
| I-1 | Cu (0.50%) | I | — | — | PVP (1:2.5) | — | 48 | 2.31 |

Table 4 shows the results of testing functionalized metal halide particles against *M. fortuitum*. The results shown in Table 4 for *M. fortuitum* indicate remarkable killing efficiency, with five examples of reductions in bacterial populations greater than 4 logs in 48 hours. (Since mycobacteria are known to undergo mitosis at a much slower rate than conventional bacteria, the exposure times for *M. fortuitum* were longer than those for *P. aeruginosa* or *E. coli*.) These results on *M. fortuitum* suggest that the present functionalized particles would also be effective against *M. tuberculosis*, and even against *M. tuberculosis* which is resistant to conventional antibiotics—since the mechanism of antimicrobial activity of the present antimicrobial agents is very different from the antimicrobial mechanisms of conventional antibiotics. Notably, the CuI particles alone were inferior to the combinations, suggesting a synergistic effect between the silver halide and copper halide particles.

TABLE 5

| Nanoparticle Results against *Staphylococcus aureus* (ATCC 25923) | | | | | | | | |
|---|---|---|---|---|---|---|---|---|
| Formula # | 1° Constituent (% weight) | 1° Halogen | 2° Constituent * | 2° Halogen | AA Modifier (Ag:AA) | Thiol Modifier (Ag:SH) | Exposure Time (hours) | $Log_{10}$ |
| E-$19_A$ | Ag (0.50%) | I | Cu (5.0%) | Br | PVP (1:2.5) | — | 24 | 3.76 |
| E-$22_A$ | Ag (0.50%) | I | Cu (5.0%) | Br | PVP (1:2.5) | TGN (1:0.50) | 24 | 2.74 |
| E-$30_C$ | Ag (0.50%) ex: 5.6 ppm | I | Cu (5.0%) | Br | PVP (1:2.5) | — | 24 | >5.19 |
| E-$33_C$ | Ag (0.50%) ex: 5.6 ppm | I | Cu (5.0%) | Br | PVP (1:2.5) | TGN (1:0.50) | 24 | 3.66 |
| H-$02_C$ | Ag (0.50%) | Br | Cu (5.0%) ex: 0.15 ppm | I | PVP (1:2.5) | — | 24 | 2.94 |

Table 5 shows the results of testing functionalized metal halide particles against *S. aureus*. Fewer investigations were carried out on the antimicrobial effectiveness of the functionalized particles against Gram-positive bacteria, the results obtained against *S. aureus* shown here are nevertheless encouraging, with reductions in bacterial populations greater than 5 logs in 24 hours having been obtained (Formula E-30$_C$, AgI/CuBr-PVP, >5.19 log$_{10}$).

TABLE 6

Nanoparticle Results against *Enterococcus faecalis* (ATCC 19433)

| Formula # | 1° Constituent (% weight) | 1° Halogen | 2° Constituent * | 2° Halogen | AA Modifier (Ag:AA) | Thiol Modifier (Ag:SH) | Exposure Time (hours) | Log$_{10}$ |
|---|---|---|---|---|---|---|---|---|
| E-19$_A$ | Ag (0.50%) | I | Cu (5.0%) | Br | PVP (1:2.5) | — | 24 | 2.19 |
| E-30$_C$ | Ag (0.50%) ex: 5.6 ppm | I | Cu (5.0%) | Br | PVP (1:2.5) | — | 24 | 2.47 |
| E-33$_C$ | Ag (0.50%) ex: 5.6 ppm | I | Cu (5.0%) | Br | PVP (1:2.5) | TGN (1:0.50) | 24 | >5.24 |
| E-33$_C$ | Ag (0.50%) ex: 5.6 ppm | I | Cu (5.0%) | Br | PVP (1:2.5) | TGN (1:0.50) | 5 | 2.53 |
| F-05$_B$ | Ag (0.50%) ex: 0.194 ppm | I | Cu (5.0%) ex: 0.15 ppm | I | PVP (1:2.5) | — | 24 | 2.14 |
| G-01$_B$ | Cu (0.50%) ex: 5 ppm | I | — | — | PVP (1:2.5) | — | 24 | >5.24 |
| G-01$_B$ | Cu (0.50%) ex: 5 ppm | I | — | — | PVP (1:2.5) | — | 5 | 2.59 |
| H-02$_C$ | Ag (0.50%) | Br | Cu (5.0%) ex: 0.15 ppm | I | PVP (1:2.5) | — | 24 | 2.39 |
| H-04$_B$ | Ag (0.50%) | Br | Cu (5.0%) ex: 0.15 ppm | I | PVP (1:2.5) | TGN (1:0.50) | 24 | >5.24 |
| H-04$_B$ | Ag (0.50%) | Br | Cu (5.0%) ex: 0.15 ppm | I | PVP (1:2.5) | TGN (1:0.50) | 5 | 2.90 |

Table 6 shows the results of testing functionalized metal halide particles against *E. faecallis*. From the results it is apparent that the present functionalized particles are even effective against enterococci. As seen in the table, reductions in bacterial populations greater than 5 log$_{10}$ in 24 hours have been obtained using combinations of functionalized particles. Specifically, E-33$_C$ (AgI/CuBr-PVP-TON), and H-04$_B$ (AgBr/CuI-PVP-TON). The copper iodide example, G-01$_B$ (CuI-PVP) matched or exceeded the silver halide/copper halide combinations.

TABLE 7

Nanoparticle Results against Copper Resistant *Escherichia coli*

| Formula # | 1° Constituent (% weight) | 1° Halogen | 2° Constituent * | 2° Halogen | AA Modifier (Ag:AA) | Thiol Modifier (Ag:SH) | Exposure Time (hours) | Log$_{10}$ |
|---|---|---|---|---|---|---|---|---|
| E-33$_C$ | Ag (0.50%) ex: 5.6 ppm | I | Cu (5.0%) | Br | PVP (1:2.5) | TGN (1:0.50) | 5 | 2.93 |
| H-04$_B$ | Ag (0.50%) | Br | Cu (5.0%) ex: 0.15 ppm | I | PVP (1:2.5) | TGN (1:0.50) | 5 | 2.35 |

Table 7 shows the results of testing functionalized metal halide particles against copper-resistant *E. coli*. When tested against the microbes, reductions in bacterial populations approaching 3 logs have been obtained in 5 hours using combinations of the present functionalized particles (see Table 7). Specifically, almost three logs of reduction 99.9% (log$_{10}$ 2.93) was obtained with Formula E-33C (AgI/CuBr-PVP-TGN).

TABLE 8

Nanoparticle Results against MS2 coliphage (ATCC 15597-B1)

| Formula # | 1° Constituent (% weight) | 1° Halogen | 2° Constituent * | 2° Halogen | AA Modifier (Ag:AA) | Thiol Modifier (Ag:SH) | Exposure Time (hours) | $Log_{10}$ |
|---|---|---|---|---|---|---|---|---|
| A-04$_C$ | Ag (0.50%) | Br | — | — | Asp (1:2) | TMA (1:0.25) | 24 | 5.28 |
| A-07$_A$ | Ag (0.50%) | Cl | — | — | Asp (1:2) | TGN (1:0.50) | 24 | 4.08 |
| D-02$_A$ | Ag (0.50%) | Br | Cu (2.5%) | Br | Asp (1:2) | TGN (1:0.50) | 24 | 2.63 |
| D-09$_A$ | Ag (0.50% | I | Cu (2.5%) | Br | Asp (1:2) | TMA (1:0.50) | 24 | >5.28 |
| D-17$_A$ | Ag (0.50%) | I | Cu (5.0%) | Br | Asp (1:2) | TGN (1:0.50) | 24 | >5.28 |
| D-19$_A$ | Ag (0.50%) | I | Cu (5.0%) | Br | Asp (1:2) | TMA (1:0.50) | 24 | >5.28 |
| E-06$_A$ | Ag (0.50%) | Br | Cu (15.0%) | Br | PVP (1:2.5) | — | 24 | 2.20 |
| E-27$_A$ | Ag (0.50%) ex: 6.3 ppm | I | Cu (2.5%) | Br | PVP (1:2.5) | TGN (1:0.50) | 24 | >4.07 |
| E-29$_A$ | Ag (0.50%) ex: 6.3 ppm | I | Cu (2.5%) | Br | PVP (1:2.5) | TMA (1:0.50) | 24 | >4.07 |
| E-33$_D$ | Ag (0.50%) ex: 5.6 ppm | I | Cu (5.0%) | Br | PVP (1:2.5) | TGN (1:0.50) | 24 | >4.07 |
| E-35$_A$ | Ag (0.50%) ex: 5.6 ppm | I | Cu (5.0%) | Br | PVP (1:2.5) | TMA (1:0.50) | 24 | >4.07 |
| G-01$_B$ | Cu (0.50%) ex: 5 ppm | I | — | — | PVP (1:2.5) | — | 24 | >4.07 |
| G-01$_C$ | Cu (0.50%) ex: 5 ppm | I | — | — | PVP (1:2.5) | — | 24 | >5.25 |
| H-01$_A$ | Ag (0.50%) | Br | Cu (2.5%) ex: 0.074 ppm | I | PVP (1:2.5) | — | 24 | 4.01 |
| H-02$_D$ | Ag (0.50%) | Br | Cu (5.0%) ex: 0.15 ppm | I | PVP (1:2.5) | — | 24 | 4.65 |
| H-04$_C$ | Ag (0.50%) | Br | Cu (5.0%) ex: 0.15 ppm | I | PVP (1:2.5) | TGN (1:0.50) | 24 | >5.25 |
| H-05$_A$ | Ag (0.50%) | Br | Cu (10.0%) ex: 0.3 ppm | I | PVP (1:2.5) | — | 24 | 5.25 |
| I-1 | Cu (0.50%) | I | — | — | PVP (1:2.5) | — | 24 | >4.07 |
| X-03$_A$ | Ag (0.50%) | Br | Cu2+ (5.0%) ex: 0.15 ppm | I | PVP (1:2.5) | — | 24 | 3.31 |
| X-04$_A$ | Ag (0.50%) | Br | Cu2+ (15.0%) ex: 0.45 ppm | I | PVP (1:2.5) | — | 24 | >5.25 |

Table 8 shows the results of testing functionalized metal halide particles against a different genus, that of bacteriophage. Bacteriophage are viruses that attack bacteria. Results of the functionalized metal halide particles against MS2 coliphage are shown in Table 8. The present functionalized particles were tested against bacteriophage to evaluate their potential effectiveness against viruses without the necessity of testing involving cell culture. As seen in Table 8, combinations of the present functionalized particles were found to be highly effective in decreasing the microbial populations of this bacteriophage, with decreases exceeding 5 logs in 24 hours being obtained.

The testing carried out on Poliovirus, some of which are shown in Table 9, were likewise encouraging although not as dramatic as the results obtained on the bacteriophage. Functionalized CuI particles were found to be particularly effective against poliovirus, with decreases in microbial populations greater than 3 logs being found in 24 hours. A further encouraging result of the testing on poliovirus was the observation of the cell culture work carried out here, which showed no adverse effect of the functionalized particles on cell viability and reproduction in culture.

It is seen from the data in Tables 2-9 that remarkable decreases in bacterial populations can be obtained using func-

TABLE 9

Nanoparticle Results against Poliovirus (PV-1 LSc-2ab)

| Formula # | 1° Constituent (% weight) | 1° Halogen | 2° Constituent * | 2° Halogen | AA Modifier (Ag:AA) | Thiol Modifier (Ag:SH) | Exposure Time (hours) | $Log_{10}$ |
|---|---|---|---|---|---|---|---|---|
| G-01$_B$ | Cu (0.50%) ex: 5 ppm | I | — | — | PVP (1:2.5) | — | 24 | 2.00 |
| G-01$_C$ | Cu (0.50%) ex: 5 ppm | I | — | — | PVP (1:2.5) | — | 24 | 2.56 |
| I-1 | Cu (0.50%) | I | — | — | PVP (1:2.5) | — | 24 | 3.11 | tionalized nanoparticles comprising embodiments of the invention including metal halides. Since among Gram-negative bacteria, *P. aeruginosa* is generally more difficult to kill than *E. coli*, more data were presented for *P. aeruginosa*.

Example 44

Evaluation of Effectiveness of Functionalized Silver Halide, Modified Silver Halide and Mixed-Metal Halide Nanoparticles Against *B. cereus* Spores All previously-mentioned chemicals are incorporated by reference herein.

a) Preparation of Stock Solutions and Sols:

1% alanine-solution

1% w/w aqueous solution of Alanine was made by dissolving 0.05 g Alanine in 4.95 g water and keeping it stirred until it was a clear solution.

Preparation of AgI Particles—Doped with 2.5% CuBr

CuBr-solution: 0.0106 g of copper (I) bromide was dissolved in 0.048 g 48% Hydrobromic acid, afterwards diluted with 8 g water and kept stirring until a clear solution was obtained.

0.2079 g silver nitrate was dissolved in 12 g water and then 3.30 g 10% w/w PVP (MW 10,000) aqueous solution added into it. 3.324 g of CuBr-solution prepared above were slowly dropped under stirring.

Finally a solution of 0.1628 g sodium iodide in 5 g water was slowly dropped and kept stirring overnight to allow the formation of particles. The concentration of silver based on the calculation of metallic silver was 0.55% w/w in which Ag/Cu ratio is 40/1 in mol/mol (2.5%).

b) Preparation of Functionalized Particle Samples:

Samples were prepared by mixing of components as prepared above in a sure seal bottle under stirring in the order described in Tables 10 and 11 as shown below ("NP" denotes nanoparticles). Table 10 shows the formulations surface modified by alanine (ALA) and Table 11 shows formulations modified with PVP.

TABLE 10

| Components | Sample designations in FIG. 1 (w/alanine) | | | | |
| --- | --- | --- | --- | --- | --- |
|  | AgBr | AgBr—2.5% CuBr | AgI—2.5% CuBr | AgBr—2.5% CuI | AgBr—2.5% CuI2 |
| AgBr—NP, g | 3.16 | — | — | 3.5 | 3.5 |
| AgBr—2.5% CuBr—NP, g | — | 3.5 | — | — | — |
| AgI—2.5% CuBr—NP, g | — | — | 3.5 | — | — |
| CuI—NP with excess $Cu^{2+}$, g | — | — | — | 0.063 | — |
| CuI—NP, g | — | — | — | — | 0.063 |
| 1% Alanine-sol, g | 0.057 | 0.057 | 0.057 | 0.063 | 0.063 |
| Water, g | 0.633 | 0.293 | 0.293 | 0.644 | 0.644 |

TABLE 11

| Components | Sample designations in FIG. 1 (PVP) | | | | |
| --- | --- | --- | --- | --- | --- |
|  | AgBr-PVP | AgBr—2.5% CuBr-PVP | AgI—2.5% CuBr-PVP | AgBr—2.5% CuI-PVP | AgBr—2.5% CuI2-PVP |
| AgBr—NP, g | 3.5 | — | — | 3.5 | 3.5 |
| AgBr—2.5% CuBr—NP, g | — | 3.5 | — | — | — |
| AgI—2.5% CuBr—NP, g | — | — | 3.5 | — | — |
| CuI—NP with excess $Cu^{2+}$, g | — | — | — | 0.063 | — |
| CuI—NP, g | — | — | — | — | 0.063 |
| Water, g | 0.77 | 0.35 | 0.35 | 0.707 | 0.707 |

Preparation of CuI particles with excess $Cu^{2+}$ (see Example 18)

Preparation of CuI-particles (see Example 17)

Preparation of AgBr particles (see Example 5)

Preparation of AgBr particles-doped with 2.5% CuBr

CuBr-solution: 0.0106 g of copper (I) bromide was dissolved in 0.500 g 48% Hydrobromic acid, afterwards diluted with 16 g water and kept stirring until a clear solution was obtained.

0.2079 g silver nitrate was dissolved in 13.682 g water and then 3.30 g 10% w/w PVP (MW 10,000) aqueous solution added into it. Finally 6.810 g of CuBr-solution prepared above was slowly dropped under stirring. The concentration of silver based on the calculation of metallic silver is 0.55% w/w in which Ag/Cu ratio is 40/1 in mol/mol (2.5%). This procedure results in largely AgBr particles which also comprise copper bromide (doping of AgBr particles by CuBr, or particles of mixed halides).

The germination responses of spores to various particles functionalized with L-alanine (ALA) or PVP were measured after a 24 hour static incubation period. The results are shown in FIG. 1, where the particles identified with an "-Ala" suffix were functionalized with L-alanine.

As seen in FIG. 1, the control *B. cereus* spore samples exhibited appreciable increases in optical density (appreciable growth) when exposed to nutrient conditions, while *B. cereus* spores treated with the indicated functionalized metal halide particles exhibited essentially no change in optical density (no growth) when exposed to the same nutrient conditions. Besides the specific functionalized particles used in these tests, one may also use other functionalized particles of this invention, including functionalized nanoparticles, to deactivate spores. While L-alanine was used as a functionalizing agent in some of the tests, other amino acids and combinations of amino acids may also be used.

Example 45

Effect of CuI Particles on Inhibiting the Growth of Spores

FIG. 2 is a bar chart that shows the effect of CuI/PVP inhibition on *B. cereus* spores growth. CuI/PVP suspensions were made as in Example 28, and the copper concentration was 59 ppm in the final medium comprising CuI/PVP and the bacterial broth. This figure clearly shows the effectiveness of CuI/PVP in preventing *B. cereus* spores growth, and in fact even achieving a slight reduction as compared to the starting spore concentration.

Examples 46-52

Additional Antimicrobial Results Using Particulate Suspensions

Antimicrobial testing was carried out on the following microbes:

Ex. 46—*Pseudomonas aeruginosa* (ATCC 27313) (Table 13)
Ex. 47—*Staphylococcus aureus* (ATCC 25923) (Tables 14)
Ex. 48—*Streptococcus mutans* (ATCC 25175) (Table 15)
Ex. 49—*S. enterica Typhimurium* (ATCC 23564) (Table 16)
Ex. 50—*Mycobacterium fortuitum* (ATCC 6841) (Table 17)
Ex. 51—*Penicillium* (Table 18)
Ex. 52—*Aspergillus niger* (Table 19)

Table 12 is a list of samples, particle sizes and functionalization used in subsequent tables 13-19 with antimicrobial results. The particle size in this table was measured using dynamic light scattering (here and above, unless mentioned otherwise). In some cases the particle size was confirmed by optical absorption or by scanning electron microscopy (SEM). For measurement by dynamic light scattering, the nanoparticle suspensions were diluted in DI water by taking one to two drops of the suspension and adding several ml of water to ensure that a clear (to the eye) solution was obtained in a 1 cm path length cuvette. If the particles were large, the solutions were stirred just before measurement. Several measurements were made to ensure repeatability and reproducibility of samples. Most measurements were carried out using a Malvern Zetasizer Nano ZS light scattering analyzer (available from Malvern Inc, Westborough, Mass.) at ambient temperature, with a backscatter mode at a 173° scattering angle. Commercial polystyrene spheres with known size (60 nm) were used for instrument calibration. Some of the measurements were also made on the Nanotrac particle analyzer (available from Microtrac Inc, Montgomeryville, Pa.), also in the backscattering mode using a fiberoptic probe. The data was converted and reported in the volume fraction mode.

TABLE 12

| Sample number | Preparation method (Example#) | Metal or halide (CuI purity, %) | Surface Modification | Particle size*, nm |
|---|---|---|---|---|
| S1 | 25 | AgBr/CuI (98) | PVP-Aldrich | 182 |
| S2 | 26 | Ag | PVP-Aldrich | 7 |
| S3 | 27 | AgBr | PVP-Aldrich | 4 |
| S4 | 28 | CuI (98) | PVP-Aldrich | 4 |
| S5 | 29 | Ag/AgBr | PVP-Aldrich | Ag = 4, AgBr = 4 |
| S6 | 30 | Ag/CuI (98) | PVP-Aldrich | Ag = 7, CuI = 4 |
| S7 | 31 | AgBr/CuI (98) | PVP-Aldrich | CuI = 4, AgBr = 4 |
| S8 | 26 | Ag | PVP-Aldrich | 6 |
| S9 | 28 | CuI (98) | PVP-Aldrich | 4E |
| S10 | 27 | AgBr | PVP-Aldrich | 4E |
| S11 | 26 | Ag | PVP-Aldrich | 7E |
| S12 | 28 | CuI (98) | PVP-Aldrich | >15E |
| S13 | 37 | $Ag_{0.5}Cu_{0.5}I$ | PVP-Aldrich | 29 |
| S14 | 28 | CuI (98) | PVP-Aldrich | >30E |
| S15 | 6 | AgBr | Thiomalic acid/ Aspartic acid | 25E |
| S16 | | | | |
| S17 | 28 | CuI (98) | PVP-Aldrich | 4E |
| S18 | 27 | AgBr | PVP-Aldrich | 4E |
| S19 | 27 | AgBr | PVP-Aldrich | 4E |
| S20 | 9 | AgBr | Thioglycine/ Aspartic acid | 25E |
| S21 | 9 | AgBr | Thioglycine/ Aspartic acid | 25E |
| S22 | 2a | Ag | Thioglycine/ Aspartic acid | <20E |
| S23 | 2a | Ag | Thioglycine/ Aspartic acid | <20E |
| S24 | 2b | Ag | Thioglycine/ Aspartic acid | <20E |
| S25 | 2b | Ag | Thioglycine/ Aspartic acid | <20E |
| S26 | 28 | CuI (98) | PVP-Aldrich | 4E |
| S27 | 33 | CuI (99.999) | PVP-BASF + $HNO_3$ + $CH_3COOH$ | 4E |
| S28 | 34 | CuI (99.999) | VP-VA Copolymer-BASF + $HNO_3$ | 4E |
| S29 | 35 | | PVP-BASF + $HNO_3$ + $Na_2SO_3$ | 4E |
| S30 | 34 | | VP-VA Copolymer-BASF + $HNO_3$ + $Na_2SO_3$ | 4E |
| S31 | 36 | CuI (99.999) | PVP-BASF + $HNO_3$ | 4 |
| S32 | 36 | CuI (99.999) | PVP-BASF + $HNO_3$ | 263 and 471 |
| S33 | 28 | CuI (98) | PVP-BASF | 5 |
| S34 | 24 | CuI (99.999) | PEG (10k, Aldrich) + $HNO_3$ | 4E |
| S34 | 32 | CuCl | PVP-BASF | 4 to 10E |
| S35 | 26 | Ag | PVP-Aldrich | 6 |
| S36 | 27 | AgBr | PVP-Aldrich | 4E |
| S37 | Purchased | AgI | PVP (AgI nano from ChemPilots) | 25 |
| S38 | 36a | CuI (99.999) | PVP-BASF + $HNO_3$ | 4 |
| S39 | 32 | CuCl | PVP-BASF | <10E |
| S40 | | No AM material | Porous silica | Silica 0.5 to 3 μm |
| S41 | 40(1) | CuI (98.5) | Porous silica | Silica 0 to 20 μm |
| S42 | (40(2)) | CuI (98.5) | Porous silica, | Silica 0.5 to 3 μm |
| S43 | 28 | CuI (98) | PVP-Aldrich | 6 |
| S44 | 36b | CuI (99.999) | PVP-BASF + $HNO_3$ | 1070 |
| S45 | 36b | No AM material | PVP-BASF + $HNO_3$ | |
| S46 | 36b | CuI (99.999) | PVP-BASF + $HNO_3$ | 323 |
| S47 | 36b | No AM material | PVP-BASF + $HNO_3$ | |
| S48 | 36b | CuI (99.999) | PVP-BASF + $HNO_3$ | 315 |
| S49 | 36b | No AM material | PVP-BASF + $HNO_3$ | |
| S50 | 36b | CuI (99.999) | PVP-BASF + $HNO_3$ | 5 |
| S51 | 42b | CuI (99.5%) | PVP-Aldrich (Ground) | 120 |
| S52 | 42b | CuI (99.5%) | PVP-Aldrich (Ground) | 220 |

TABLE 12-continued

| Sample number | Preparation method (Example#) | Metal or halide (CuI purity, %) | Surface Modification | Particle size*, nm |
|---|---|---|---|---|
| S53 | 42b | CuI (99.5%) | PVP-Aldrich (Ground) | 920 (bimodal 170 and 1,500 nm) |

*"E" stands for those particles whose size was estimated. Estimated particle size is based on comparison to previously measured particle sizes for particles made according to the same process.

Example 46

Efficacy Against *P. aeruginosa* of Various Functionalized Nanoparticles

Table 13 shows the reduction of *P. aeruginosa* by exposure to various type of metal halide particles and their combinations, and also in different concentrations, sizes and surface modifications. All of these were tested with controls (meaning without metal halide particles or other known antimicrobial materials). The results from control are not shown, as they all uniformly showed either no growth or moderate growth of microbes under the same conditions. Experiments were conducted in duplicate. Further, in many cases, e.g., in Table 13, result R1 (at 24 hr), the results show >4.57 log reduction. In the same table at 24 hrs the result R2 also show >5.34 log reduction. This does not imply that the result in the second case is more effective than in the first, all it says is that given a starting concentration of microbes, at that point there were too few too count. Thus use of the symbol ">" in all of these tables means that the maximum log reduction for that experiment was reached. That is to say, after the indicated time, there were no viable microbes seen. Sample number (starting with "S" in column 2) when stated will correspond to the sample number in Table 12. If exactly the same result number (Column 1, starting with "R") is used in various tables (Tables 13 to 19), then that corresponds to the same formulation and batch being tested for different microbes. For example R2 result in Table 13 was obtained on *P. aeruginosa*, and the same suspension was used to obtain the R2 result against *S. aureus* in Table 14.

TABLE 13

*P. aeruginosa*

| Result | Sample # | Particles | Conc, PPM, Ag, Cu | 15 min | 30 min | 1 hr | 2 hr | 6 hr | 24 hr |
|---|---|---|---|---|---|---|---|---|---|
| R1 | S1 | AgBr/CuI | 10, 100 | | | 0.4 | 0.93* | 1.53* | >4.57 |
| R2 | S8 | Ag | 10, 0 | | | | 0.94 | 1.11 | >5.34 |
| R3 | S3 | AgBr | 10, 0 | | | | 0.95 | 1.07 | >5.34 |
| R4 | S9 | CuI | 0, 59 | | | >5.34 | >5.34 | >5.34 | >5.34 |
| R5 | S8 + S9 | Ag + AgBr | 10 + 10, 0 | | | | 0.92 | 1.08 | >5.34 |
| R6 | S3 + S9 | AgBr + CuI | 10, 59 | | | >5.34 | >5.34 | >5.34 | >5.34 |
| R7 | S12 | CuI | 0, 59 | 4.32 | >4.47 | >4.47 | >4.47 | | |
| R8 | S11 + S12 | Ag + CuI | 10, 59 | >4.47 | >4.17 | >4.47 | >4.47 | | |
| R9 | S10 + S12 | AgBr + CuI | 10, 59 | 4.17 | >4.47 | >4.47 | >4.47 | | |
| R10 | S11 + S12 | Ag + CuI | 10, 6 | 0.09 | 0.07 | 0.08 | 0.20 | | |
| R11 | S12 | CuI | 0, 12 | 0.31 | 0.33 | 0.33 | 0.42 | 1.22 | >4.41 |
| R12 | S11 + S12 | Ag + CuI | 2, 12 | 0.3 | 0.3 | 0.42 | 0.46 | 1.32 | >4.41 |
| R13 | S10 + S12 | AgBr + CuI | 2, 12 | 0.34 | 0.25 | 0.34 | 0.41 | 1.13 | >4.41 |
| R14 | S11 + S12 | Ag + CuI | 10, 59 | 2.35 | >4.41 | >4.41 | >4.41 | >4.41 | >4.41 |
| R15 | S15 | AgBr | 10, 0 | | | | 0.05 | 0.91 | >4.40 |
| R16 | S15 + S17 | AgBr + CuI | 10, 59 | 2.22 | 3.36 | 3.75 | >4.25 | >4.40 | |
| R17 | S20 | AgBr | 10, 0 | 0.19 | 0.18 | 0.16 | 0.27 | 3.04 | |
| R18 | S21 | AgBr | 10, 0 | 0.22 | 0.15 | 0.18 | 0.18 | 2.90 | |
| R19 | S20 + S17 | AgBr + CuI | 10, 59 | 1.55 | 2.37 | 3 | 3.69 | >4.73 | |
| R20 | S21 + S17 | AgBr + CuI | 10, 59 | 1.67 | 2.54 | 3.06 | 3.82 | >4.73 | |
| R21 | S24 | Ag | 10, 0 | 0.24 | 0.3 | 0.33 | 0.32 | 0.28 | |
| R22 | S24 + S17 | Ag + CuI | 10, 59 | 3.68 | 4.31 | >4.53 | >4.77 | >4.77 | |
| R23 | S17 | CuI | 0, 59 | 2.30 | 2.97 | 3.81 | 4.76 | >4.77 | |
| R24 | S22 | Ag | 10, 0 | 0.18 | 0.14 | 0.17 | 0.19 | 0.19 | |
| R25 | S22 + S26 | Ag + CuI | 10, 59 | >4.50 | >4.65 | >4.65 | >4.65 | >4.65 | |
| R26 | S26 | CuI | 0, 59 | >4.65 | >4.65 | >4.65 | >4.65 | >4.65 | |
| R27 | S27 | CuI | 0, 59 | >6.76 | >6.76 | >6.76 | >6.76 | >6.76 | |
| R28 | S28 | CuI | 0, 59 | >6.76 | >6.76 | >6.76 | >6.76 | >6.76 | |
| R29 | S31 | CuI | 0, 59 | >4.78 | >4.78 | >4.78 | >4.78 | >4.78 | |
| R30 | S32 | CuI | 0, 59 | 4.11 | >4.78 | 4.36 | 4.54 | >4.78 | |
| R31 | S33 | CuI | 0, 59 | >4.19 | >4.48 | 4.63 | >4.78 | >4.63 | |
| R32 | S35 | Ag | 60, 0 | 0.05 | | −0.05 | −0.02 | 0.06 | 1.57 |
| R33 | S36 | AgBr | 60, 0 | 0.01 | | −0.11 | −0.01 | 0.15 | 3.67 |
| R34 | S37 | AgI | 60, 0 | 0.01 | | 0.01 | 0.06 | 0.19 | 0.29 |
| R35 | S38 | CuI | 0, 60 | >4.56 | | >4.56 | >4.56 | >4.56 | >4.56 |
| R36 | S39 | CuCl | 0, 60 | 0.05 | | 0.03 | 0.19 | 0.47 | 1.21 |
| R37 | S40 | No AM material | 0, 0 | 0.24 | | 0.2 | | 0.04 | 0.02 |
| R38 | S41 | CuI | 0, 19 | 0.97 | | 2.32 | | >4.59 | 3.58 |
| R39 | S42 | CuI | 0, 15 | 1.50 | | 3.89 | | >5.16 | 4.57 |
| R40 | S43 | CuI | 0, 59 | >5.04 | | >5.19 | | >5.19 | >5.19 |
| R41 | S44 | CuI | 0, 59 | >4.73 | | >5.19 | | >5.19 | >5.19 |
| R42 | S45 | No AM material | 0, 0 | 0.26 | | 0.30 | | 0.69 | 0.01 |
| R43 | S46 | CuI | 0, 59 | 5.04 | | >5.19 | | >5.19 | >5.19 |

TABLE 13-continued

P. aeruginosa

| | | | Conc, PPM, | Time | | | | | |
|---|---|---|---|---|---|---|---|---|---|
| Result | Sample # | Particles | Ag, Cu | 15 min | 30 min | 1 hr | 2 hr | 6 hr | 24 hr |
| R44 | S47 | No AM material | 0, 0 | 0.34 | | 0.45 | | 0.66 | 0.07 |
| R45 | S48 | CuI | 0, 59 | >5.19 | | >5.19 | | >5.19 | >5.19 |
| R46 | S49 | No AM material | 0, 0 | 0.28 | | 0.37 | | 0.77 | 0.95 |
| R47 | S50 | CuI | 0, 59 | >5.19 | | >5.19 | | >5.19 | >5.19 |
| R48 | S51 | CuI | 0, 59 | >4.53 | | >4.53 | | >4.53 | >4.53 |
| R49 | S52 | CuI | 0, 59 | 4.38 | | >4.53 | | >4.53 | >4.53 |
| R50 | S53 | CuI | 0, 59 | 3.91 | | 3.84 | | >4.53 | >4.53 |

Results on *P. aeruginosa*, a gram negative bacterium, are shown in Table 13. Comparison of R1 and R6 (for CuI and AgBr mixture) in Table 13 shows that when the particle size of CuI is decreased from about 182 to 4 nm along with the changes in the preparation method, the efficacy at 24 hr remains about the same, achieving the maximum log reduction. However, use of the smaller particle size impacts the efficacy at shorter times, producing higher log reductions at shorter times. Result R9 in this table shows that efficacy at much shorter times, i.e., at 15 minutes is surprisingly high. This high efficacy is seen even in those formulations where only CuI is used, such as in R7. All of the above formulations use suspensions with a copper concentration of 59 ppm. Interestingly as seen in R5, when Ag and AgBr with PVP surface modification are combined (both at 10 ppm silver concentration, with a total silver concentration of 20 ppm), their combined efficacy is not much superior to any one of these alone in 10 ppm concentration (R2 and R3), whereas copper iodide efficacy at 59 ppm is much higher than any of these (R4).

When the copper concentration is dropped to 12 ppm, such as in R11, the efficacy at short times suffers, but one is still able to achieve the same efficacy at 24 hrs comparable to R1 which uses larger CuI particles and at higher copper concentration. Addition of silver as silver metal or silver bromide to copper iodide (compare R11 to R12 or R13; or compare R7 to R8 or R9), does not improve the efficacy, showing that CuI by itself is quite effective.

Further, for *P. aeruginosa*, different surface modifications were used on CuI, such as PVP from Aldrich, PVP from BASF, VP-VA copolymer from BASF, Polyethylene glycol, and even acids for surface peptization (see results R26 to R31), and all of these show that each of these suspensions were maximally effective. Comparison of results R15 on AgBr with R17 and R18 show that in this case surface functionalization type made a difference with thioglycine/aspartic acid being more effective than PVP. Further, comparing AgBr with Ag metal (R17 or R18 when compared with R21) shows that when silver is incorporated as silver bromide (for thioglycine/aspartic acid modification), the formulation is more effective in reducing the microbe concentration. One may also mix different metal halides or metal halide and a metal, and also particles with different surface modifications with high efficacy against *P. aeruginosa* as shown in numerous results in this table.

Results R32 to R36 compare nanoparticles of various silver salts (AgBr and AgI), silver metal and various copper salts (CuCl and CuI), all of these surface modified with PVP and by themselves only, and all of them at metal concentration of 60 ppm. This data clearly shows CuI has the highest efficacy and the other materials show lower efficacy against this microbe.

Results R37 through R39 were on porous silica particles. R37 was for silica particles with a size in the range of 0.5 to 3 µm which do not have any CuI. Result R38 was for silica particles with a size in the range of 0 to 20 µm which had CuI infused by the method of Example 40 (method 1). The copper metal content in these particles was 1.9% by weight. Result R39 was for silica particles with a size in the range of 0.5 to 3 µm which had CuI infused by the method in Example 41 (method 2). The copper metal content in these particles was 1.5% by weight. These were tested for antimicrobial effect in a suspension, where the silica particles were added with and without CuI. The copper concentration in samples R38 and R39 was 19 and 15 ppm respectively. As expected the sample without antimicrobial additive (result R37) did not show antimicrobial properties. The other two showed a high efficacy.

Results R40 to R47 were for samples S43 to S50 respectively. This series of experiments was done to evaluate the effect on the type of PVP and the effect of the addition of an acid on the particle size of functionalized CuI. Sample S43 was made by the procedure of Example 28 and uses Aldrich PVP and the other samples were made by the procedure of Example 36b and use BASF PVP. PVP from different sources differ in acidity depending on the process used, and may require different levels of pH adjustment. Results R42, R44 and R46 were on samples where acid was added but no CuI. During testing in the buffer solution with microbes, the pH of all solutions was above 6. All samples with CuI showed high antimicrobial activity, and all samples without CuI did not show any appreciable activity. It was surprising that all functionalized particles made by these methods showed high antimicrobial activity although their average sizes varied from about 1.000 nm to 6 nm.

Results R48 to R50 (on samples S51 to S53 respectively) are the results of suspension testing of particles made by wet grinding in the presence of PVP comprising an aqueous solution using the process described in Example 42b. These three samples were obtained from the same run but extracted at different periods of grinding. The average particle size of these three samples was 120, 220 and 920 nm respectively. The last sample, S53 with an average particle size of 920 nm, had a bimodal distribution with particles average sizes peaking at 170 and 1,500 nm. All of these show high antimicrobial efficacy, with the smallest particle size sample (Result R48 on Sample S51) showing a great efficacy at shorter time periods.

Example 47

Efficacy Against *S. aureus* of Various Functionalized Nanoparticles

TABLE 14

*S. aureus*

| Result# | Sample # | Particles | Conc, PPM, Ag, Cu | 15 min | 30 min | 1 hr | 2 hr | 6 hr | 24 hr |
|---|---|---|---|---|---|---|---|---|---|
| R2 | S8 | Ag | 10, 0 | | | | 0.08 | 0.22 | 4.29 |
| R3 | S3 | AgBr | 10, 0 | | | | 0.46 | 0.39 | >4.44 |
| R4 | S9 | CuI | 0, 59 | | | | >4.44 | >4.44 | >4.44 |
| R5 | S8 + S9 | Ag + AgBr | 10 + 10, 0 | | | | 0.02 | 0.22 | >4.44 |
| R6 | S3 + S9 | AgBr + CuI | 10, 59 | | | | >4.44 | 4.29 | >4.44 |
| R7 | S12 | CuI | 0, 59 | >4.07 | >4.31 | >4.31 | >4.31 | | |
| R8 | S11 + S12 | Ag + CuI | 10, 59 | >4.31 | >4.31 | >4.31 | >4.31 | | |
| R9 | S10 + S12 | AgBr + CuI | 10, 59 | >4.31 | >4.31 | 4.07 | >4.31 | | |
| R10 | S11 + S12 | Ag + CuI | 10, 6 | 0.05 | 0.04 | 0.06 | 0.09 | | |
| R11 | 12 | CuI | 0, 12 | 0.79 | 0.95 | 1.35 | 1.81 | 2.96 | >4.34 |
| R12 | S11 + S12 | Ag + CuI | 2, 12 | 0.69 | 0.88 | 1.20 | 1.66 | 3.16 | >4.34 |
| R13 | S10 + S12 | AgBr + CuI | 2, 12 | 0.79 | 1.04 | 1.30 | 1.71 | 3.03 | >4.34 |
| R14 | S11 + S12 | Ag + CuI | 10, 59 | 0.58 | 2.71 | >4.34 | >4.34 | >4.34 | >4.34 |
| R27 | S27 | CuI | 0, 59 | >6.47 | >5.99 | >6.47 | >6.47 | >6.47 | >6.47 |
| R28 | S28 | CuI | 0, 59 | >6.47 | >6.47 | >6.05 | >6.47 | >6.47 | >6.47 |

Table 14 shows results from similar experimentation on *S. aureus*, a gram positive bacterium responsible for common staph infections. Comparing R4 to R3 and R2 in this table shows superior effectiveness of copper iodide. Comparing results on Ag metal, AgBr, their combination and CuI, shows similar behavior as for *P. aeruginosa*, namely that CuI was more effective than either silver metal or silver bromide, or mixture of silver+silver bromide with PVP surface modification. Also CuI in small particle size by itself or mixed with silver metal or silver bromide was highly effective as seen in results R7, R8 and R9. Similar conclusion for *S. aureus* as for *P. aeruginosa* can be drawn on concentration of the compounds, mixture of different metal halides or metal halide and a metal, and particles with different surface modifications.

Example 48

Efficacy Against *S. mutans* of Various Functionalized Nanoparticles

TABLE 15

*S. mutans*

| Result# | Sample # | Particles | Conc, PPM, Ag, Cu | 15 min | 30 min | 1 hr | 2 hr | 6 hr | 24 hr |
|---|---|---|---|---|---|---|---|---|---|
| R27 | S27 | CuI | 0, 59 | >4.75 | >4.75 | >4.60 | >4.75 | >4.75 | >4.75 |
| R28 | S28 | CuI | 0, 59 | >4.75 | >4.75 | >4.75 | >4.75 | >4.75 | >4.75 |

To test the broad efficacy of metal halides, and in particular for copper iodide, we also tested functionalized nanoparticles of this material against several other microbes. One of these is a strep bacterium *S. mutans*, commonly found in mouth infections. R27 and R28 in Table 15 shows that CuI particles modified with PVP and the copolymer (VP-VA) both resulted in effective reduction of populations of this bacteria.

Example 49

Efficacy Against *S. enterica Typhimurium* of Various Functionalized Nanoparticles

TABLE 16

| | | | | *S. enterica Typhimurium* | | | | | |
|---|---|---|---|---|---|---|---|---|---|
| | | | Conc, PPM, | Time | | | | | |
| Result# | Sample # | Particles | Ag, Cu | 15 min | 30 min | 1 hr | 2 hr | 6 hr | 24 hr |
| R15 | S15 | AgBr | 10, 0 | 0.26 | 0.47 | 0.57 | 1.52 | >4.85 | |
| R23 | S17 | CuI | 0, 59 | >4.85 | >4.85 | >4.85 | >4.85 | >4.85 | |
| R16 | S15 + S17 | AgBr + CuI | 10, 59 | >4.85 | >4.70 | >4.50 | 4.70 | >4.85 | |

Table 16 shows that at 59 ppm, CuI surface modified with PVP showed a high degree of effectiveness (R23) against the microbe *S. enterica* when used alone or in combination with AgBr modified with thiomalic and aspartic acids (R16). This was more effective as compared to AgBr alone with a silver concentration of 10 ppm in the suspension (R15).

Example 50

Efficacy Against *M. fortuitum* of Various Functionalized Nanoparticles

TABLE 17

| | | | | *M. fortuitum* | | | | | |
|---|---|---|---|---|---|---|---|---|---|
| | | | Conc, PPM, | Time | | | | | |
| Result# | Sample # | Particles | Ag, Cu | 2 hr | 6 hr | 24 hr | 48 hr | 72 hr | 96 hr |
| R2 | S2 | Ag | 10, 0 | | | 2.33 | 3.68 | 4.41 | 5.04 |
| R3 | S3 | AgBr | 10, 0 | | | 1.51 | 1.93 | 1.65 | 2.42 |
| R29 | S4 | CuI | 0, 59 | | | 2.46 | 2.63 | 2.93 | 3 |
| R30 | S2 + S3 | Ag + AgBr | 3.3 + 6.6, 0 | | | 0.59 | 1.28 | 1.41 | 1.95 |
| R31 | S2 + S4 | Ag + CuI | 10, 59 | | | 2.40 | 2.62 | 2.85 | 3.22 |
| R32 | S3 + S4 | AgBr + CuI | 10, 59 | | | 1.91 | 2.71 | 2.91 | 3.02 |
| R15 | S15 | AgBr | 10, 0 | 0.29 | 1.41 | 1.94 | 2.50 | | |
| R23 | S17 | CuI | 0, 59 | 0.79 | 1.69 | 1.35 | 1.41 | | |
| R16 | S15 + S17 | AgBr + CuI | 10, 59 | 1.48 | 1.35 | 1.58 | 1.29 | | |

Table 17 presents data on the antimicrobial effectiveness of these materials against *M. fortuitum*. In general CuI is effective, when used in the same concentration as with the other microbes. One can increase the concentration of CuI to achieve higher level of effectiveness against this microbe. Strongest reduction was seen by silver metal modified with PVP (R2). This was much stronger than silver bromide (R3) or copper iodide (R29). When Ag or AgBr was combined with CuI (R31 and R32 respectively), the formulation was effective. This type of reduced activity of combinations was not seen for other microbes.

Example 51

Efficacy Against *Penicillium* of Various Functionalized Nanoparticles

TABLE 18

| | | | | *Penicillium* | | | | | |
|---|---|---|---|---|---|---|---|---|---|
| | | | Conc, PPM, | | | Time | | | |
| Experiment # | Sample # | Particles | Ag, Cu | 2 hr | 6 hr | 24 hr | 48 hr | 72 hr | 96 hr |
| R27 | S27 | CuI | 0, 59 | | | >3.98 | >3.98 | >3.98 | >3.98 |
| R28 | S28 | CuI | 0, 59 | | | >3.98 | >3.98 | >3.98 | >3.98 |

To examine the effectiveness of the inorganic metal salts against molds, experiments were done against *Penicillium* as shown in Table 18. R27 and R28 in this table shows that CuI particles modified with PVP and the copolymer (VP-VA) both resulted in effective reduction of this mold.

Example 52

Efficacy Against *A. niger* of Various Functionalized Nanoparticles

TABLE 19

| | | | | *A. niger* | | | | | |
|---|---|---|---|---|---|---|---|---|---|
| | | | Conc, PPM, | | | Time | | | |
| Result# | Sample # | Particles | Ag, Cu | 2 hr | 6 hr | 24 hr | 48 hr | 72 hr | 96 hr |
| R33 | S11 | Ag | 50, 0 | | −0.09 | −0.01 | 0.01 | 0.00 | −0.16 |
| R34 | S10 | AgBr | 50, 0 | | 0.06 | −0.14 | 0.16 | 0.21 | 0.15 |
| R35 | S14 | CuI | 0, 295 | | 0.06 | 0.82 | 0.77 | 1.43 | 1.99 |
| R36 | S10 + S14 | AgBr + CuI | 50, 295 | | −0.02 | 0.39 | 0.78 | 0.62 | 0.81 |

Table 19 shows the results for another mold *A. niger*. The strongest response is shown by CuI (R35) by itself.

Example 53

Antimicrobial Testing of Mixed Metal Halide Suspensions (Suspensions Prepared by Methods of Examples 37, 38 and 39)

Antimicrobial testing of Ag—Cu mixed metal halides and their performance comparison with CuI was done using optical density method. FIG. 5 is a plot bar chart of Optical Density (OD, Y-axis) as a measure of growth against the effect of copper iodide particles and Ag—CuI mixed metal halides, and a control. Optical density was measured after treating the bacterial solutions with the nanoparticles of mixed metal halides (or solid solutions of mixed metal halides). Lower optical density implies growth inhibition and showed higher effectiveness. $Ag_{25}Cu_{75}I$, $Ag_5Cu_5I$, and $Ag_{75}Cu_{25}I$ all showed effective antimicrobial properties against *P. aureginosa* (FIG. 5) and *S. aureus* (FIG. 6), however, none were as effective as CuI nanoparticles alone (CuI was made as in Example 23). Further, with increasing copper content in the solid solution the efficacy of the material increased.

Example 54

Coating of Textiles with Metal Halides and their Antimicrobial Testing

The following methods were used to prepare coating suspensions of functionalized particles and to use these suspensions in coating textile fabrics.

a) Preparation of Particles $GLYMO_H$—Sol: 0.144 g Formic acid and 1.71 g water respectively were added into 7.5 g Glycidoxypropyltrimethoxysilane (GLYMO) under stirring and kept stirring overnight Preparation of AgBr particles (see Example 5)

Preparation of CuI particles (see Example 17)

Preparation of Ag° Particles (see Example 3, water used was 5.202 g rather than 9.825 g resulting in silver concentration of 0.61% w/w.)

b) Preparation of Coated Textile Samples i) Preparation of Coating Suspensions:

Amine cured PEG coating suspension was made using 0.80 g Polyethylene glycol (PEG, MW=1,000) dissolved in 18.056 g water. 5.36 g of $GLYMO_H$-Sol, 6.192 g of AgBr particles, 4.624 g of CuI particles and 4.968 g of 2% w/w Jeffamine HK-511 in water respectively were slowly dropped into the PEG solution under stirring. This sol was immediately used to make coatings.

ii) Application of Coating Suspension to Textile Sample

A sample of cotton textile (25×25 cm, untreated cotton Muslin) was washed in hot water and was placed in a beaker with the amine cured PEG coating suspension from Part b) i) above. The textile sample was completely wet by squeezing the coating suspension out of it by hand many times and then soaking it again. Finally the wet substrate was wrung using a mechanical roller type equipment Dyna-Jet Model BL-38 and cured in oven at 120 C for 1 hour. The cured coating had theoretically 1.5% w/w antibacterial material of Ag/Cu=1/1 in mol/mol.

Separately, samples of cotton textile (25×25 cm, untreated cotton canvas) were washed in hot water and placed in a beaker with the coating suspension (polyurethane coating suspension or amine cured PEG suspension). The textile sample was completely wet by squeezing the coating sol out of it by hand many times and then soaking it again. Finally the wet substrate was wrung using Dyna-Jet Model BL-38 and cured in an oven at 120 C for 1 hour.

The antimicrobial effectiveness of fabrics coated with functionalized particles was evaluated using ASTM E 2149-01, incorporated by reference herein in its entirety. Briefly, overnight cultures were adjusted to a final concentration of $1.5 \times 10^6$ in 250 ml Erlenmeyer flasks containing sterile PBS. Fabric samples (5.4 cm×5.4 cm) were introduced to the flask and agitated at 25° C. At appropriate time exposure intervals, 1-ml aliquots were removed and the viable bacteria were enumerated as described previously.

FIG. 3 shows the efficacy of treated fabrics containing functionalized particles of the present invention against *P. aeruginosa*. Samples were tested both initially and after washing 3 times and 10 times in ordinary household detergent. "Sample 0×" indicates it was never washed; "Sample 3×" was washed three times; and Sample "10×" ten times. An uncoated fabric sample was used as a control.

Reductions in bacterial populations exceeding 4-$\log_{10}$ can readily be obtained using antimicrobial coatings containing the present functionalized particles (FIG. 3). In addition, washing with household detergent introduces a delay in the antimicrobial effect, but does not decrease the antimicrobial effectiveness of the coatings.

Example 55

Preparation of Coatings with Metal Halides and their Antimicrobial Testing a) Preparation of Coating Sols in Organic Epoxy Matrix The procedure for the preparation of a coating sol containing organic epoxy was as follows: 0.25 g EPON® 8281 (organic epoxy, Miller Stephenson Chemical Co.) and 0.375 g Anquamine® 721 (curing agent and emulsifier, Air Products and Chemicals Inc.) were transferred in a glass bottle and mixed with a spatula until it became milky, homogenous. 1.40 g AgBr-sol (for AgBr-sol preparation see Example 5), 1.04 g CuI-sol (for CuI-sol preparation see Example 17) and 0.155 g water were added into the mixture of EPON® and Anquamine®, and the sol was kept stirring with a spatula and treated in an ultrasonic bath for about 4 minutes to be obtained a homogenous emulsion. The final coating sol has calculated solid content of 14% w/w. The calculated percentage of bioactive material (in metallic form, Ag/Cu=1/1 in mol/mol) in cured coating is 3% w/w in this example. The amounts of components used to make coatings with different bioactive materials are as in Table 20:

TABLE 20

|  | 3% Ag/Cu = 1/1 | 0.75% Ag/Cu = 1/1 | 3% Ag (Br) | 0.75% Ag (Br) | 3% Ag° | 0.75% Ag° |
| --- | --- | --- | --- | --- | --- | --- |
| EPON® 8281, g | 0.25 | 0.25 | 0.25 | 0.25 | 0.25 | 0.25 |

TABLE 20-continued

|  | 3% Ag/Cu = 1/1 | 0.75% Ag/Cu = 1/1 | 3% Ag (Br) | 0.75% Ag (Br) | 3% Ag° | 0.75% Ag° |
| --- | --- | --- | --- | --- | --- | --- |
| Anquamine® 721, g | 0.375 | 0.375 | 0.375 | 0.375 | 0.375 | 0.375 |
| AgBr-sol, g | 1.40 | 0.341 | 2.218 | 0.542 | — | — |
| CuI-sol, g | 1.04 | 0.255 | — | — | — | — |
| Ag°-sol, g | — | — | — | — | 2.218 | 0.542 |
| Water, g | 0.155 | 1.928 | 0.379 | 1.98 | 0.379 | 1.98 | b) Preparation of Coating Suspensions in Epoxy Silane Matrix

The procedure used to prepare a coating suspension containing epoxy silane was as follows: suspensions having a solid content of 14% w/w for making coatings with an epoxy slime matrix were prepared in the same way as described in section a) above but with amounts of the components shown in Table 21:

TABLE 21

|  | 0.75% Ag° |
| --- | --- |
| PEG, g | 0.1 |
| Water, g | 1.545 |
| GLYMO$_H$, g | 0.67 |
| AgBr—NP, g | — |
| CuI—NP, g | — |
| Ag°—NP, g | 0.61 |
| 2% HK-511, g | 0.621 | c) Application of Coatings to Polystyrene 24-Well Plates

50 µL of one of the coating suspensions prepared in sections a) and b) was transferred using a pipetter into a well of a 24-well plate (Sigma Aldrich, CLS3526-1 EA) and then spread with a spatula over the bottom surface (1.9 cm$^2$) of the well. This step was repeated three times to produce three samples in 3 wells of the 24-well plate. The plate was placed in an oven at 50° C. for 10-15 minutes. Subsequently, another coating of a different suspension was applied to prepare a second coating sample, again prepared in triplicate, following the same procedure. After applying 8 different coatings of different compositions each in triplicate, the 24-well plate was placed in an oven at 80° C. for 2 hours for final curing.

Figure 4:
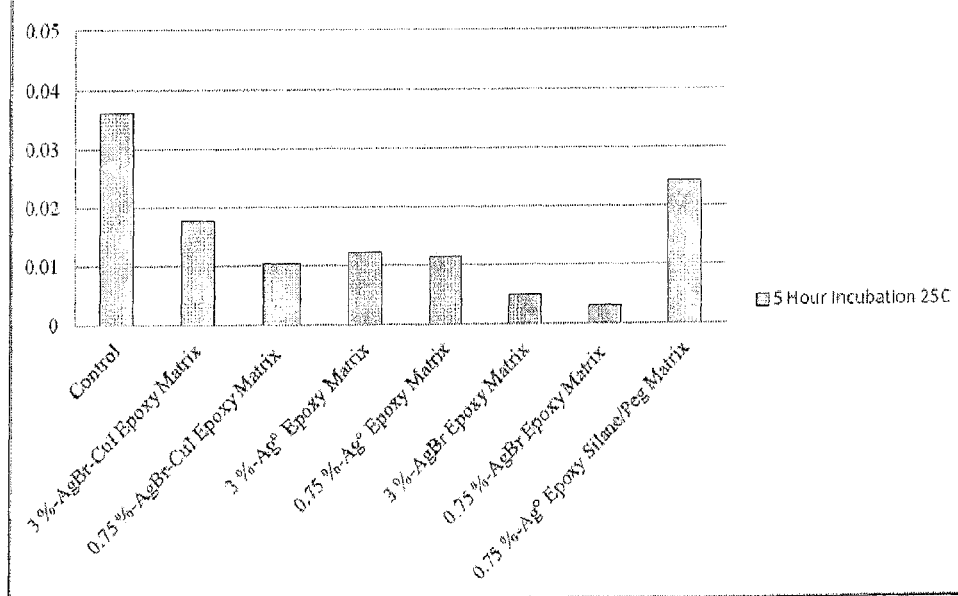

Provision of antimicrobial coatings on ceramic substrates other than glass (e.g., coatings on crystalline ceramics) can be obtained using methods similar to these to provide antimicrobial coatings on glass. In some cases, the initial treatment with 10% sodium hydroxide solution can be replaced by other chemical treatments known by those skilled in the art to be effective for the specific ceramic substrates.

d) Testing of Antimicrobial coatings 24-well polystyrene plates (Corning) containing 500 µl trypticase soy broth were inoculated with an overnight culture of *P. aeruginosa* to an optical density (OD600; Eppendorf Bio Photometer) of 0.05. Plates were incubated at 25° C. for 24 h. Following incubation, 100 µl of supernatant was removed from the wells and the OD600 was determined. The antimicrobial effectiveness of solid bodies coated with functionalized nanoparticles was demonstrated (FIG. 4). It is seen from FIG. 4 that coatings containing functionalized nanoparticles have a pronounced effect in decreasing bacterial populations. It is also seen that the matrix material (control sample) of the coating has a small but measureable effect on the antimicrobial behavior, as shown in the decreased OD associated with the lane marked "control".

Example 56

Preparation of Coatings with CuI and their Antimicrobial Testing

Materials and Methods

For this example two sources for CuI were used. The first was bulk copper iodide powder (99.5% Sigma Aldrich) and the second nano-particles of CuI functionalized with PVP prepared from the acetonitrile process and isolated as a dry powder. For the nano-particles two high loadings of CuI in PVP were prepared namely 60 and 50 wt % CuI in PVP. The CuI used was 99.5% from Sigma Aldrich and the PVP was 10,000 MW from Sigma Aldrich. A typical high loading preparation was as follows.

To a liter pear shaped flask fitted with a stir bar was added 4.05 g of CuI powder and 300 ml of anhydrous acetonitrile. This was stirred to give a pale yellow solution. In a separate flask fitted with a stir were added 4.05 g of PVP and 200 ml of anhydrous acetonitrile. This was stirred for 2 hours to give a straw yellow colored solution. While stirring the CuI solution the PVP solution was slowly added to it to give a transparent yellow solution. Upon stirring at room temperature this solution slowly turned a light green color; this took about one hour for completion. This solution was dried under reduced pressure at 30° C. to form a light green powder with a CuI content of 50 wt %. This procedure was repeated except the initial CuI concentration was increased to 6.07 g to give a concentration of CuI in the powder of 60 wt %.

Preparation of Urethane Coating Containing CuI

To a beaker was added 5 g of an aliphatic urethane 71/N aqueous dispersions (35% solids, maximum viscosity 200 cP) sold under the tradename of ESACOTE obtained from Lamberti SpA, (Gallarate, Italy). To this was added 0.118 g of CuI powder (99.5% from Sigma Aldrich, particles not functionalized). This was stirred vigorously and 0.1 g of the cross linking agent PZ28 (Polyfunctional Aziridine manufactured by PolyAziridine, LLC Medford, N.J.) was added to the coating formulation. The urethane coating was applied to stainless steel substrates 2"×2" by brush application and cured at room temperature for 12 hours followed by two hours at 70° C. The cured coating was transparent with a slight brown tint. It was durable and hard with good chemical resistance to both water and ethanol. The $Cu^+$ content of the dried coating was 2.0 wt %. This procedure was repeated except using the nano-powders of CuI described above to give coated surfaces with different concentrations/types of $Cu^+$. These coated substrates were tested for antimicrobial activity against *P. aeruginosa* using a method as described below. As a comparison point a metal coated with DuPont antimicrobial (commercial powder coating) ALESTA™ was also tested (obtained from Dupont, Inc. (Industrial Coatings Division, Wilmington, Del.)). The antimicrobial materials in these coatings were zeolite particles (about 2 to 3 μm in size) infused with silver and zinc ions.

Test Method for evaluating Coatings (Based on Japanese Industrial Standard JIS Z 2801: 2000, incorporated by reference herein in its entirety.):

Test coupons (50×50 mm) were prepared by spraying with 70% ethanol to reduce bacterial background presence. Sample coupons were allowed to air dry before re-spraying with 70% ethanol and allowed to dry completely before testing. Polyethylene (PE) cover slips (40×40 mm) were sterilized via bactericidal UV for 30 minutes per side.

Testing involved preparation of McFarland number 0.5 standardized solution of *P. aeruginosa* bacteria in PBS from an overnight culture. The standard solution was diluted 1:100 and inoculated onto sample coupons in 400 μL volume dropwise. Sterile PE films were placed over the inoculated area to ensure wetting of the surface beneath the film. Samples were then incubated in a sealed environment (95% relative humidity) from zero to 24 hours at 25° C. before removal. Bacteria were recovered by swabbing both the coupon surface and the PE film with a cotton-tipped swab pre-dipped in 1 ml of Dey-Engley (DIE) neutralizing broth. The swab was then submersed in a tube containing DIE broth and vortexed to resuspend the bacteria. Test samples were serially diluted in sterile PBS and enumerated with the spread plate method (Eaton et al., "Spread Plate Method," in Standard Methods for the Examination of Water & Wastewater, 21$^{st}$ ed., American Public Health Association, Washington, D.C., pp. 9-38-9-40. 9215C, 2005) for 24-48 hours at 37° C. The bacterial reductions were determined by comparison to the recovery of bacteria from control samples consisting of polyurethane-coated coupons without nanoparticles at each exposure interval.

The coating compositions and the results are summarized in Table 22.

TABLE 22

| Wt % $Cu^+$ in Coating | Type of CuI used | Particle size* | $Log_{10}$ Reduction (*P. aeruginosa*) 6 hr | 24 hr |
|---|---|---|---|---|
| 2.0 | Bulk Powder (99.5%) | 1 to 2 μm | 0.31 ± 0.03 | 0.29 ± 0.08 |
| 4.3 | CuI nanoparticles (60 wt % in PVP) | 254 nm | >5.69 ± 0.00 | >5.69 ± 0.00 |
| 3.0 | CuI nanoparticles (50 wt % in PVP) | 241 nm | >5.49 ± 0.17 | >5.69 ± 0.00 |
| 0.0 | None | | −0.02 ± 0.10 | −0.02 ± 0.05 |
| DuPont Crystal Clear AM coating | None | 2 to 3 μm | 0.89 ± 0.08 | 4.52 ± 0.00 |

*Particle size of CuI or the antimicrobial material (optical microscope used to characterize bulk powder).

These results show that functionalized CuI particles delivered significantly better antimicrobial performance as compared to the commercial antimicrobial coating, especially at the 6-hour mark. It is notable that the use of CuI (as received) as non-functionalized particles in the coatings when used at about 2 μm in size did not result in any perceived antimicrobial activity.

Example 57

Preparation of Urethane Coatings Containing Wet Ground CuI Dispersion in Urethane (Emulsion) Resin Aliphatic urethane 71/N aqueous dispersions (35% solids) sold under the Tradename of ESACOTE™ obtained from Lamberti SpA, (Gallarate, Italy). This was divided in two parts. In one part CuI was added and ground to a small particle size for a duration of 240 minutes as described in Example 42a so that the smaller CuI particles being formed were functionalized by the PU dispersion. These two parts were then mixed in different proportions to vary the amount of copper in the coating formulation. As an example a formulation where these were mixed in a proportion of 50% each by weight was made as follows. To a beaker was added 3 g of an aliphatic urethane 71/N aqueous dispersion was added 3 g of the CuI comprising dispersion. This was mixed well to form a homogeneous material. While stirring 0.12 g of the cross linking agent PZ28 (polyfunctional aziridine manufactured by PolyAziridine, LLC Medford, N.J.) was added to this mixture. The urethane formulation was applied to stainless steel substrates 2"×2" by brush application and cured at room temperature for 12 hours followed by two hours at 70° C. The cured formulation was transparent with a slight brown tint. It was durable and hard with good chemical resistance to both water and ethanol. The $Cu^+$ content of the dried coating was 3.51 wt %. This procedure was repeated by varying the ratio of PU71/N to CuI urethane dispersion to give coated surfaces with different concentrations of $Cu^+$ as listed in Table 23. These were tested against *P. aeruginosa* as described in the above example, and the results are shown in Table 23. In this example, it should be emphasized that polyurethane 71/N aqueous dispersion is an emulsion of a hydrophobic urethane, as after it is coated and dried, this cannot be solvated in water.

TABLE 23

| Ratio PU:(CuI + PU) (by weight) | Wt % $Cu^+$ in Dried Coating | $Log_{10}$ Reduction 6 hours | $Log_{10}$ Reduction 24 hours |
|---|---|---|---|
| 10:90 | 6.33 | >6.08 ± 0.05 | >5.98 ± 0.05 |
| 50:50 | 3.51 | 3.24 ± 0.05 | >5.82 ± 0.05 |
| 75:25 | 1.76 | 3.71 ± 0.05 | >5.76 ± 0.05 |
| 90:10 | 0.70 | 3.24 ± 0.05 | >5.98 ± 0.05 |
| 100:0 | 0 | 0.55 ± 0.05 | −0.04 ± 0.08 |

The above results show that incorporation of CuI in the coatings which were prepared by grinding in a polymeric emulsion process resulted in polymer-functionalized CuI particles having high antimicrobial activity. The polymeric emulsion functionalized the CuI surfaces and stabilized the particles as it was pulverized. PU coatings without the copper-based additive did not demonstrate antimicrobial properties, as demonstrated in the 100:0 result of Table 23. Further, the antimicrobial activity increased with the increased CuI content. It is interesting to note that all of these coatings with CuI had better performance at short times as compared to the commercial coating in Table 22.

Example 58

Povidone-Iodine Plus Copper Iodide/Polyvinylpyrrolidone Antimicrobial Solution

A copper iodide polyvinylpyrrolidone (PVP) powder is prepared by dissolving 0.0476 g of CuI (99.999% Sigma Aldrich) in 50 ml of anhydrous acetonitrile. To this solution is added 10 g of PVP (10,000MW Sigma Aldrich) and stirred to form a pale yellow solution. The acetonitrile is removed under reduced pressure at 30° C. to form a pale green powder. This powder contains 0.158 wt % $Cu^+$.

To 10 ml of a 10% solution of Povidone-iodine (CVS brand, obtained from CVS Pharmacy, Tucson, Ariz.) is added 0.38 g of the CuI/PVP powder previously described to give a 60 ppm concentration of $Cu^+$ in the solution. This forms the Povidone-iodine-CuI/PVP antimicrobial solution.

Example 59

Topical Cream Comprising CuI Nanoparticles: Zone of Inhibition

To prepare this cream, functionalized CuI particles with two different sizes were prepared in PVP.

For the first preparation, the particle size was 241 nm and was made by the procedure described in Example 56 which used 10,000 molecular weight PVP from Sigma Aldrich. This is called 50% Powder (as this had 50% by weight of CuI in the dry powder).

For the second preparation, the particle size was predominantly 4 nm and was prepared in the following fashion. To a reaction flask containing 80 ml of anhydrous acetonitrile, (99.8% Sigma Aldrich Cat. #271004), was added 4.75 g of PVP (Luvitec™ K17 from BASF) and stirred to form a light yellow solution. To this solution was added 0.25 g of CuI (99.999% Sigma Aldrich Cat. #205540) and after stirring for 30 minutes this resulted in a clear pale green solution. Then the bulk of the acetonitrile was removed under reduced pressure at 30° C. to form a viscous paste. The temperature was then increased to 60° C. to completely remove the solvent to give a pale yellow solid. Dynamic light scattering on a dilute sample of the dispersion showed a mean particle size of 4 nm for 85% of the particulate volume, and the others were larger. This had 5 weight % of CuI in the dry powder, and was called 5% Powder.

The cream was prepared in a beaker by adding 0.06 g of Carbomer (obtained from Lubrizol Inc, Wickliffe, Ohio) and 2.0 ml of deionized water (18Mohm-cm). This was mixed to give a slightly hazy non colorless liquid. To this mixture was added 0.2 g of PVP (Sigma Aldrich, 10,000 molecular weight) and the mixture stirred vigorously. The addition of PVP caused a slight decrease in the viscosity. To this solution was added while stirring 1.96 g of CuI/PVP 50% Powder followed by 1.45 g of CuI/PVP 5% Powder. The final concentration of $Cu^+$ in the cream was 2.1 wt %. This cream was tested against *P. aeruginosa* and *S. aureus* using the zone of inhibition method as described below.

Petri dishes for the test were prepared by dispensing 25 ml of sterile agar medium into sterile plates. Overnight cultures were diluted to final working optical density 600 nm of 0.100 and uniformly streaked over the agar using sterile swabs. Cylindrical plugs having a diameter of approximately 5.3 mm were removed from the solidified agar plates by means of a sterile cork borer. Approximately 75 μl of cream were added to the wells. Triple antibiotic first aid ointment from Walgreens Pharmacy (Walgreens Brand, obtained from Walgreens Pharmacy, Tucson, Ariz.) was used as a control material. This cream (control) listed Bacitracin zinc 400 units, Neomycin 3.5 mg and Polymyxin B sulfate at 5,000 units as active ingredients in white petrolatum. Plates as described were incubated in a humidified chamber at 37° C. for 24 hours at which time the plates were examined for bactericidal and growth inhibition effects.

Upon examination of the plates a slight bluish-green hue halo was observed around the wells along with a zone of inhibition for CuI comprising creams. A three scale measure was used to determine the zone of inhibition, "0" for no inhibition, which was indicated by complete absence of the zone of inhibition; "1" as limited inhibition, where the zone diameter (including the well) was in the range of 6 to 8 mm; and significant inhibition designated as "2", when this zone (including the well) exceeded 8 mm. The results are shown in Table 24 below.

TABLE 24

| Material | Inhibition against *P. aeruginosa* | Inhibition against *S. aureus* |
|---|---|---|
| Control | 0 | 2 |
| Cream with CuI | 2 | 2 |

The control cream is known to be effective against Gram positive microorganisms, and the results show the controls inhibited S. aureus, as expected. The CuI creams of the current formulation show equal effectiveness against S aureus. Against the Gram negative P. aeruginosa, the control creams were not expected to show efficacy, and they did not. However, the CuI-based cream did show substantial effectiveness, further bolstering the broad antimicrobial nature of the invention.

It will be understood that various modifications may be made to the embodiments disclosed herein. Therefore, the above description should not be construed as limiting, but merely as exemplifications of preferred embodiments. Those skilled in the art will envision other modifications that come within the scope and spirit of the claims appended hereto. All patents and references cited herein are explicitly incorporated by reference in their entirety.

The invention claimed is:

1. A composition having antimicrobial activity comprising:
   a. mixed-metal halide solid solution particles having the formula (Cu-Me)X, comprising at least one copper ion, at least one second metal Me ion other than copper ion, and a halide X, wherein X is selected from the group consisting of bromide, chloride and iodide; and
   b. at least one functionalizing agent in contact with said mixed-metal halide particles, said functionalizing agent stabilizing said particles in a carrier.

2. The composition of claim 1 wherein said carrier is a liquid.

3. The composition of claim 1, added to an article of manufacture.

4. The composition of claim 2 wherein said functionalizing agent is insoluble in said liquid carrier but stabilizes said particles in said liquid carrier.

5. The composition of claim 1 wherein said particles are complexed by said functionalizing agent.

6. The composition of claim 2 wherein said liquid carrier is water-based.

7. The composition of claim 2 wherein said liquid carrier is oil-based.

8. The composition of claim 2 wherein said particles are suspended in said liquid carrier.

9. The composition of claim 1 wherein said carrier is a solid.

10. The composition of claim 9 wherein said solid carrier comprises a plastic.

11. The composition of claim 1 wherein said halide X is iodide.

12. The composition of claim 1 wherein said mixed-metal halide particles have an average size range of from about 1000 nm to about 4 nm.

13. The composition of claim 1 wherein said mixed-metal halide particles have a solubility of less than about 100 ppm in water at room temperature.

14. The composition of claim 1 wherein said mixed-metal halide particles have a solubility of less than about 15 ppm in water at room temperature.

15. The composition of claim 1 wherein said functionalizing agent is selected from the group consisting of an amino acid, a thiol, a hydrophilic polymer, a hydrophobic polymer, an amphiphilic polymer, surfactants and a target-specific ligand.

16. The composition of claim 15 wherein said hydrophilic polymer is selected from the group consisting of polyvinylpyrrolidone, polyethyleneglycol and copolymers and blends comprising at least one of the monomers which form the said polymer.

17. The composition of claim 15 wherein said hydrophobic polymer is selected from the group consisting of polyurethanes, acrylic polymers, epoxies, silicones and fluorosilicones.

18. The composition of claim 15 wherein said amphiphilic polymer is selected from the group consisting of PVP-block-polypropyleneoxide-block, polyethyleneoxide-block-polypropyleneoxide-block-polyethyleneoxide-block, and polyethyleneoxide-block-polypropylene oxide-block.

19. The composition of claim 3 wherein said article of manufacture is a coating.

20. The composition of claim 1 wherein said second metal ion comprises a silver ion.

21. The composition of claim 20 wherein said functionalized mixed-metal halide particles release copper and silver cations into the environment of a microbe.

22. The composition of claim 15 wherein said surfactants comprise anionic surfactants.

23. The composition of claim 20 wherein said mixed-meta halides are selected from the group consisting of Cu—AgI, Cu—AgBr, and Cu—AgCl.

24. The composition of claim 23 wherein the weight ratio of Cu:Ag ranges from about 10:90 to about 90:10.

25. The composition of claim 1 wherein said halide is selected from the group consisting of bromide, chloride and iodide.

26. A composition having antimicrobial activity comprising:
   a. mixed-metal halide solid solution particles having the formula (Cu—Ag)X, comprising a copper ion, a silver ion, and a halide X, wherein X is selected from the group consisting of bromide, chloride, iodide and mixtures thereof; and
   b. at least one functionalizing agent in contact with said mixed-metal halide particle, said functionalizing agent stabilizing said particle in a carrier.

27. The composition of claim 26 wherein said mixed-metal halides are selected from the group consisting of (Cu—Ag)I, (Cu—Ag)Br, (Cu—Ag)Cl, (Cu—Ag) (I, Br), (Cu—Ag) (I, Cl) and (Cu—Ag) (Br, Cl).

28. A composition having antimicrobial activity comprising:
   a. mixed-metal halide particles comprising at least one copper halide and at least a second different copper halide; and
   b. at least one functionalizing agent in contact with said mixed-metal halide particles, said functionalizing agent stabilizing said particles in a carrier such that an antimicrobially effective amount of ions are released into the environment of a microbe.

29. The composition of claim 28 wherein said copper halides are selected from the group consisting of CuI, CuBr and CuCl.

30. The composition of claim 1 wherein said mixed-metal halide has the formula $(Ag_{(1-x)}Cu_x)I$ wherein X may be from 0.90 to 0.10.

31. The composition of claim 30, wherein said mixed metal halide has the formula $(Ag_{0.25}Cu_{0.75})I$.

* * * * *